United States Patent
Kamabuchi et al.

(10) Patent No.: US 10,377,692 B2
(45) Date of Patent: *Aug. 13, 2019

(54) PHOTORESIST COMPOSITION

(75) Inventors: Akira Kamabuchi, Kobe (JP); Yuko Yamashita, Toyonaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 598 days.

This patent is subject to a terminal disclaimer.

(21) Appl. No.: 12/875,627

(22) Filed: Sep. 3, 2010

(65) Prior Publication Data

US 2011/0059400 A1 Mar. 10, 2011

(30) Foreign Application Priority Data

Sep. 9, 2009 (JP) ................. 2009-207964
Dec. 24, 2009 (JP) ................. 2009-292266
Jul. 27, 2010 (JP) ................. 2010-167946
Jul. 27, 2010 (JP) ................. 2010-167947

(51) Int. Cl.
*C07C 61/135* (2006.01)
*G03F 7/004* (2006.01)
*G03F 7/039* (2006.01)

(52) U.S. Cl.
CPC .......... *C07C 61/135* (2013.01); *G03F 7/0045* (2013.01); *G03F 7/0397* (2013.01); *G03F 7/0046* (2013.01)

(58) Field of Classification Search
None
See application file for complete search history.

(56) References Cited

U.S. PATENT DOCUMENTS

| 5,525,453 | A | * | 6/1996 | Przybilla et al. ............. 430/170 |
| 5,914,216 | A |   | 6/1999 | Amou et al. |
| 6,319,649 | B1 |  | 11/2001 | Kato et al. |
| 2004/0053160 | A1 | * | 3/2004 | Takahashi et al. ........ 430/270.1 |
| 2005/0032373 | A1 | * | 2/2005 | Cameron .............. G03F 7/0392 438/689 |
| 2006/0147836 | A1 | * | 7/2006 | Hatakeyama ......... G03F 7/0045 430/270.1 |
| 2008/0153030 | A1 | * | 6/2008 | Kobayashi et al. ....... 430/270.1 |
| 2008/0227031 | A1 |   | 9/2008 | Cameron |
| 2009/0202943 | A1 | * | 8/2009 | Ohsawa ............... G03F 7/0045 430/285.1 |
| 2010/0119972 | A1 |   | 5/2010 | Houlihan et al. |
| 2010/0279226 | A1 | * | 11/2010 | Hata ..................... G03F 7/0035 430/270.1 |

FOREIGN PATENT DOCUMENTS

| JP | 2001166474 A | * | 6/2001 |
| JP | 2004-85931 A |   | 3/2004 |
| JP | 2009157338 A | * | 7/2009 |
| JP | 2010-160446 A |   | 7/2010 |
| JP | 2010-237313 A |   | 10/2010 |
| JP | 2010237313 A | * | 10/2010 |
| JP | 2010-271686 A |   | 12/2010 |
| WO | WO-2009084515 A1 | * | 7/2009 | .......... G03F 7/0035 |

OTHER PUBLICATIONS

Kon et al., High-performance EB chemically amplified resist using alicyclic protective groups, Jun. 23, 2000, Proceedings of SPIE, vol. 3999, 1207-1214.*
English Translation of JP2001166474.*
English translation of JP2009157338. (Year: 2009).*
Japanese Office Action corresponding to JP Application No. 2010-167946 with English Translation attached herewith.
Notice of Reasons for the Rejection Corresponding to Japanese Application No. 2008-287223.
Notice of Reasons for Rejection corresponding to JP Patent Application No. 2010-167946.
Examination Report corresponding to TW Patent Application No. 10420447180 dated Apr. 9, 2015.
Examination Report corresponding to TW Patent Application No. 10321221290 dated Sep. 2, 2014.

\* cited by examiner

*Primary Examiner* — Chanceity N Robinson
*Assistant Examiner* — Anna Malloy
(74) *Attorney, Agent, or Firm* — Hogan Lovells US LLP

(57) ABSTRACT

A photoresist composition comprising a resin which comprises a structural unit derived from a compound having an acid-labile group and which is insoluble or poorly soluble in an alkali aqueous solution but becomes soluble in an alkali aqueous solution by the action of an acid, an acid generator and a compound represented by the formula (I'):

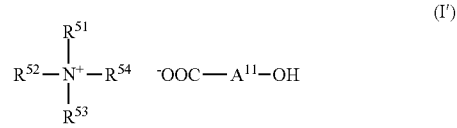

(I')

wherein $R^{51}$, $R^{52}$, $R^{53}$ and $R^{54}$ independently each represent a C1-C8 alkyl group, and $A^{11}$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents.

4 Claims, No Drawings

PHOTORESIST COMPOSITION

This nonprovisional application claims priority under 35 U.S.C. § 119(a) on Patent Application No. 2009-207964 filed in JAPAN on Sep. 9, 2009, on Patent Application No. 2009-292266 filed in JAPAN on Dec. 24, 2009, on Patent Application No. 2010-167946 filed in JAPAN on Jul. 27, 2010, and on Patent Application No. 2010-167947 filed in JAPAN on Jul. 27, 2010, the entire contents of which are hereby incorporated by reference.

FIELD OF THE INVENTION

The present invention relates to a photoresist composition.

BACKGROUND OF THE INVENTION

A photoresist composition used for semiconductor microfabrication employing a lithography process contains a resin having a structural unit derived from a compound having an acid-labile group, being insoluble or poorly soluble in an alkali aqueous solution but becoming soluble in an alkali aqueous solution by the action of an acid, an acid generator comprising a compound generating an acid by irradiation and a basic compound.

U.S. Pat. No. 5,914,219 discloses a photoresist composition comprising a resin having a structural unit derived from a compound having an acid-labile group, being insoluble or poorly soluble in an alkali aqueous solution but becoming soluble in an alkali aqueous solution by the action of an acid, an acid generator comprising a compound generating an acid by irradiation and tetrabutylammonium hydroxide as a basic compound.

SUMMARY OF THE INVENTION

The present invention is to provide a photoresist composition.

The present invention relates to the followings:

<1> A photoresist composition comprising
a resin which comprises a structural unit derived from a compound having an acid-labile group and which is insoluble or poorly soluble in an alkali aqueous solution but becomes soluble in an alkali aqueous solution by the action of an acid,
an acid generator and
a compound represented by the formula (I'):

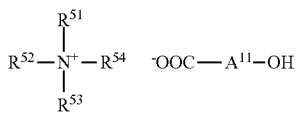

wherein $R^{51}$, $R^{52}$, $R^{53}$ and $R^{54}$ independently each represent a C1-C8 alkyl group, and $A^{11}$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents;

<2> The photoresist composition according to <1>, wherein the compound represented by the formula (I') is a compound represented by the formula (I):

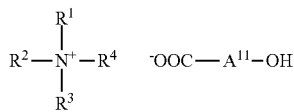

wherein $R^2$, $R^2$, $R^3$ and $R^4$ independently each represent a C1-C6 alkyl group, and $A^1$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents;

<3> The photoresist composition according to <1> or <2>, wherein the resin comprises a structural unit derived from a compound represented by the formula (a2-0):

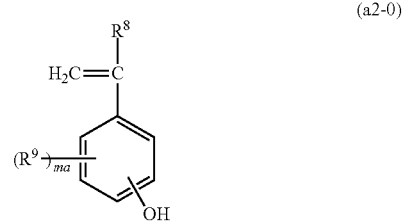

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4;

<4> The photoresist composition according to any one of <1> to <3>, wherein the compound having an acid-labile group is a compound represented by the formula (a1-1):

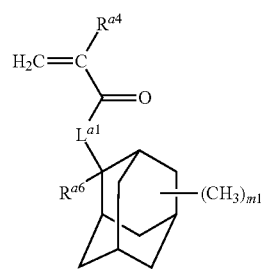

wherein $R^{a4}$ represents a hydrogen atom or a methyl group, $R^{a6}$ represents a C1-C8 aliphatic hydrocarbon group or a C3-C10 saturated cyclic hydrocarbon group, $L^{a1}$ represents *—O— or *—O—(CH$_2$)$_{k1}$—CO—O— in which * represents a binding position to —CO—, and k1 represents an integer of 1 to 7, and m1 represents an integer of 0 to 14;

<5> A process for producing a photoresist pattern comprising the following steps (1) to (5):
(1) a step of applying the photoresist composition according to any one of <1> to <4> on a substrate,
(2) a step of forming a photoresist film by conducting drying,
(3) a step of exposing the photoresist film to radiation, (4) a step of baking the exposed photoresist film, and (5) a step of developing the baked photoresist film with an alkaline developer, thereby forming a photoresist pattern;

<6> Use of the photoresist composition according to any one of <1> to <4> for producing a photoresist pattern using an electron beam lithography system or an extreme ultraviolet lithography system;

<7> A compound represented by the formula (I-12):

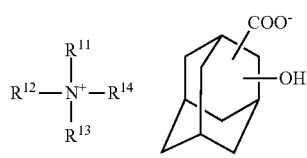

(I-12)

wherein $R^{11}$, $R^{12}$, $R^{13}$ and $R^{14}$ independently each represent a C1-C6 alkyl group;

<8> A photoresist composition comprising
a resin which comprises a structural unit derived from a compound having an acid-labile group and a structural unit derived from a compound represented by the formula (a2-10):

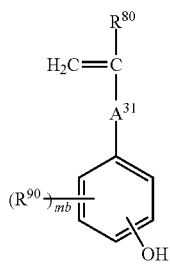

(a2-10)

wherein $R^{80}$ represents a hydrogen atom, a halogen atom, a C1-C6 alkyl group or a C1-C6 halogenated alkyl group, $R^{90}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, mb represents an integer of 0 to 4, and $A^{31}$ represents a divalent connecting group, and which is insoluble or poorly soluble in an alkali aqueous solution but becomes soluble in an alkali aqueous solution by the action of an acid, an acid generator and a compound represented by the formula (I″):

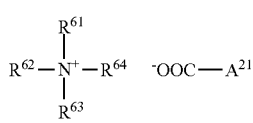

(I″)

wherein $R^{61}$, $R^{62}$, $R^{63}$ and $R^{64}$ independently each represent a C1-C20 alkyl group which can have one or more substituents, a C3-C30 saturated cyclic hydrocarbon group which can have one or more substituents, or a C2-C20 alkenyl group which can have one or more substituents, and $A^{21}$ represents a C1-C36 hydrocarbon group which can contain one or more heteroatoms and which have one or more substituents;

<9> The photoresist composition according to <8>, wherein the compound represented by the formula (I″) is a compound represented by the formula (I′):

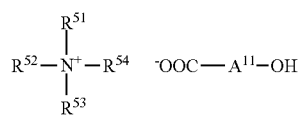

(I′)

wherein $R^{51}$, $R^{52}$, $R^{53}$ and $R^{54}$ independently each represent a C1-C8 alkyl group, and $A^{11}$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents;

<10> The photoresist composition according to <8> or <9>, wherein the compound having an acid-labile group is a compound represented by the formula (a1-1):

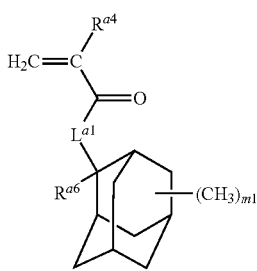

(a1-1)

wherein $R^{a4}$ represents a hydrogen atom or a methyl group, $R^{a6}$ represents a C1-C8 aliphatic hydrocarbon group or a C3-C10 saturated cyclic hydrocarbon group, $L^{a1}$ represents *—O— or *—O—$(CH_2)_{k1}$—CO—O— in which * represents a binding position to —CO—, and k1 represents an integer of 1 to 7, and m1 represents an integer of 0 to 14;

<11> A process for producing a photoresist pattern comprising the following steps (1) to (5):

(1) a step of applying the photoresist composition according to any one of <8> to <10> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern;

<12> Use of the photoresist composition according to any one of <8> to <10> for producing a photoresist pattern using an electron beam lithography system or an extreme ultraviolet lithography system.

DESCRIPTION OF PREFERRED EMBODIMENTS

The first photoresist composition of the present invention comprises a resin which comprises a structural unit derived from a compound having an acid-labile group and which is insoluble or poorly soluble in an alkali aqueous solution but becomes soluble in an alkali aqueous solution by the action of an acid,
an acid generator and
a compound represented by the formula (I').

First, the resin will be illustrated.

The resin is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (10):

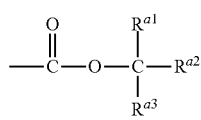

(10)

wherein $R^{a1}$, $R^{a2}$ and $R^{a3}$ independently each represent an aliphatic hydrocarbon group or a saturated cyclic hydrocarbon group, and $R^{a1}$ and $R^{a2}$ can be bonded each other to form a ring.

Examples of the aliphatic hydrocarbon group include a C1-C8 aliphatic hydrocarbon group such as a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. Examples of the saturated cyclic hydrocarbon group include a C3-C20 alicyclic hydrocarbon group. The alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

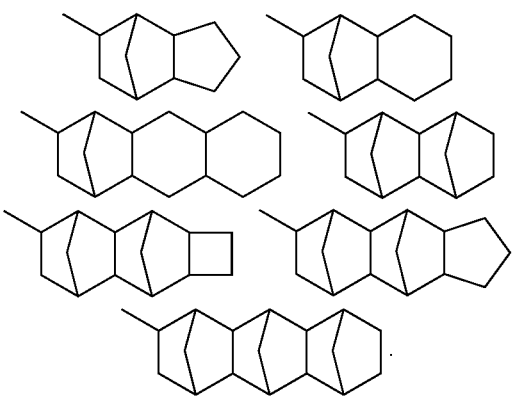

The alicyclic hydrocarbon group preferably has 5 to 20 carbon atoms.

Examples of the ring formed by bonding $R^{a1}$ and $R^{a2}$ each other include the following groups and the ring preferably has 5 to 20 carbon atoms.

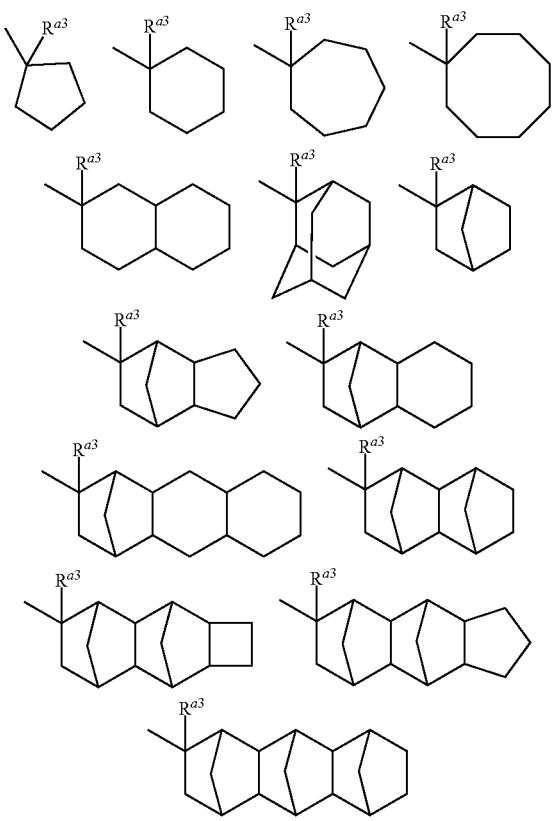

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably an acrylate monomer having an acid-labile group in its side chain or a methacryalte monomer having an acid-labile group in its side chain.

Preferable examples of the compound having an acid-labile group include monomers represented by the formulae (a1-1) and (a1-2):

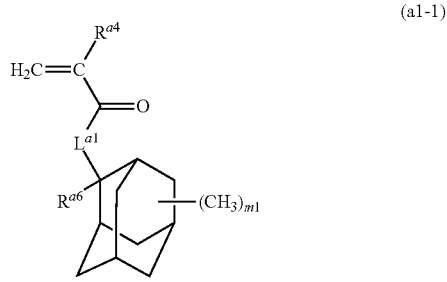

(a1-1)

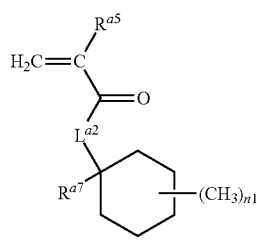

(a1-2)

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 saturated cyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 and n1 each independently represents an integer of 0 to 14, and the monomer represented by the formula (a1-1) is more preferable.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

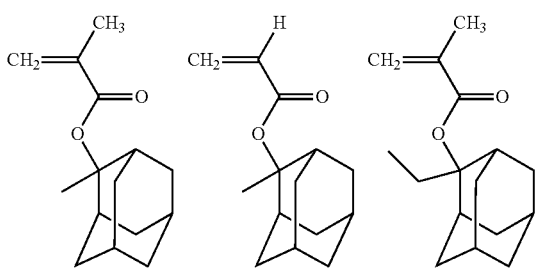

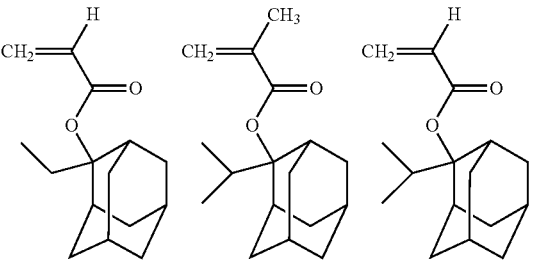

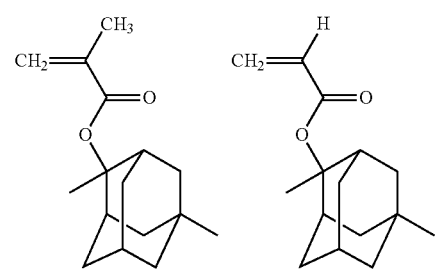

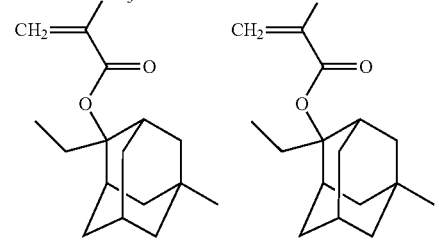

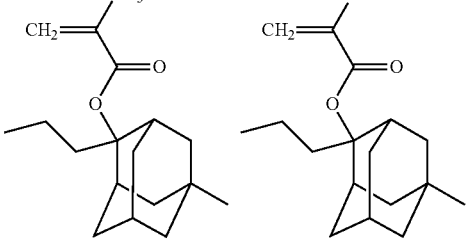

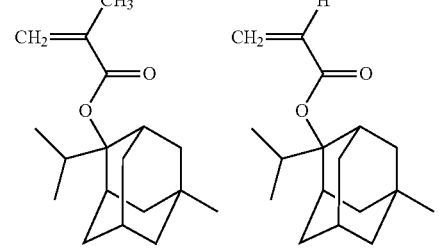

-continued
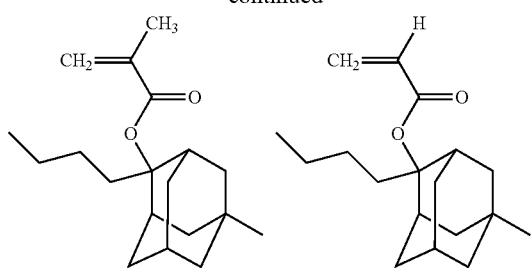
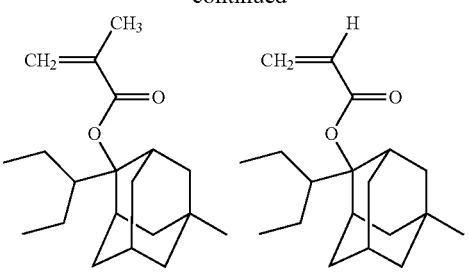
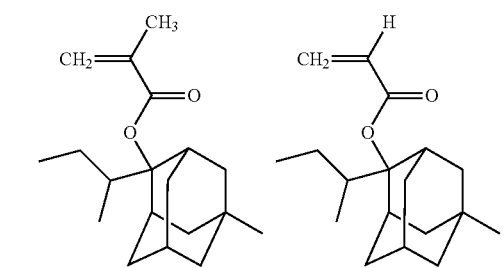
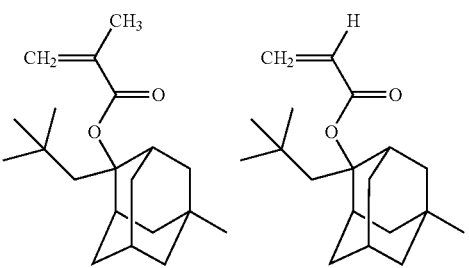
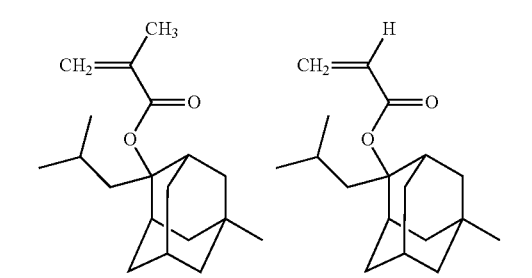
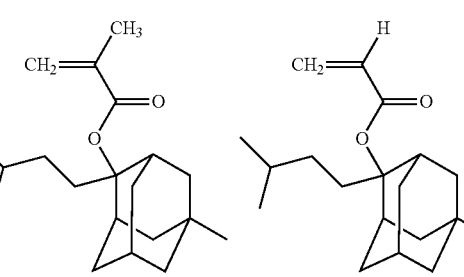
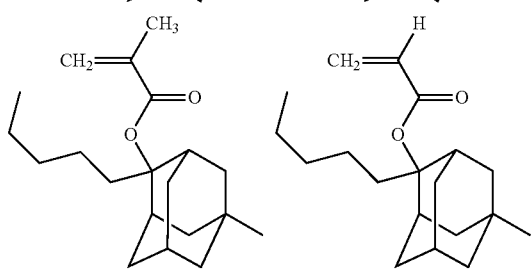
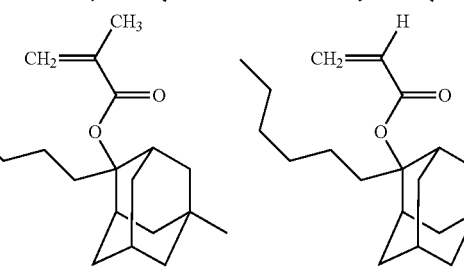
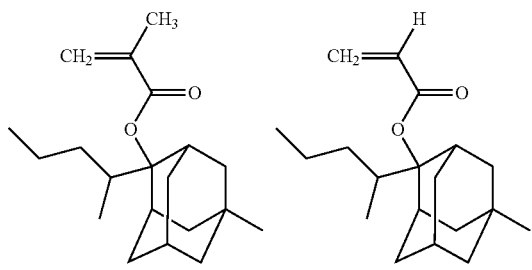
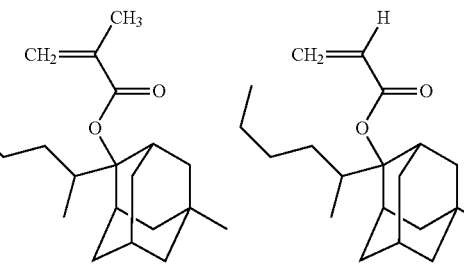
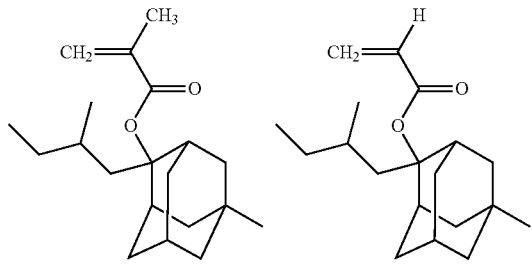
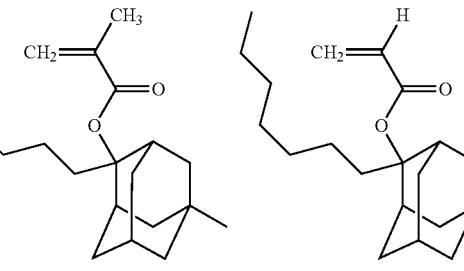

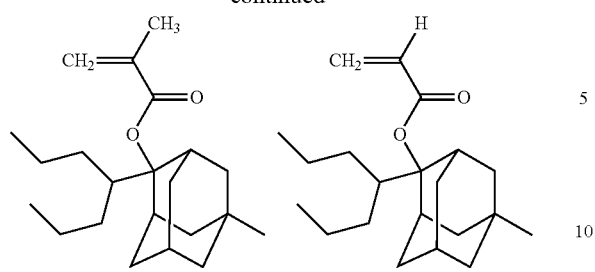
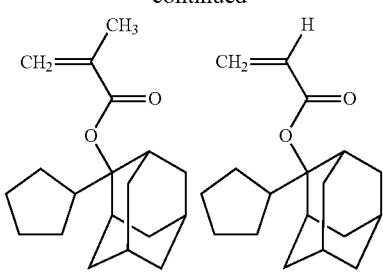
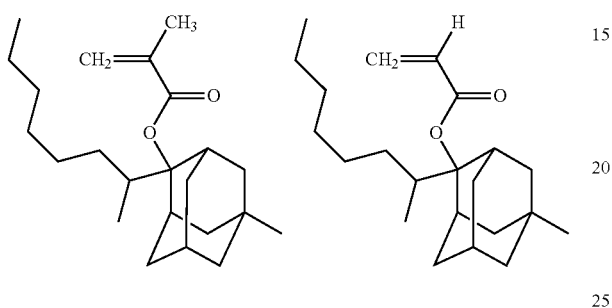
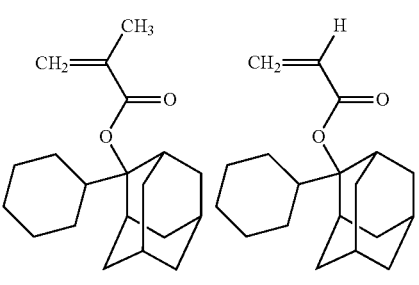
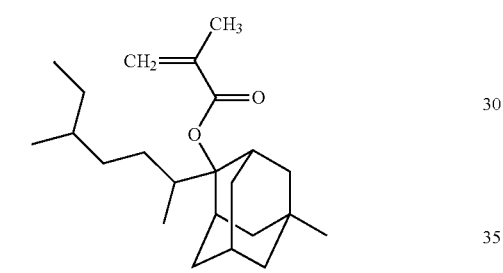
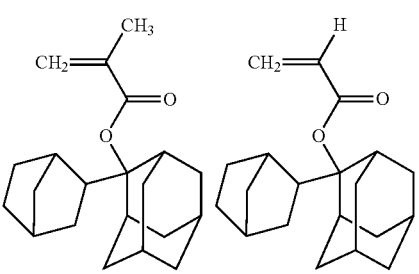
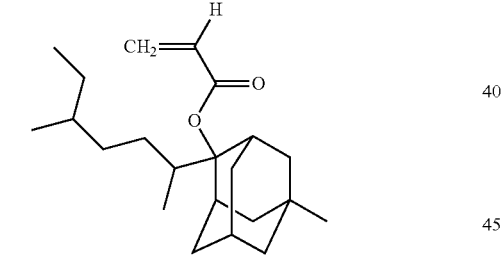
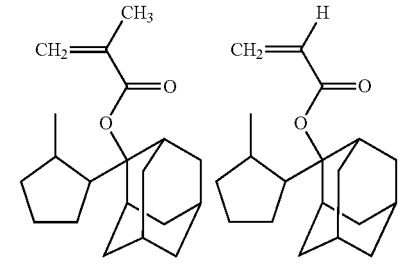
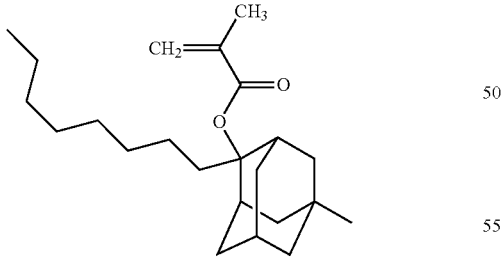
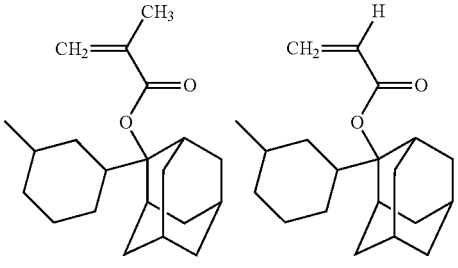
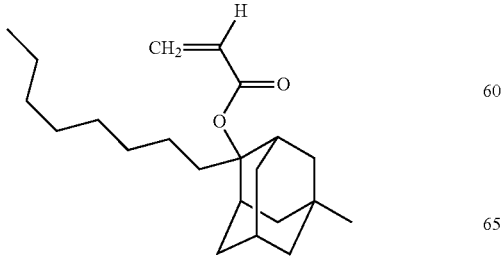
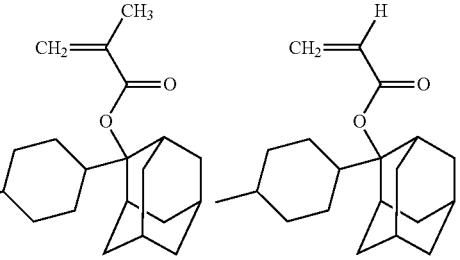

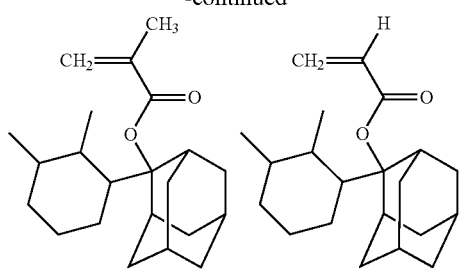
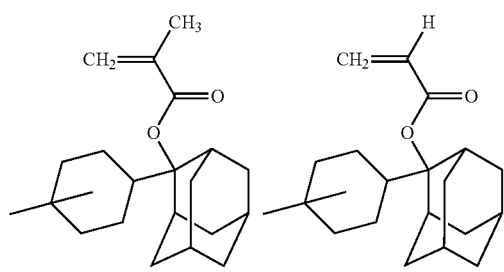
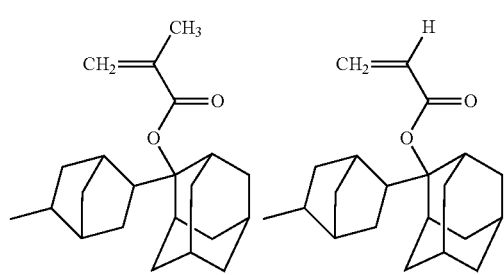
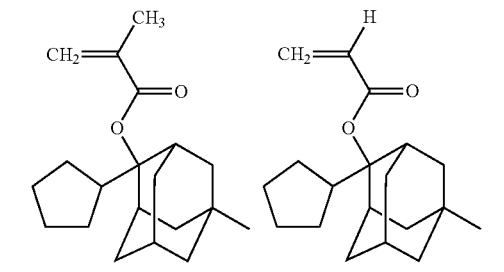
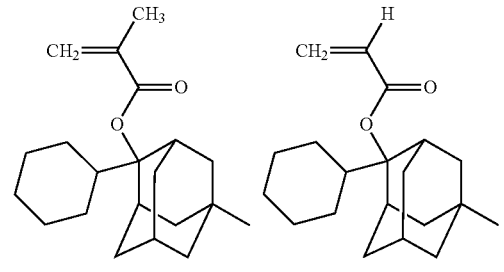
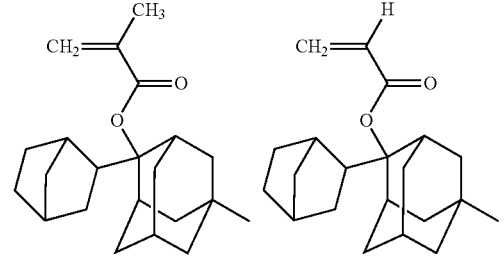
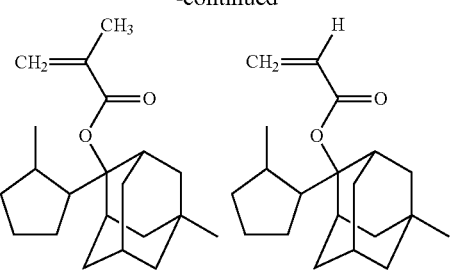
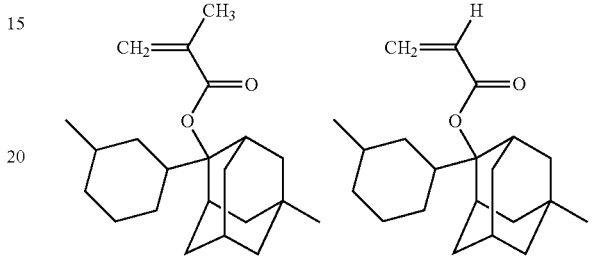
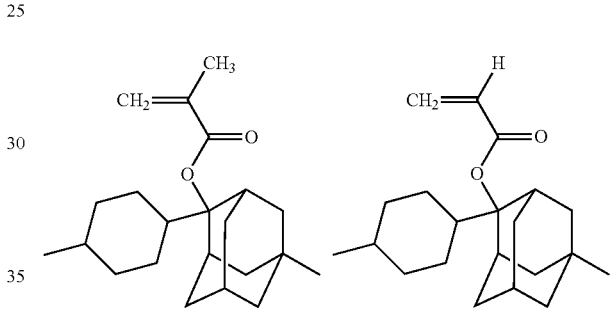
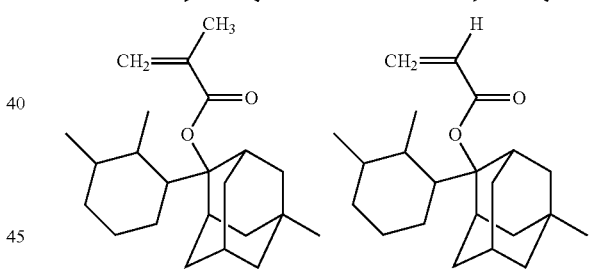
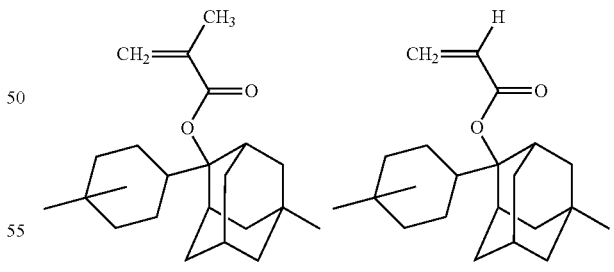
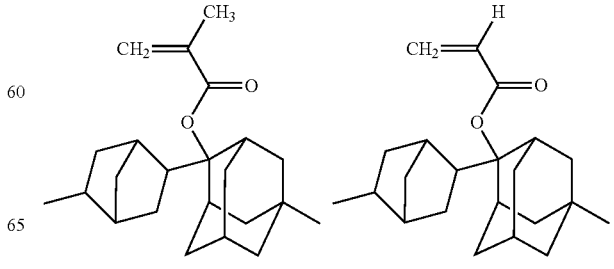

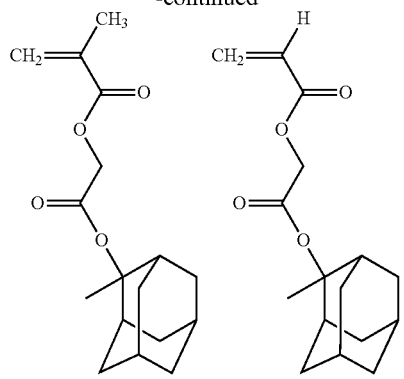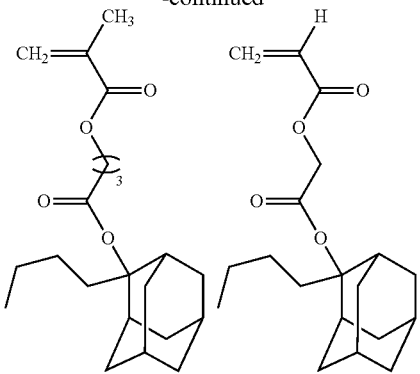

-continued
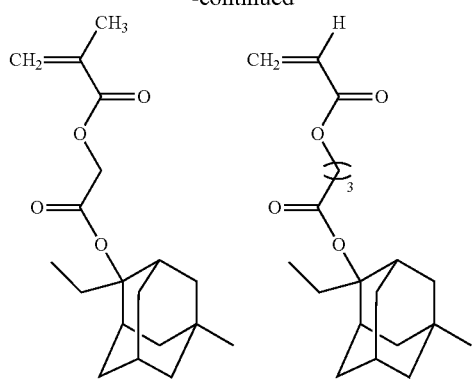
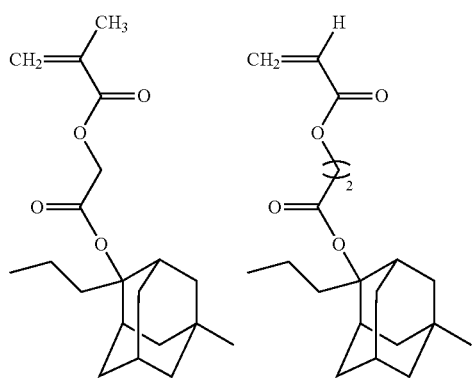
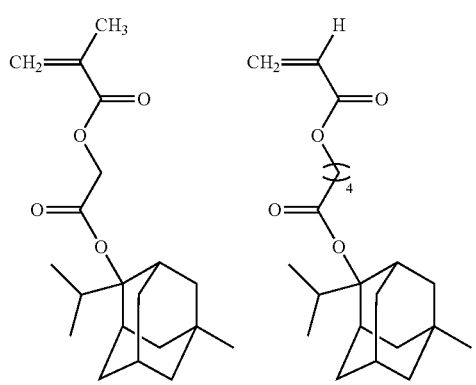
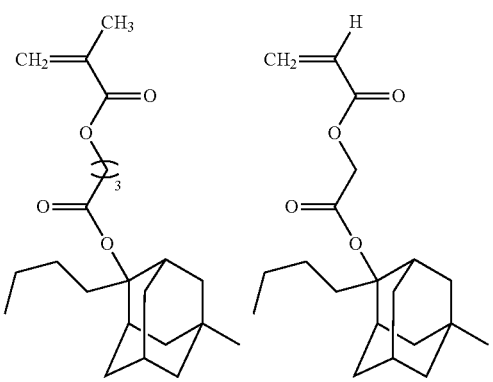
-continued
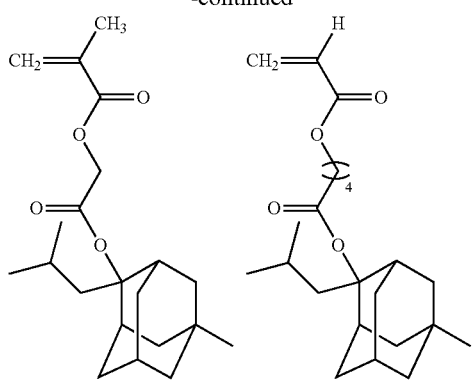
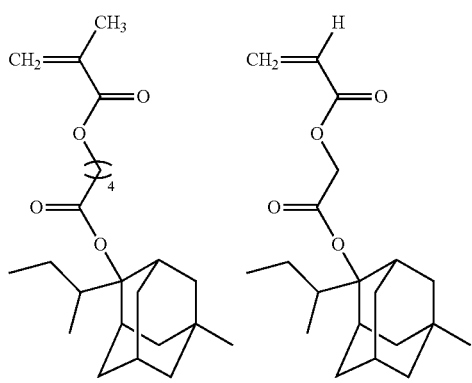
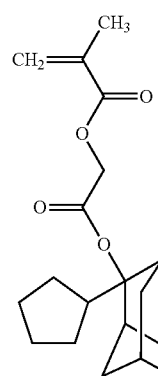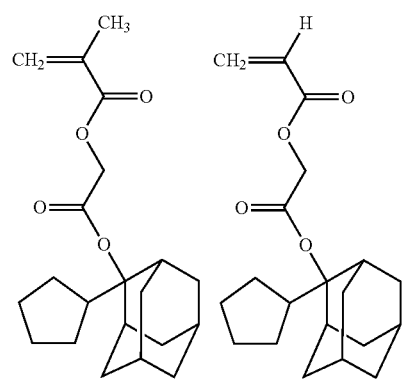
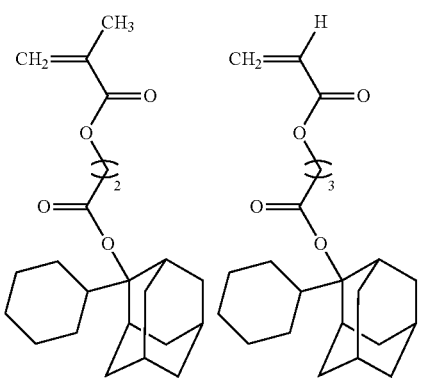

-continued
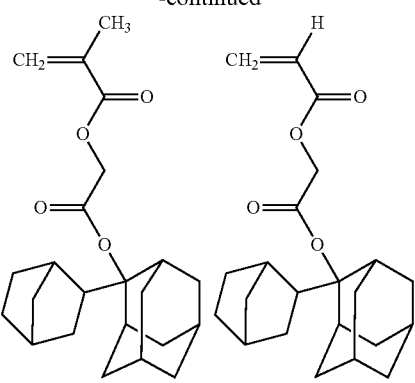
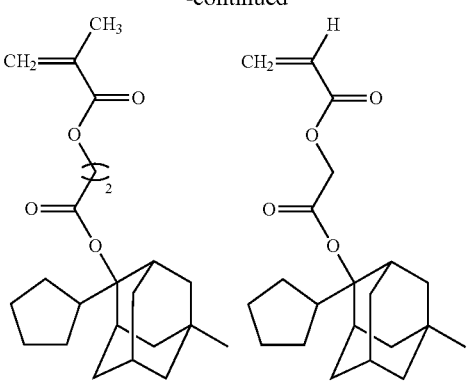
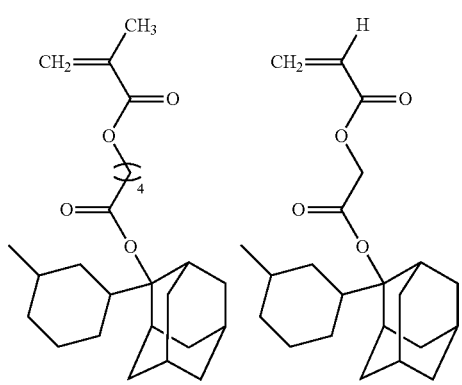
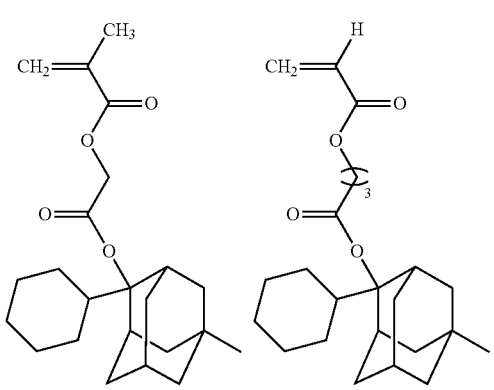
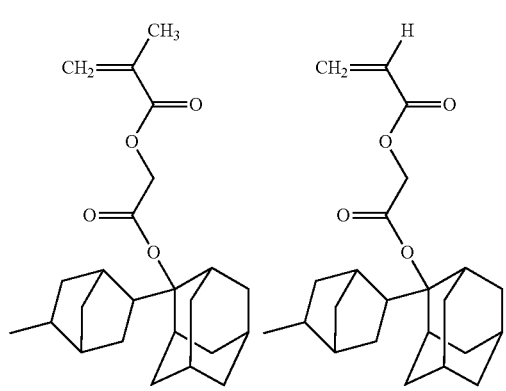
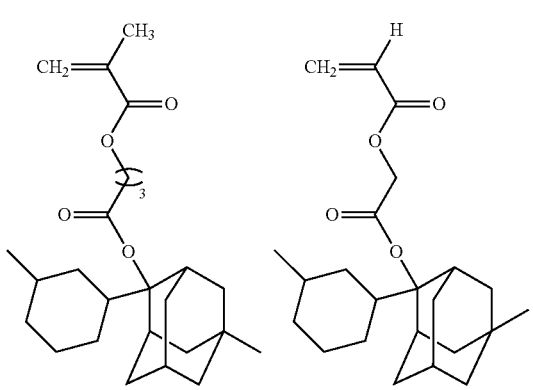

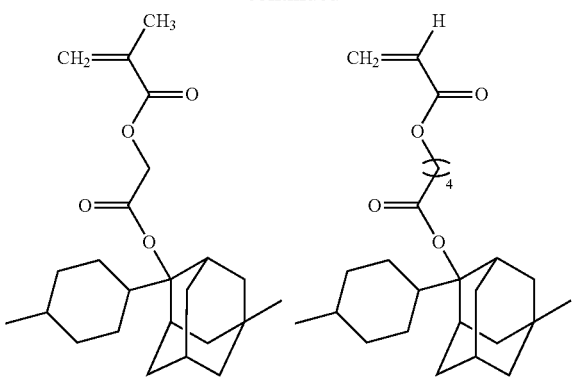

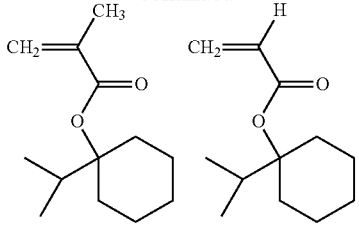

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a1-3):

(a1-3)

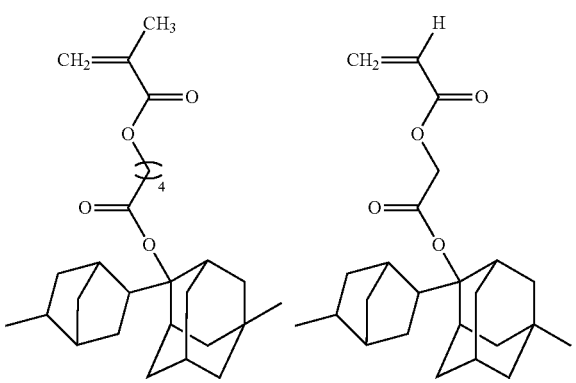

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

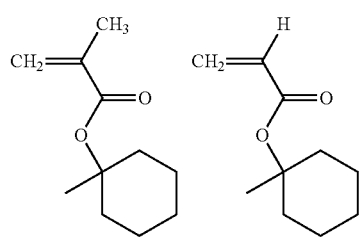

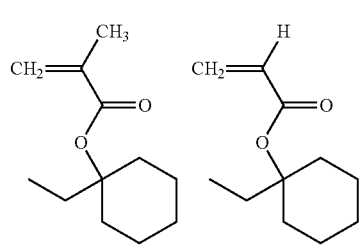

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

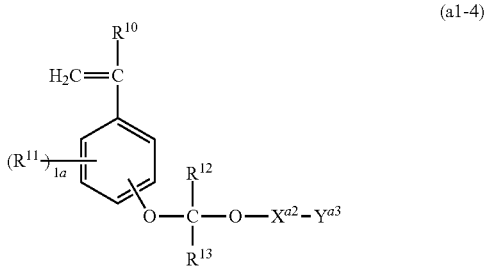

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —$CH_2$— can be replaced by —O—, —CO—, —S—, —$SO_2$— or —N($R^c$)— wherein $R^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

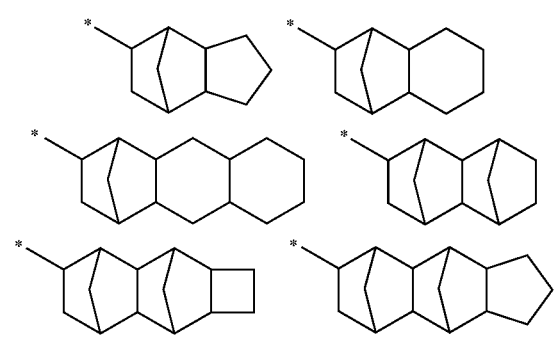

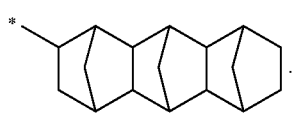
Examples of the C6-C18 aromatic hydrocarbon group include a phenyl group, a naphthyl group, an anthryl group, a p-methylphenyl group, a p-tert-butylphenyl group and a p-adamantylphenyl group.
Examples of the monomer represented by the formula (a1-4) include the followings.
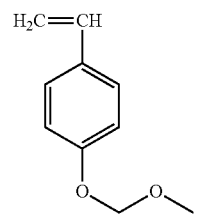
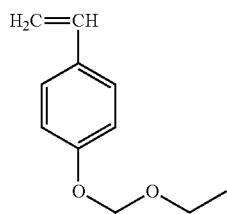
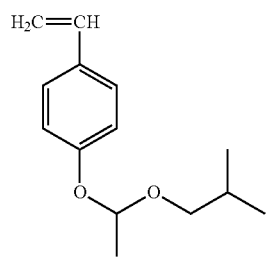
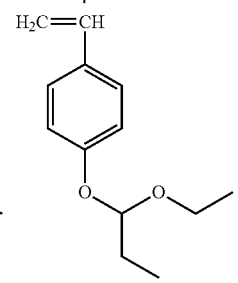
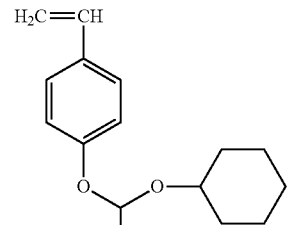
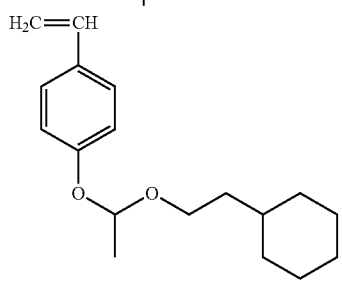
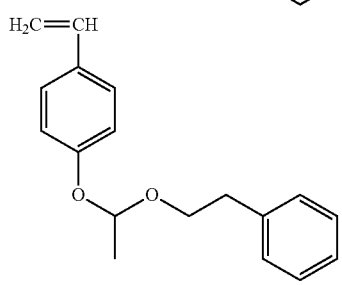
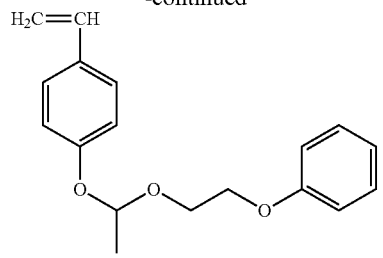
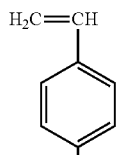
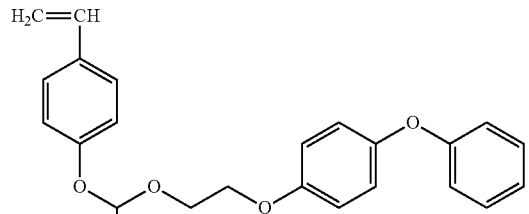
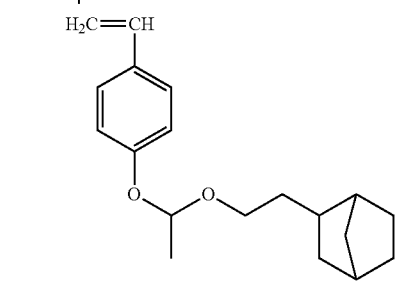
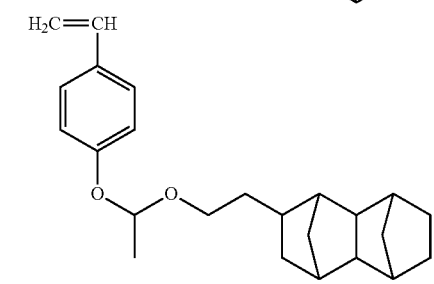
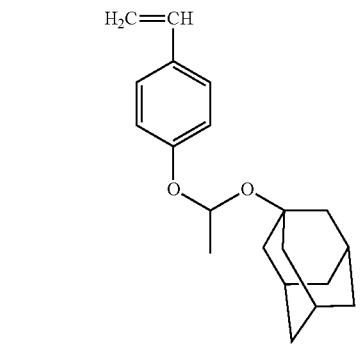

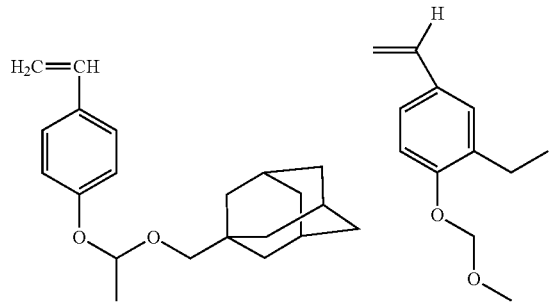
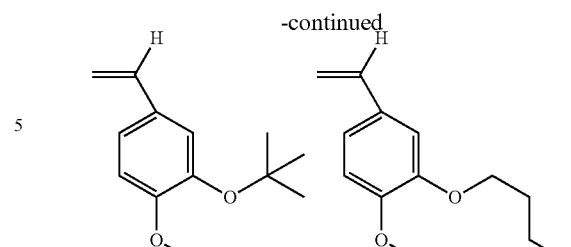
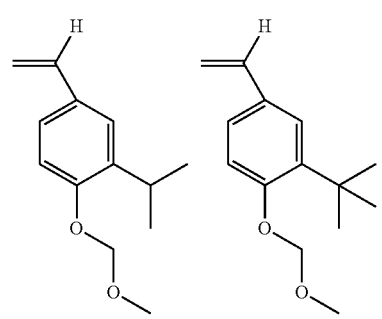
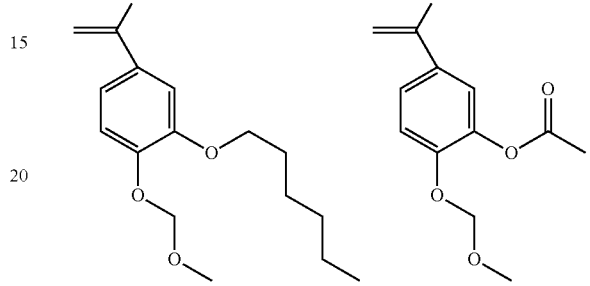
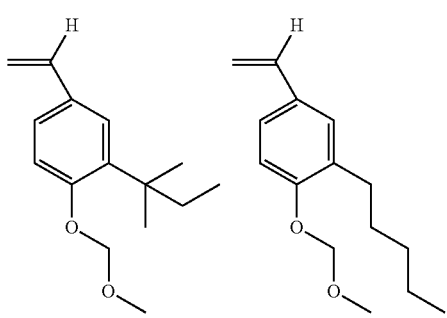
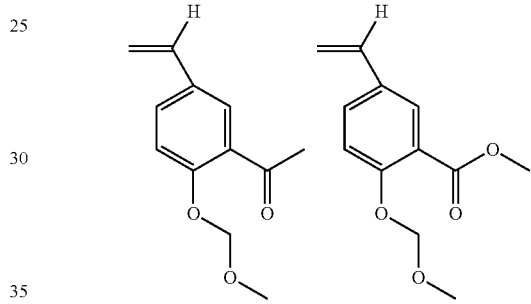
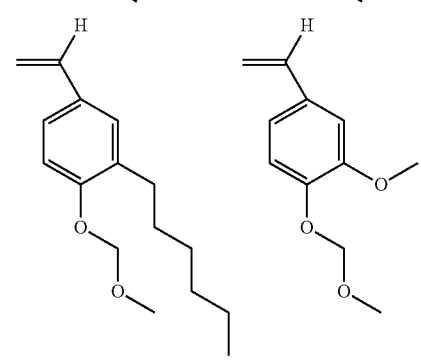
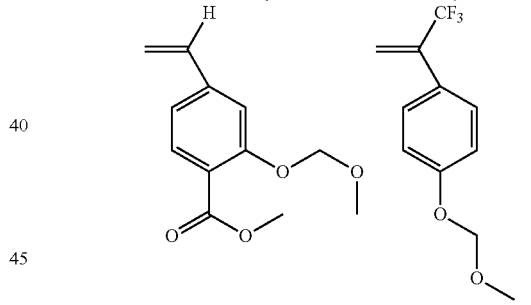
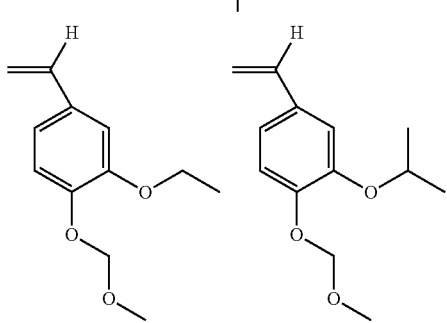

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (a2-0):

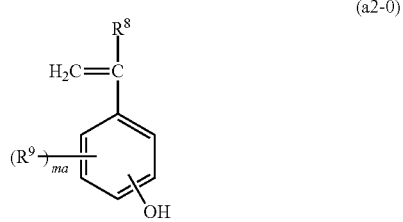

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and
a monomer represented by the formula (a2-1):

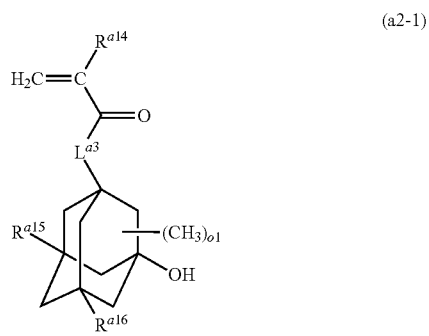

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

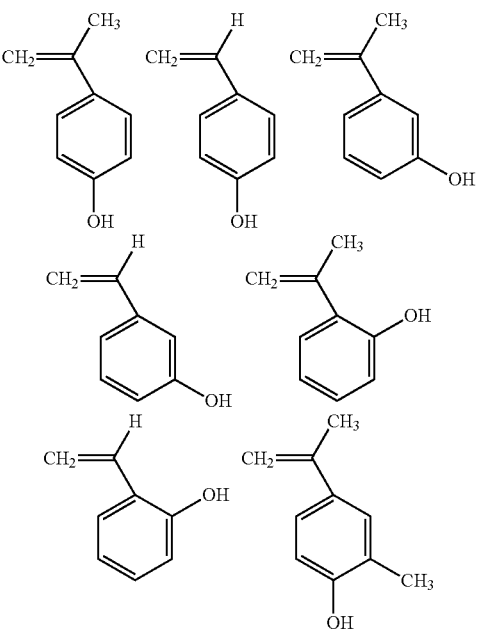

-continued
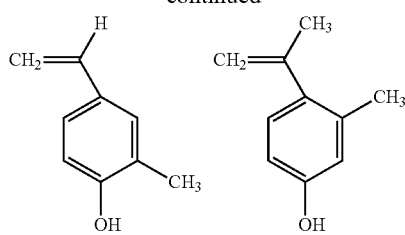
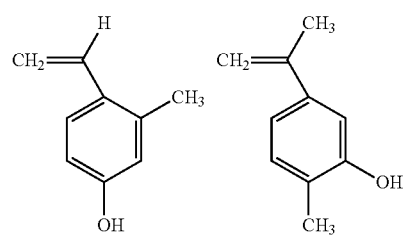
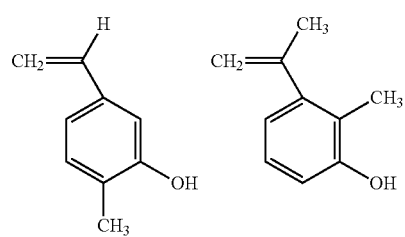
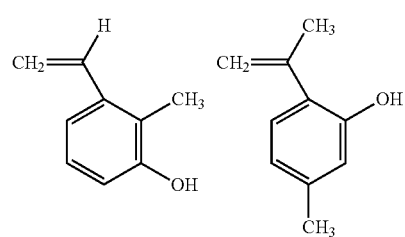
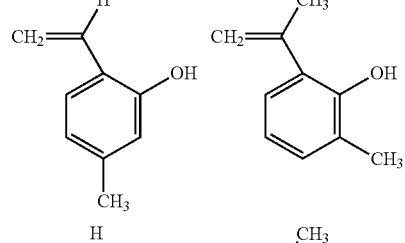
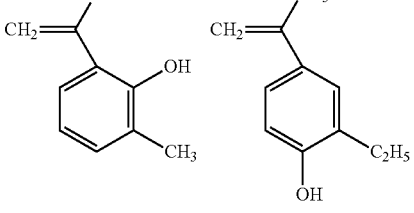
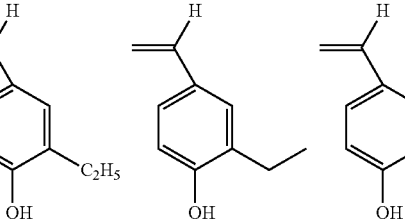
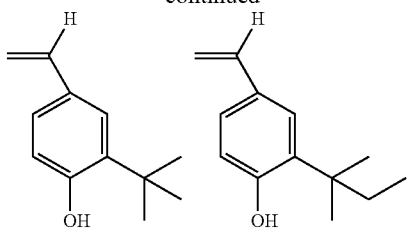
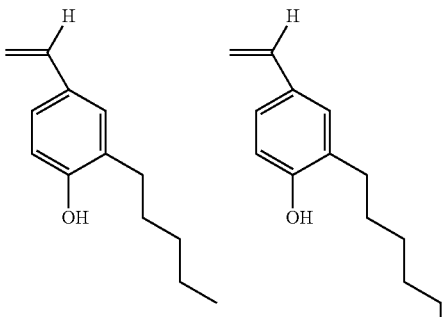
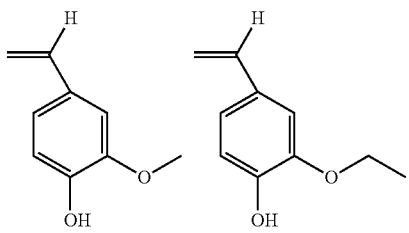
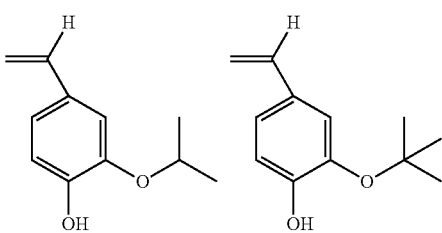
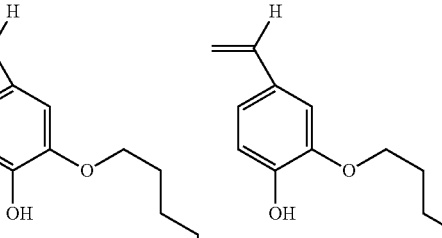
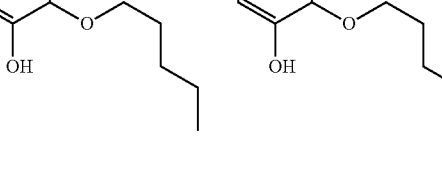
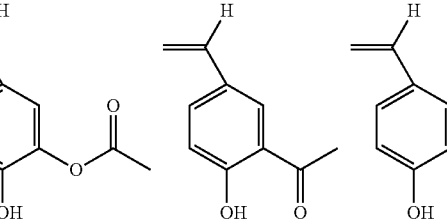

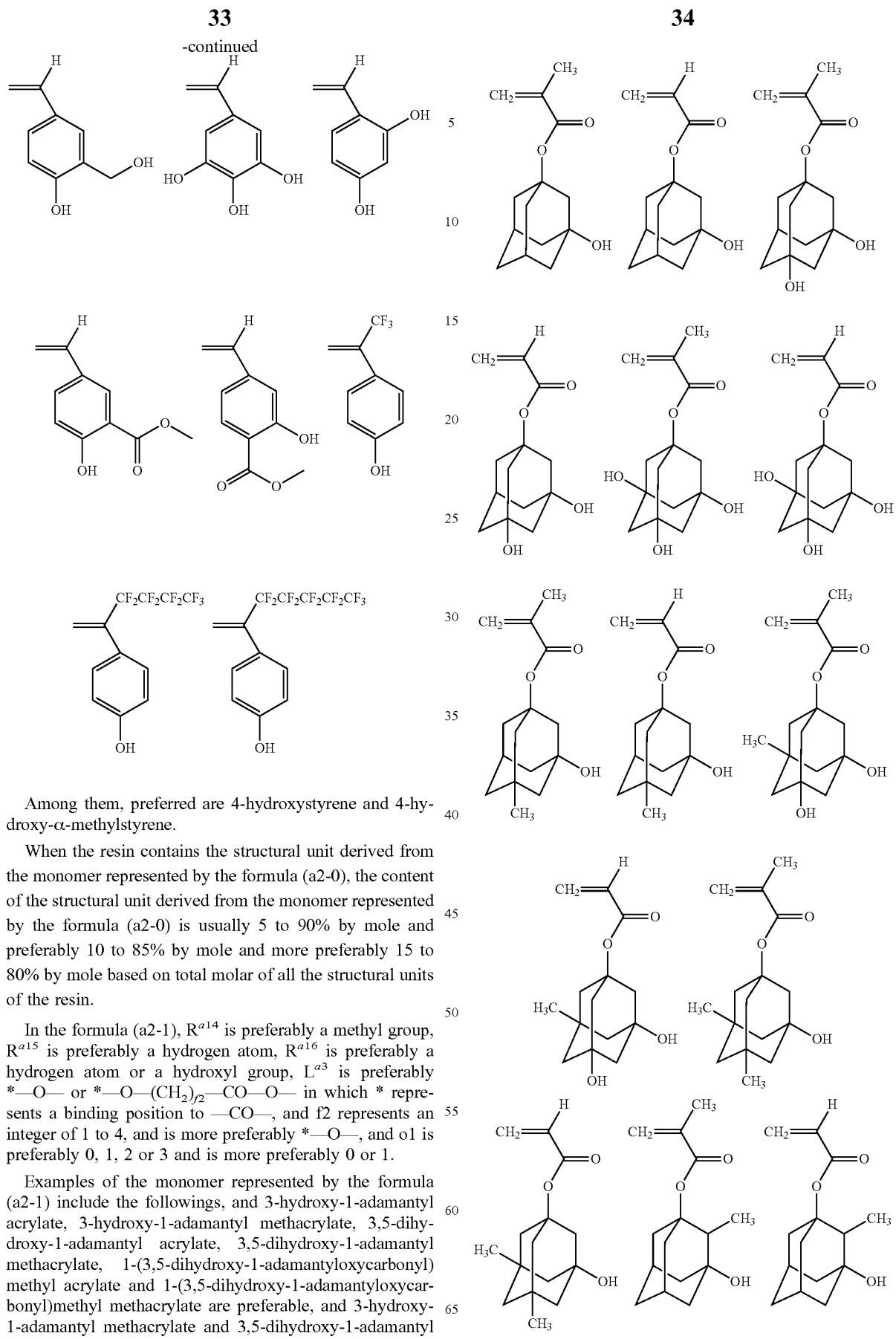

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—(CH$_2$)$_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

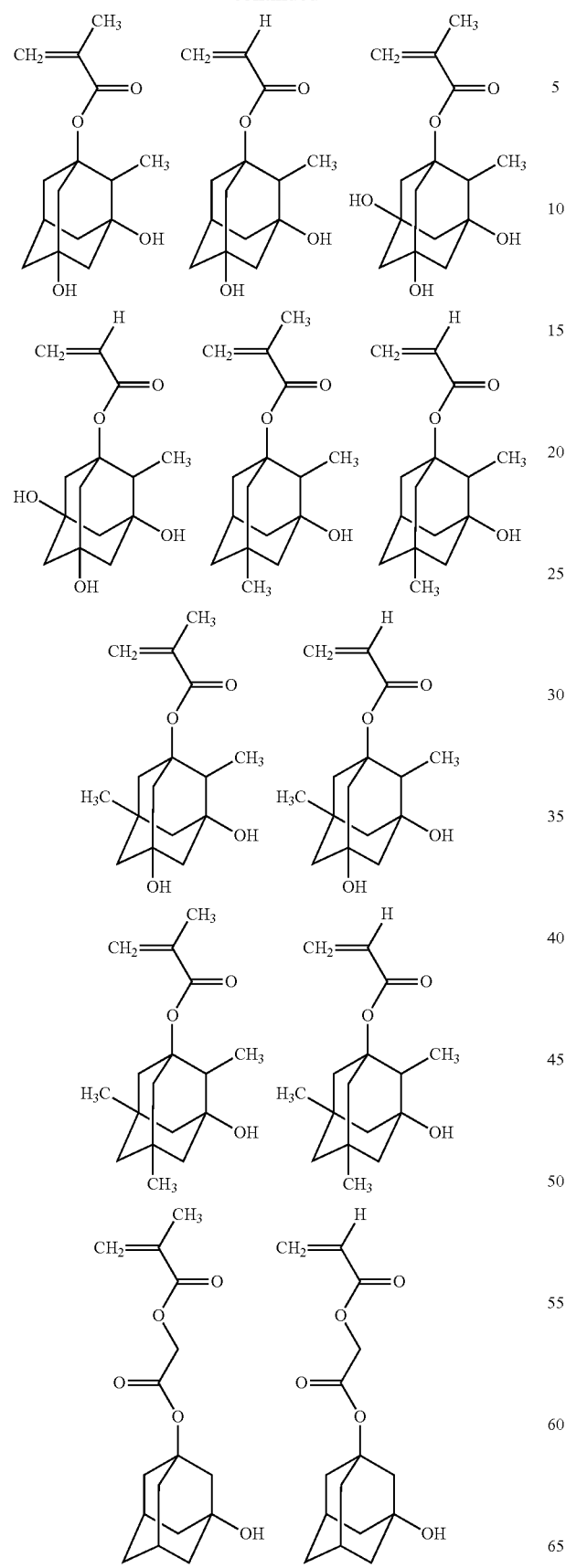
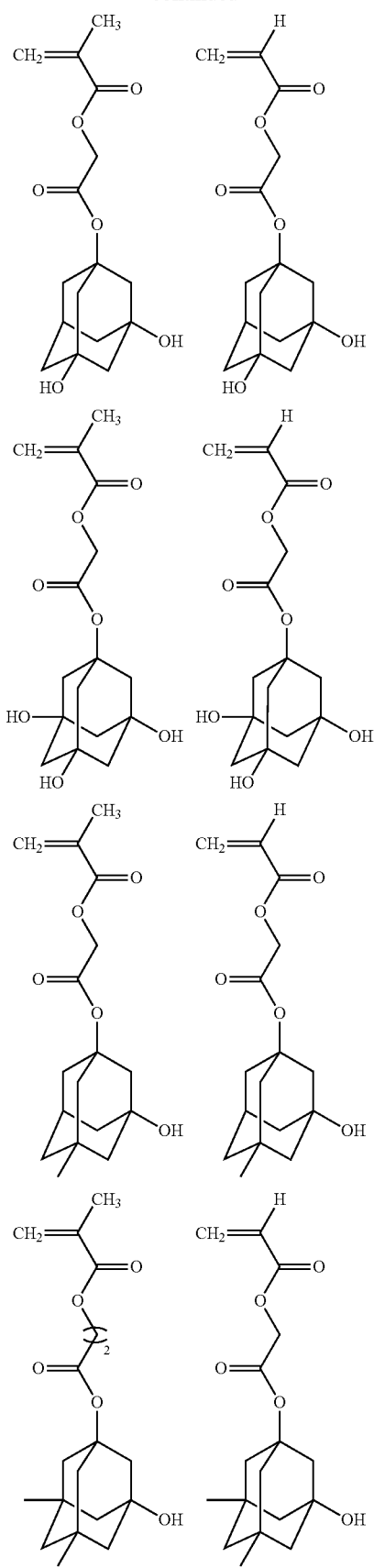

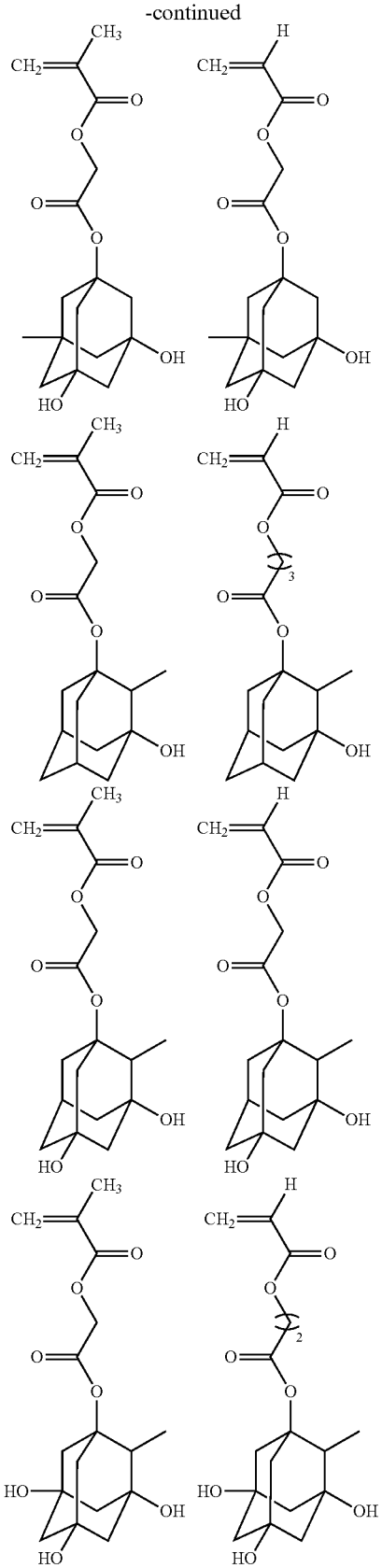

When the resin contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of the resin.

Examples of the lactone ring of the compound having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

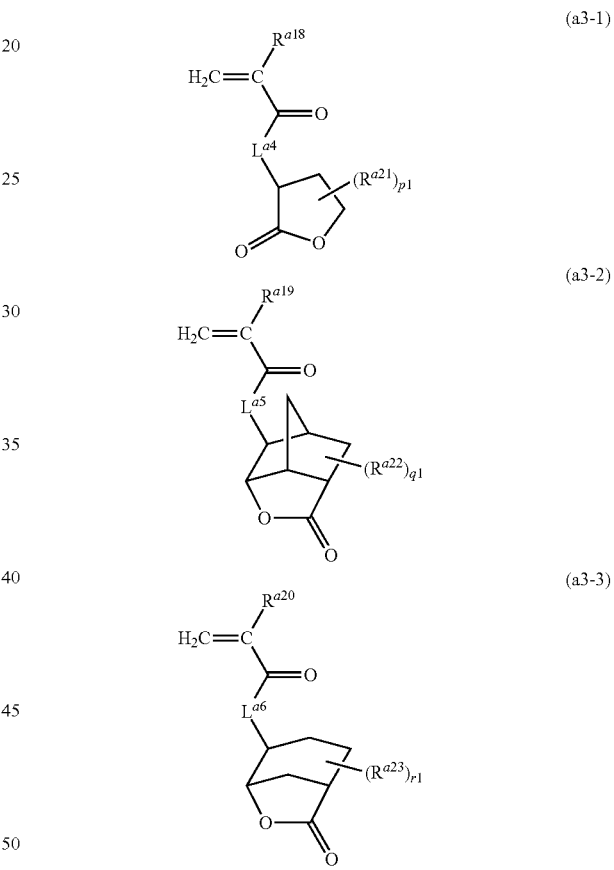

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a23}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

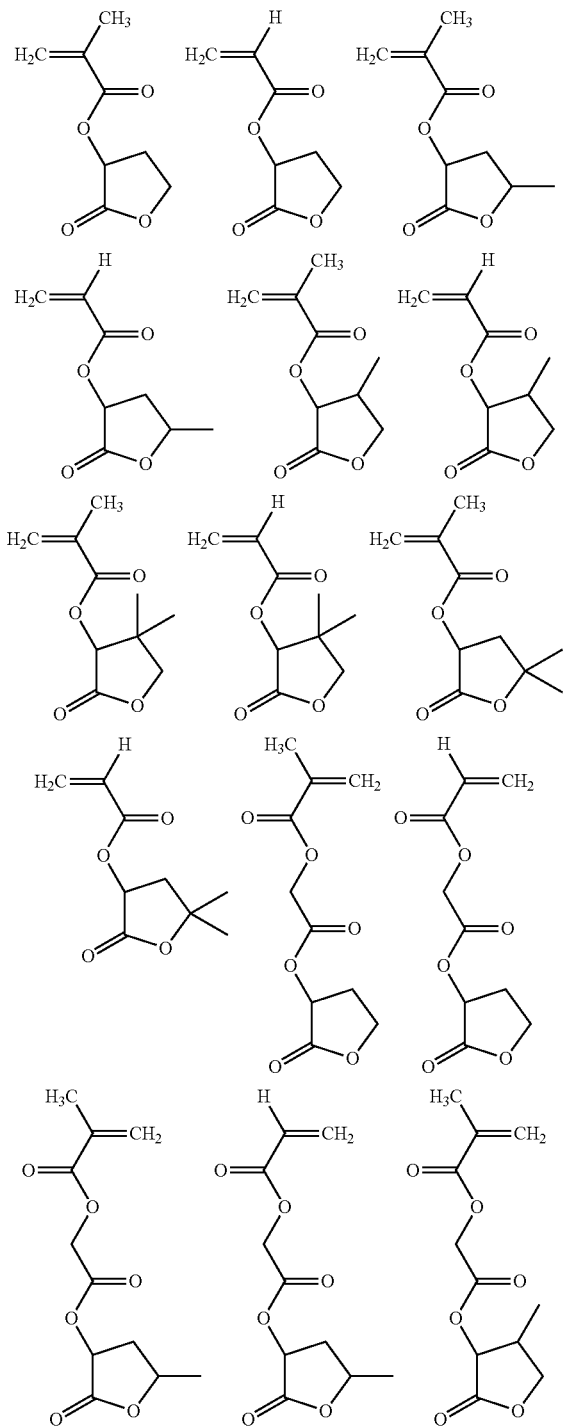
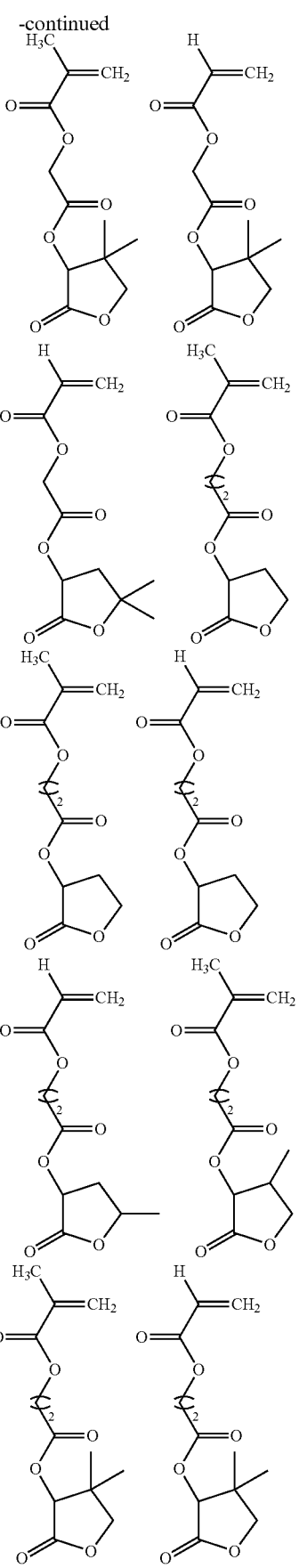

Examples of the monomer represented by the formula (a3-2) include the followings.

-continued
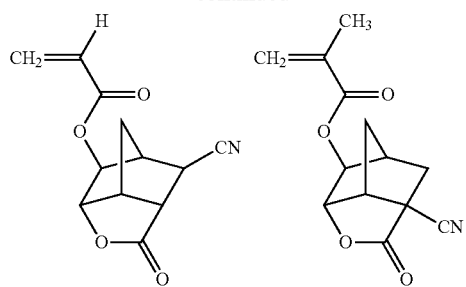
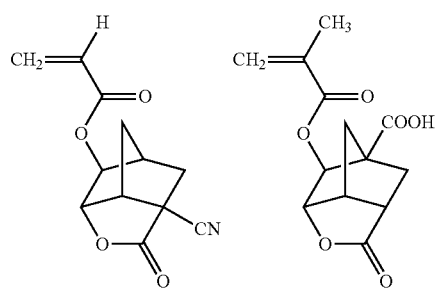
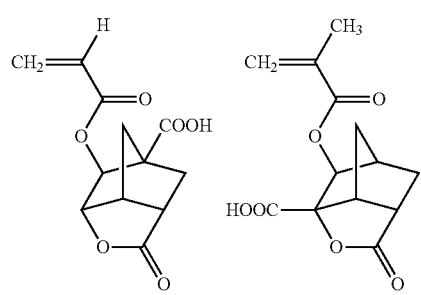
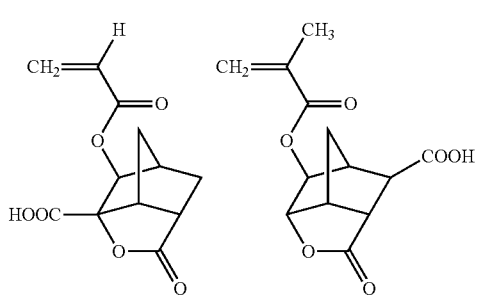
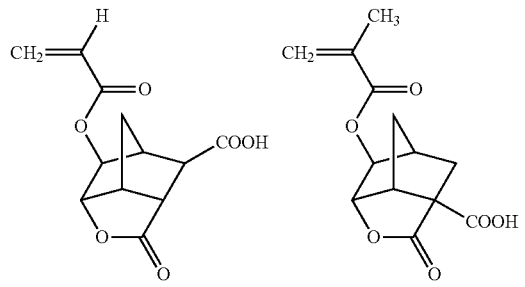
-continued
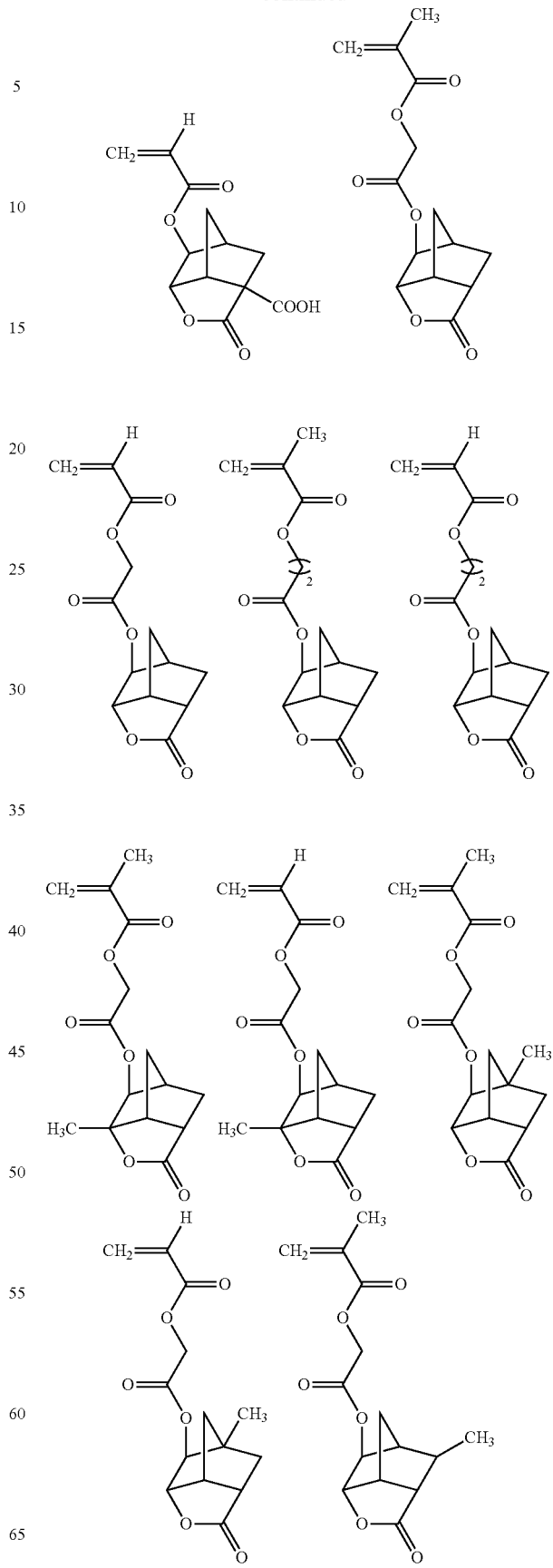

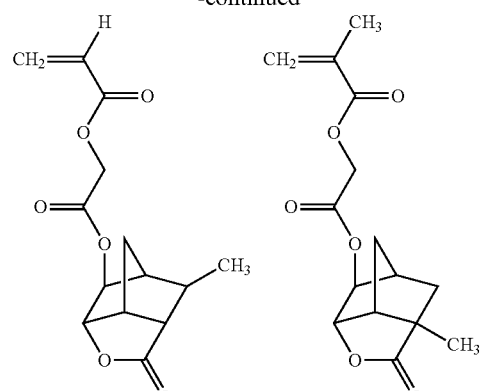
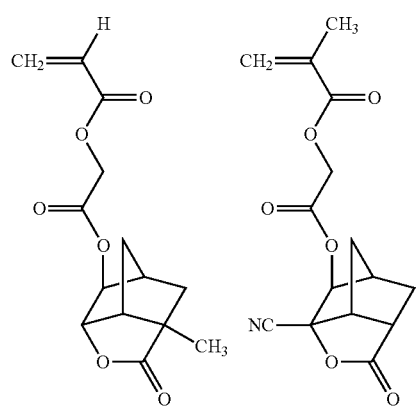
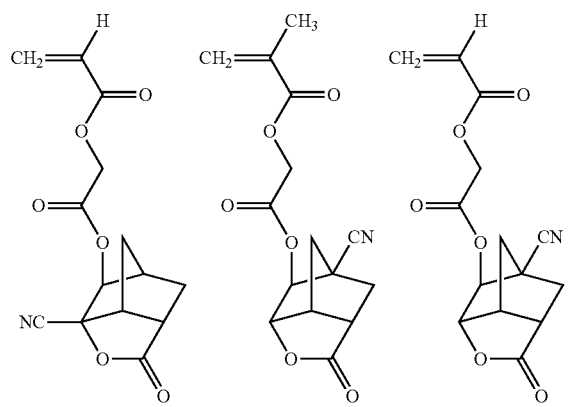
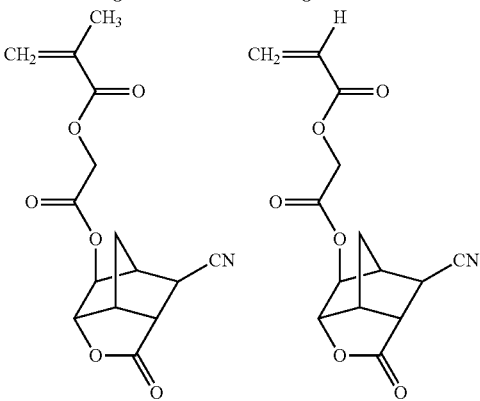
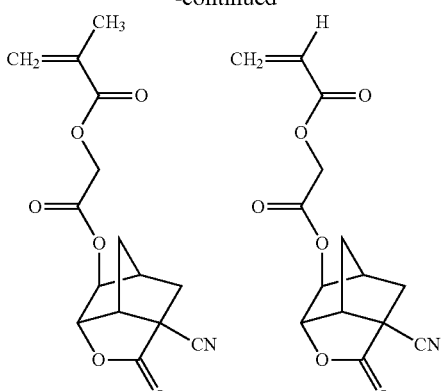
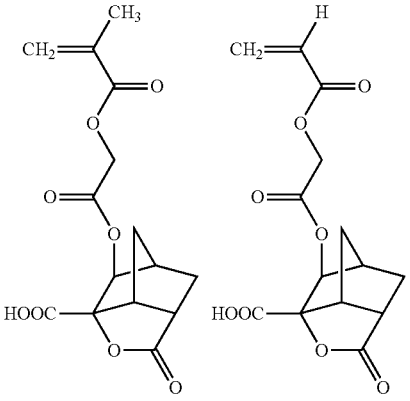
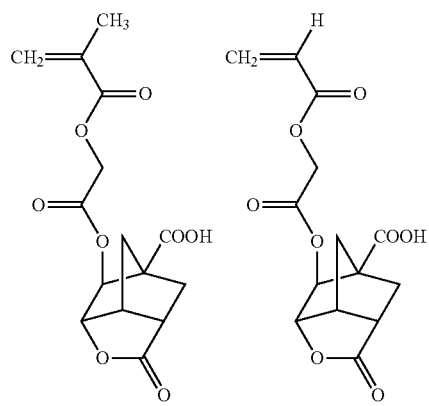
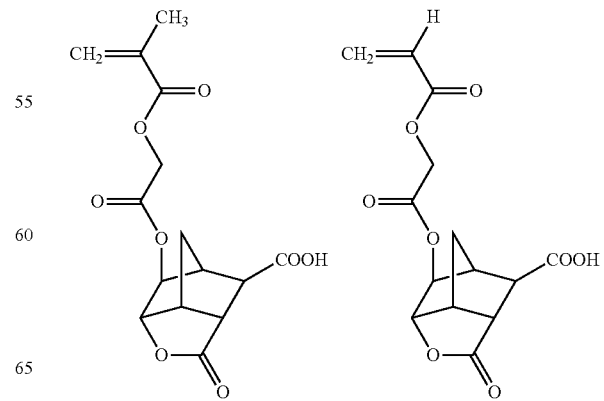

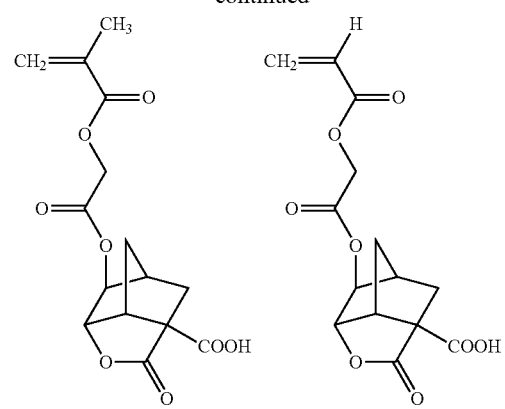
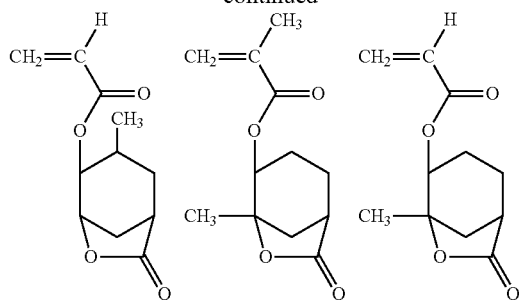
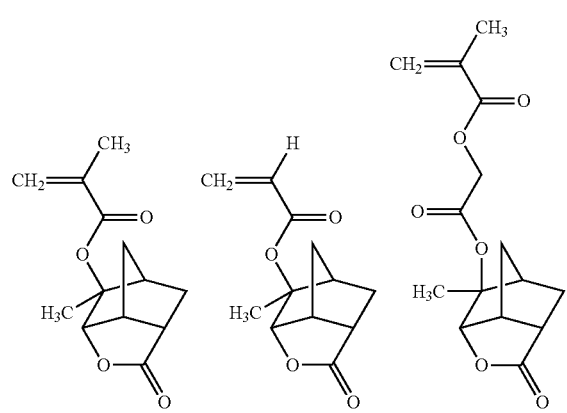
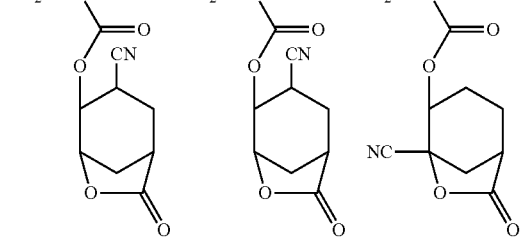
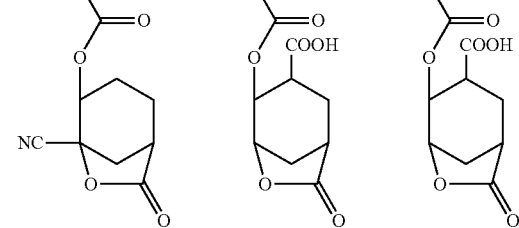
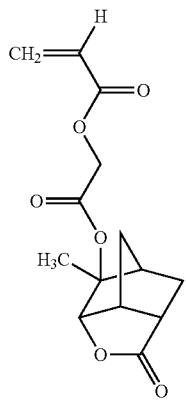
Examples of the monomer represented by the formula (a3-3) include the followings.
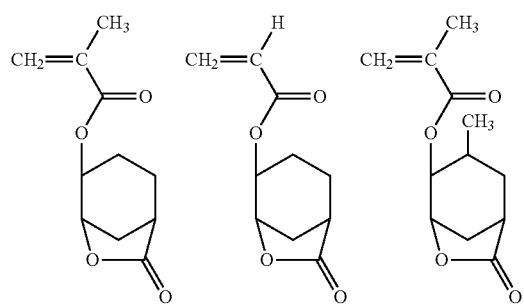
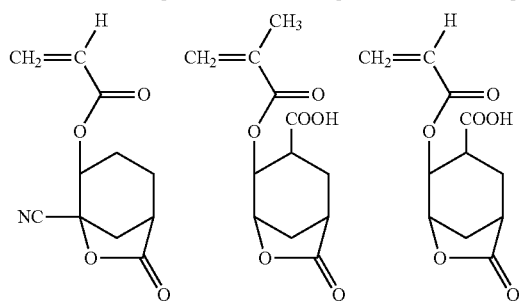
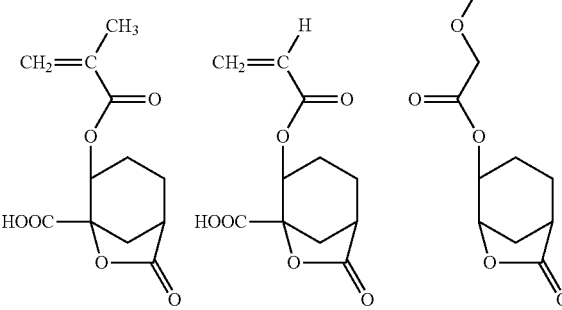
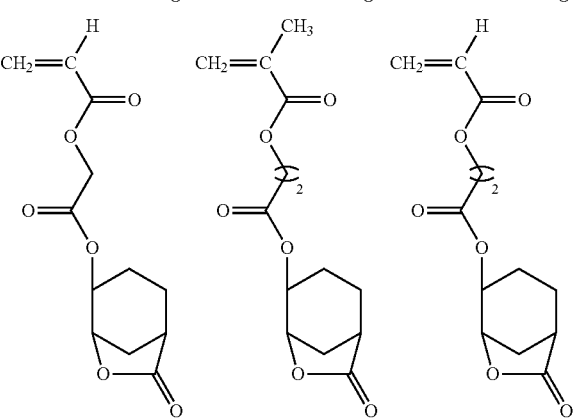

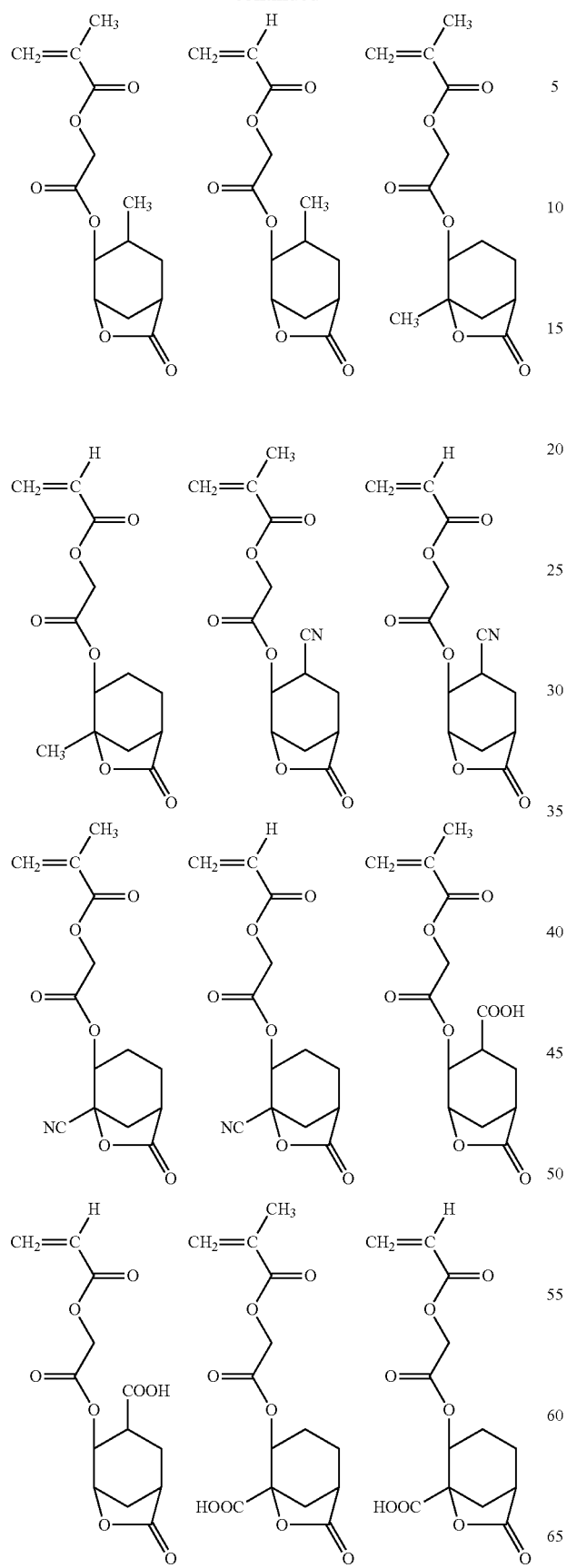
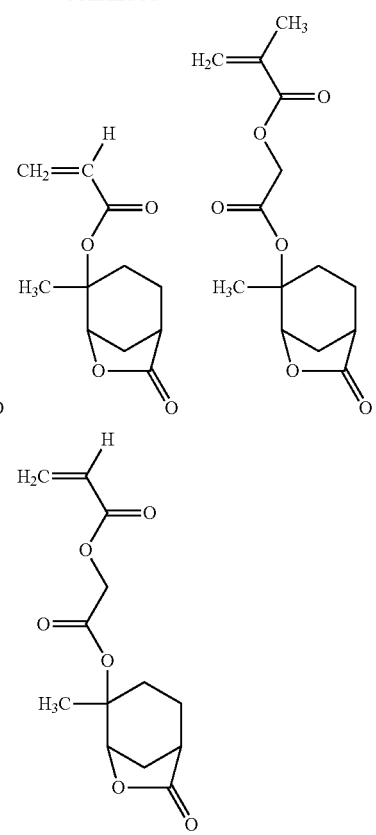

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of the resin.

Examples of the other monomer having no acid-labile group include the monomers represented by the formulae (a-4-1), (a-4-2) and (a-4-3):

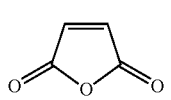

(a4-1)

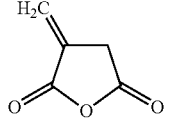

(a4-2)

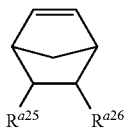

(a4-3)

wherein $R^{a25}$ and $R^{a26}$ each independently represents a hydrogen atom, a C1-C3 aliphatic hydrocarbon group which can have one or more substituents, a carboxyl group, a cyano group or a —COOR$^{a27}$ group in which $R^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of —COO— of R$^{a27}$ is not a tertiary carbon atom, or $R^{a25}$ and $R^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by R$^{a27}$ is preferably a C1-C8 aliphatic hydrocarbon group and is more preferably a C1-C6 aliphatic hydrocarbon group. The C3-C36 saturated cyclic hydrocarbon group represented by R$^{a27}$ is preferably a C4-C36 saturated cyclic hydrocarbon group, and is more preferably C4-C12 saturated cyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a-4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a-4-1), (a-4-2) or (a-4-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,000 or more of the weight-average molecular weight, preferably 2,500 or more of the weight-average molecular weight, and more preferably 3,000 or more of the weight-average molecular weight. The resin usually has 30,000 or less of the weight-average molecular weight, preferably has 15,000 or less of the weight-average molecular weight, more preferably 9,000 or less of the weight-average molecular weight and especially preferably 6,000 or less of the weight-average molecular weight. The weight-average molecular weight can be measured with gel permeation chromatography.

The first photoresist composition of the present invention usually includes 80% by weight or more of the resin based on sum of solid component. In this specification, "solid component" means components other than solvent in the first photoresist composition.

The first photoresist composition of the present invention contains an acid generator. The acid generator will be illustrated below.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and DNQ 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonulmethide anion. The onium salt compound is preferable.

Other examples of the acid generator include acid generators described in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712.

A fluorine-containing acid generator is preferable.

Preferable examples of the acid generator include a salt represented by the formula (B1):

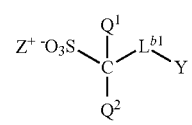

(B1)

wherein $Q^1$ and $Q^2$ each independently represent a fluorine atom or a C1-C6 perfluoroalkyl group,
$L^{b1}$ represents a single bond or a C1-C17 saturated divalent hydrocarbon group which can have one or more substituents, and one or more methylene groups in the saturated divalent hydrocarbon group can be replaced by —O— or —CO—,
Y represents a C1-C18 aliphatic hydrocarbon group or a C3-C18 saturated cyclic hydrocarbon group, and the aliphatic hydrocarbon group and the saturated cyclic hydrocarbon group can have one or more substituents, and one or more methylene groups in the aliphatic hydrocarbon group and the saturated cyclic hydrocarbon group can be replaced by —O—, —CO— or —SO$_2$—, and
$Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated divalent hydrocarbon group include a C1-C17 alkylene group and a divalent group having an alicyclic divalent hydrocarbon group. Examples of the alkylene group include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a branched chain alkanediyl group formed by replacing one or more hydrogen atom of the above-mentioned linear alkanediyl group by a C1-C4 alkyl group, and a divalent group having an alicyclic divalent hydrocarbon group such as the following groups represented by the formulae ($X^1$-A) to ($X^1$-C):

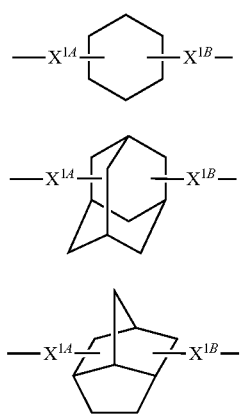

($X^1$-A)

($X^1$-B)

($X^1$-C)

wherein $X^{1A}$ and $X^{1B}$ independently each represent a C1-C6 alkylene group which can have one or more substituents, with the proviso that total carbon number of the group represented by the formula ($X^1$-A), ($X^1$-B) or ($X^1$-C) is 1 to 17.

One or more methylene groups in the C1-C6 alkylene group can be replaced by —O— or —CO—.

Examples of the C1-C17 saturated hydrocarbon group in which one or more methylene groups are replaced by —O— or —CO— include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 alkanediyl group, $L^{b3}$ represents a single bond or a C1-C12 alkanediyl group, $L^{b4}$ represents a single bond or a C1-C13 alkanediyl group, with proviso that total carbon number of $L^{b3}$ and $L^{b4}$ is 1 to 13, $L^{b5}$ represents a C1-C15 alkanediyl group, $L^{b6}$ represents a C1-C15 alkanediyl group, $L^{b7}$ represents a C1-C15 alkanediyl group, with proviso that total carbon number of $L^{b6}$ and $L^{b7}$ is 1 to 16, $L^{b8}$ represents a C1-C14 alkanediyl group, $L^{b9}$ represents a C1-C11 alkanediyl group, $L^{b10}$ represents a C1-C11 alkanediyl group, with proviso that total carbon number of $L^{b9}$ and $L^{b10}$ is 1 to 12, and * represents a binding position to —C($Q^1$) ($Q^2$)-. Among them, preferred are *—CO—O-$L^{b2}$-, *—CO—O-$L^{b4}$-CO—-$L^{b3}$-, *-$L^{b5}$-O—CO— and *-$L^{b7}$-O-$L^{b6}$-, and more preferred are *—CO—O-$L^{b2}$- and *—CO—O-$L^{b4}$-CO—O-$L^{b3}$-, and much more preferred is *—CO—O-$L^{b2}$-, and especially preferred is *—CO—O-$L^{b2}$-in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, *—CO—O—$(CH_2)_2$—CO—O—, *—CO—O—$(CH_2)_3$—CO—O—, *—CO—O—$(CH_2)_4$—CO—O—, *—CO—O—$(CH_2)_6$—CO—O—, *—CO—O—$(CH_2)_8$—CO—O—, *—CO—O—$CH_2$—CH($CH_3$)—CO—O— and *—CO—O—$CH_2$—C($CH_3$)$_2$—CO—O—. Examples of *-$L^{b5}$-O—CO— include *—$CH_2$—O—CO—, *—$(CH_2)_2$—O—CO—, *—$(CH_2)_3$—O—CO—, *—$(CH_2)_4$—O—CO—, *—$(CH_2)_6$—O—CO— and *—$(CH_2)_8$—O—CO—. Examples of *-$L^{b7}$-O-$L^{b6}$- include *—$CH_2$—O—$CH_2$—. Examples of *—CO—O-$L^{b8}$-O— include *—CO—O—$CH_2$—O—, *—CO—O—$(CH_2)_2$—O—, *—CO—O—$(CH_2)_3$—O—, *—CO—O—$(CH_2)_4$—O— and *—CO—O—$(CH_2)_6$—O—. Examples of *—CO—O-$L^{b10}$-O-$L^{b9}$-CO—O— include the followings.

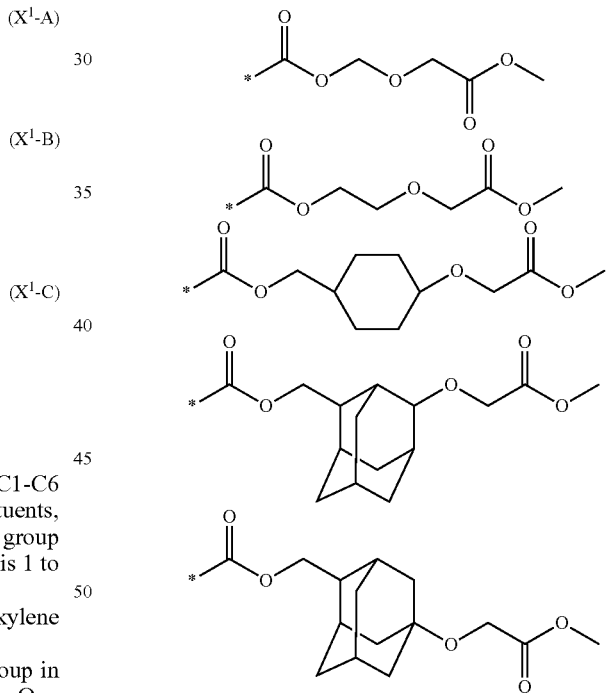

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —$(CH_2)_{j2}$—O—CO—$R^{b1}$— in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 saturated cyclic hydrocarbon group represented by Y include the groups represented by the formulae (Y1) to (Y26):

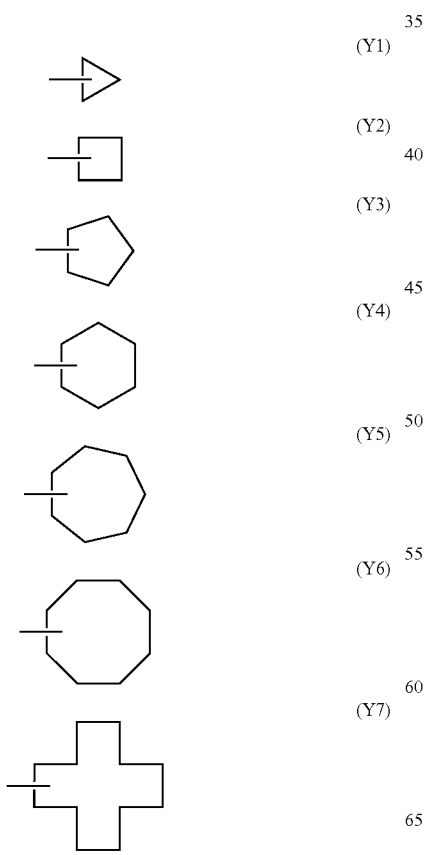

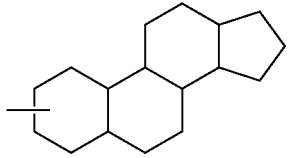

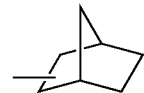

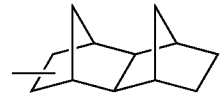

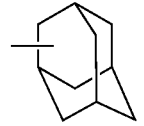

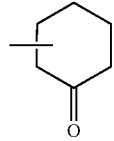

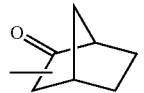

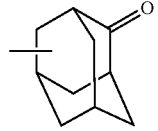

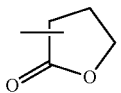

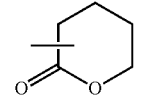

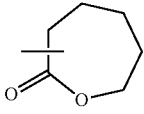

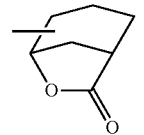

(Y19) 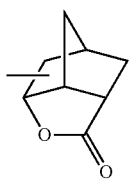

(Y20) 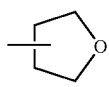

(Y21) 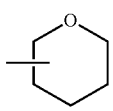

(Y22) 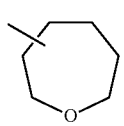

(Y23) 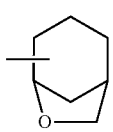

(Y24) 

(Y25) 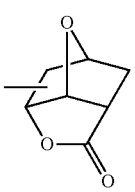

(Y26) 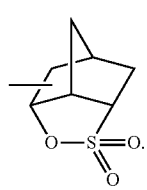

Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.

Examples of Y having one or more substituents include the followings:

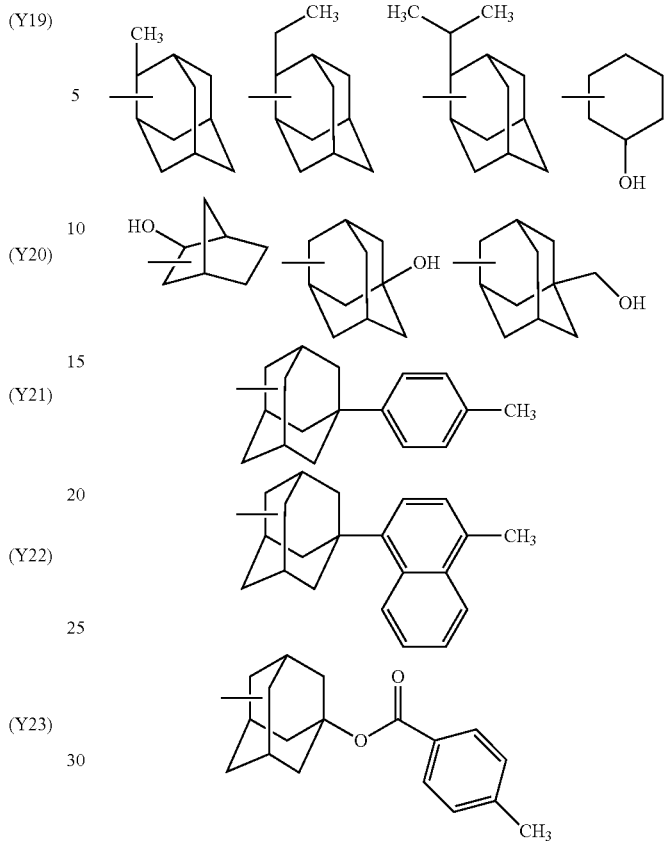

Y is preferably an adamantyl group which can have one or more substituents, and is more preferably an adamantyl group or an oxoadamantyl group.

Among the sulfonic acid anions of the acid generator represented by the formula (B1), preferred is a sulfonic acid anion having the group represented by the above-mentioned formula (b1-1), and more preferred are anions represented by the formulae (b1-1-1) to (b1-1-9).

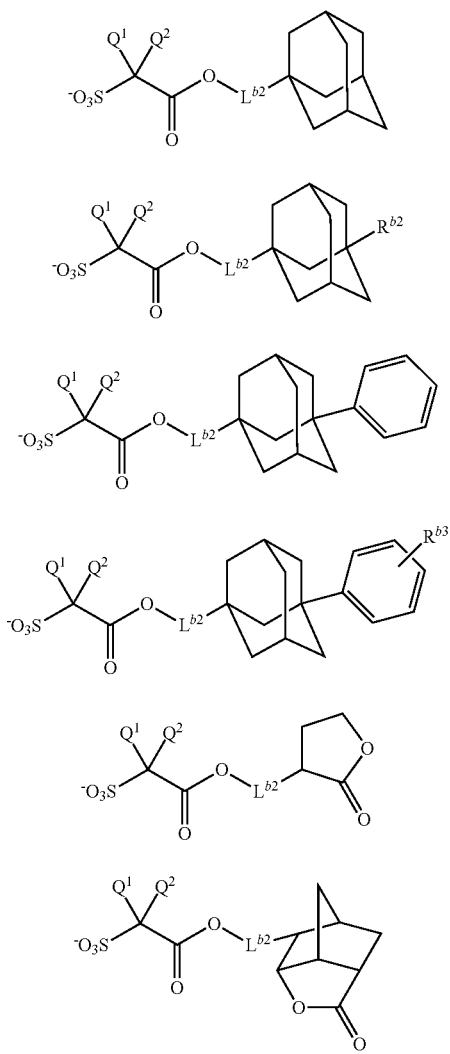
wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.
Specific examples of the sulfonic acid anion include the followings.
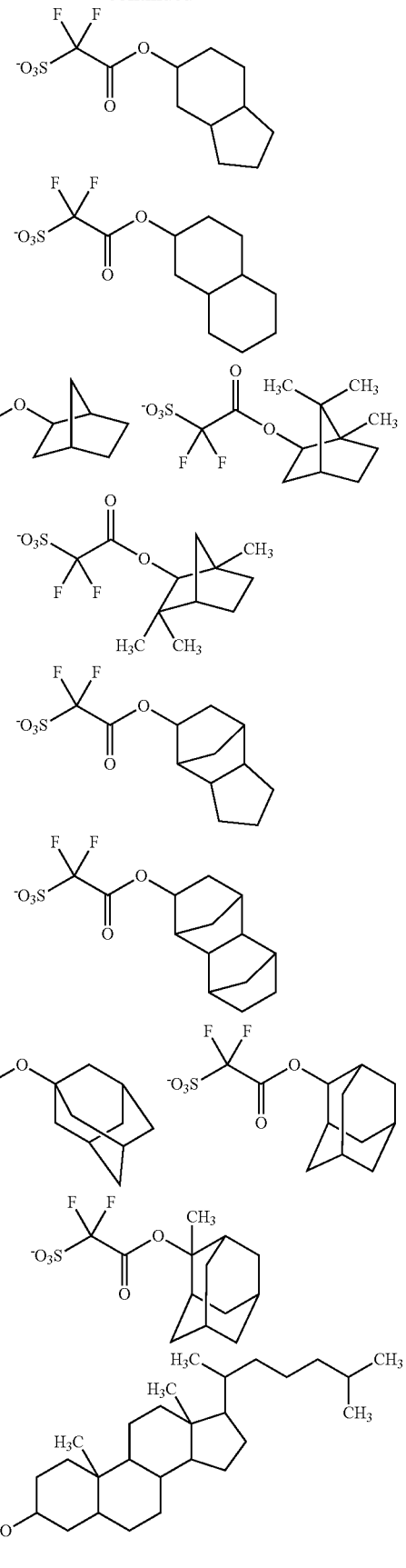

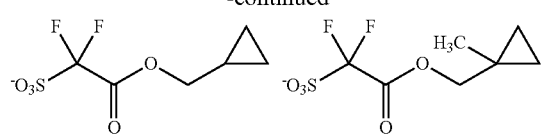
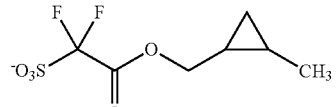
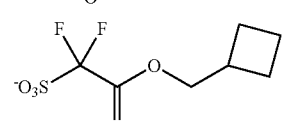
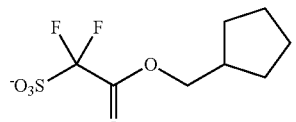
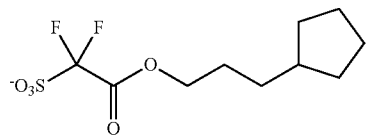
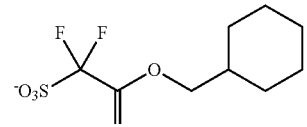
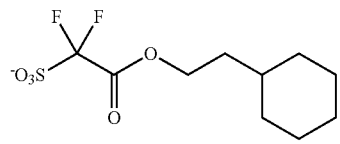
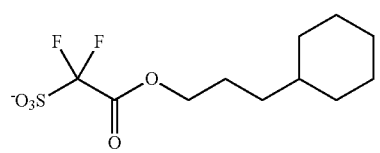
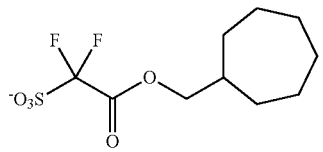
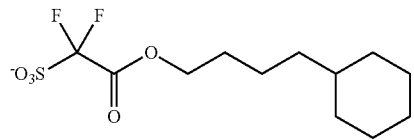
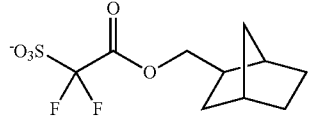
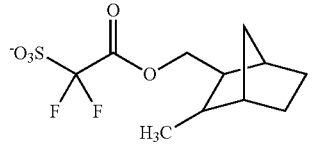
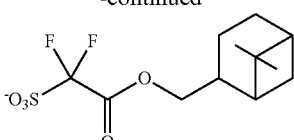
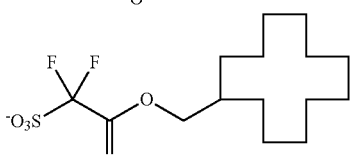
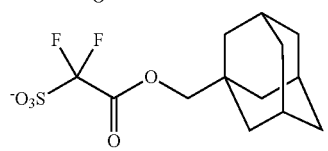
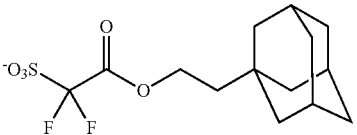
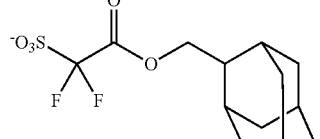
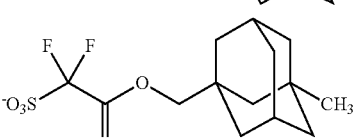
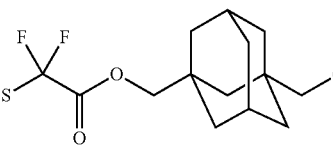
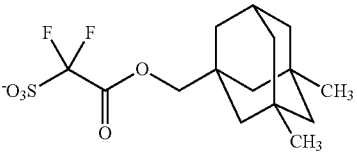
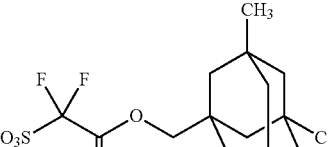
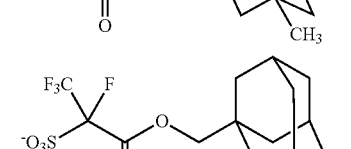
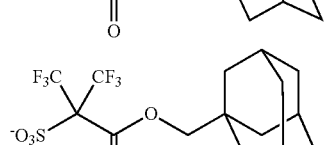

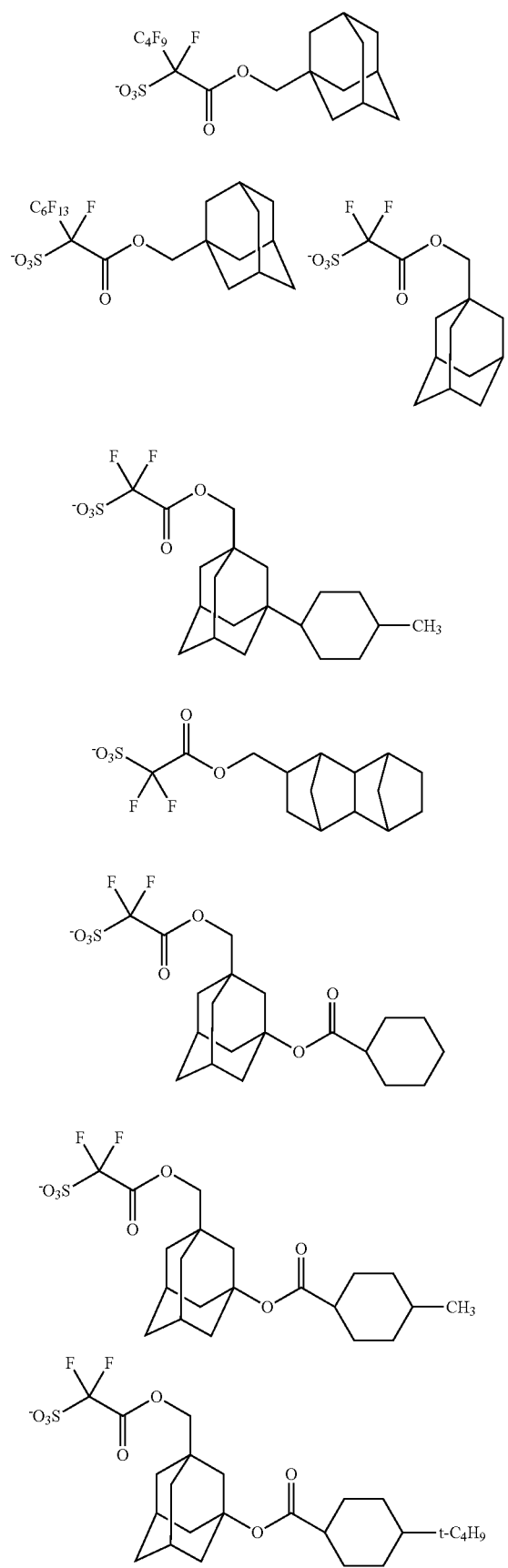
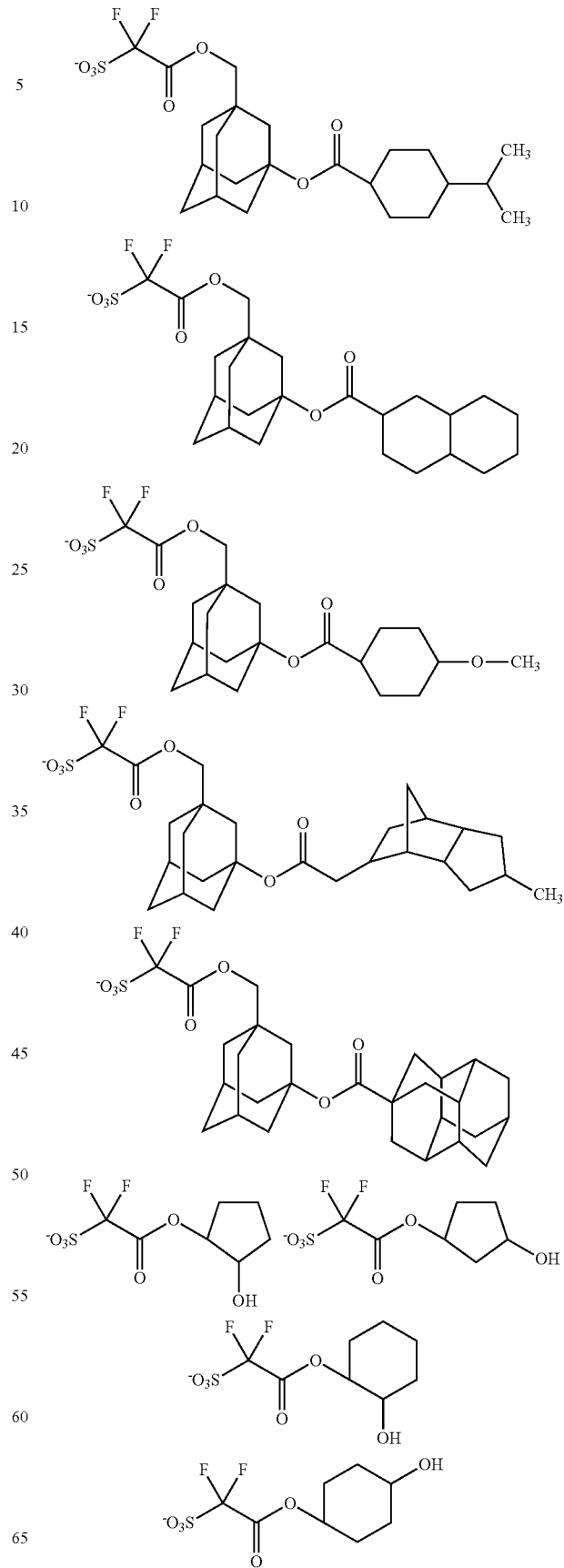

-continued
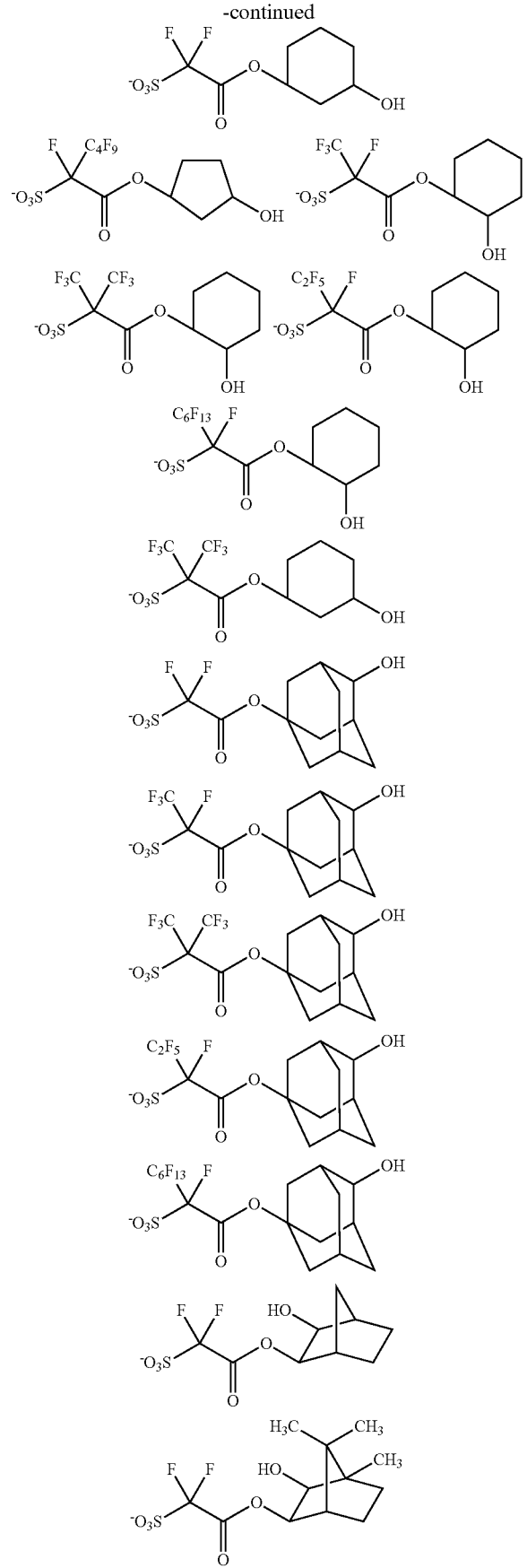
-continued
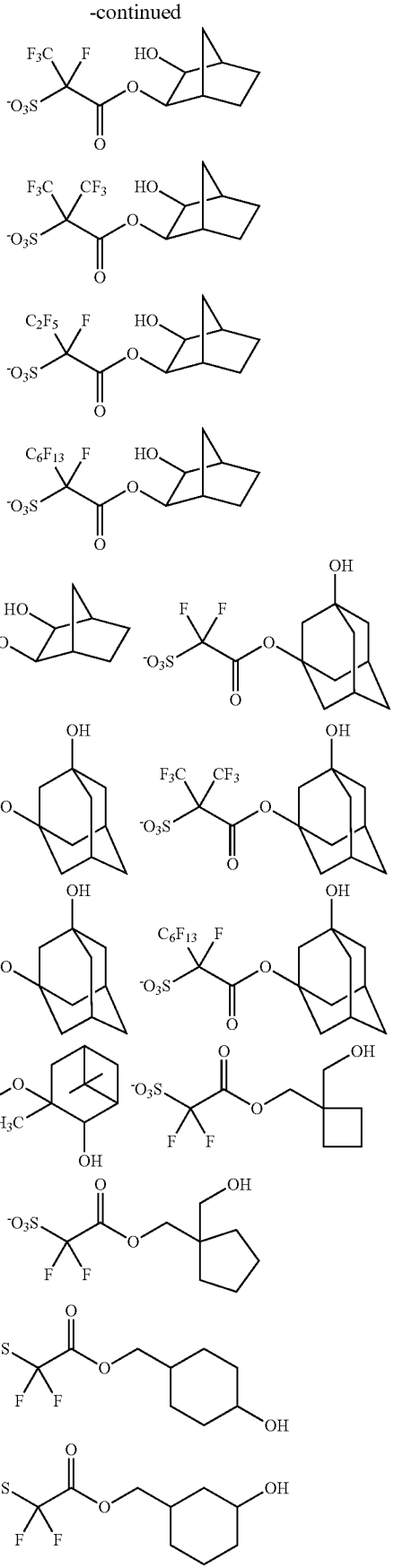

-continued
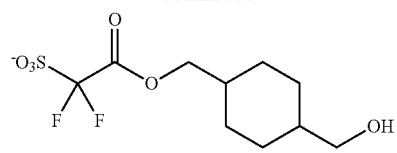
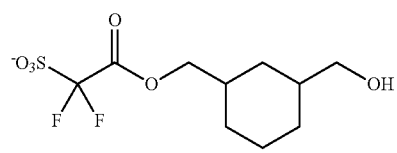
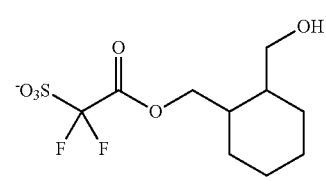
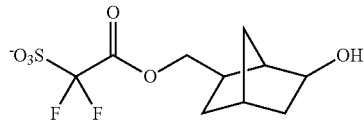
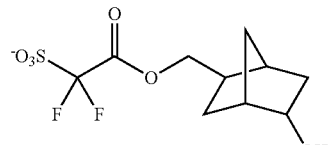
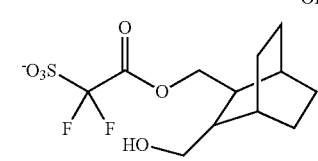
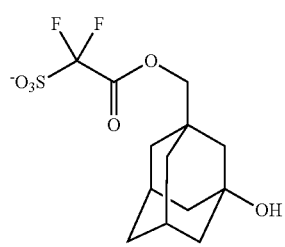
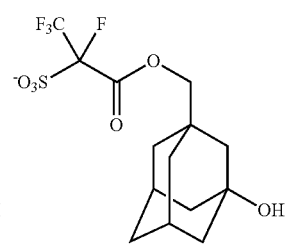
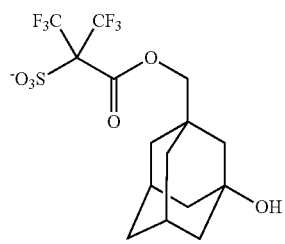
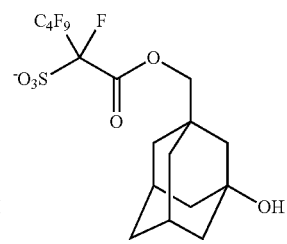
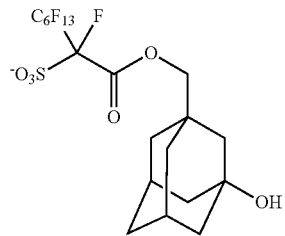
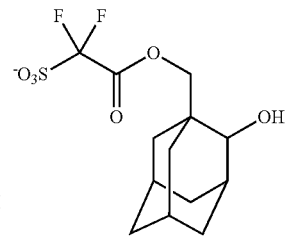
-continued
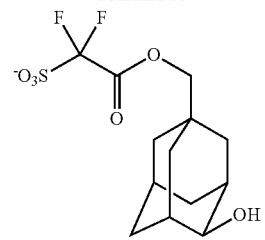
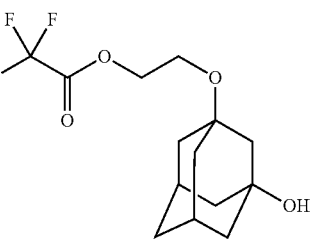
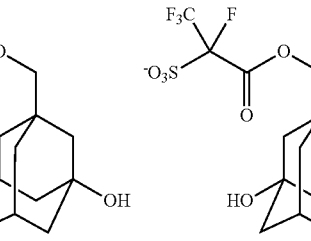
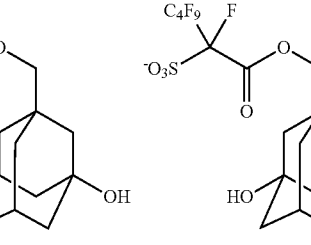
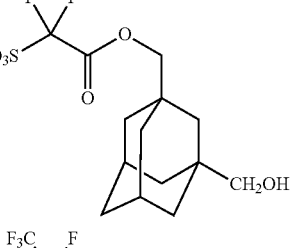
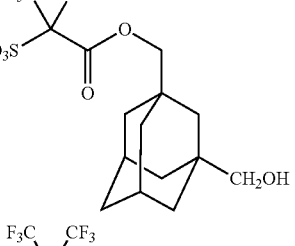
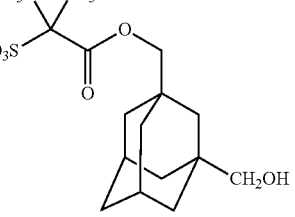

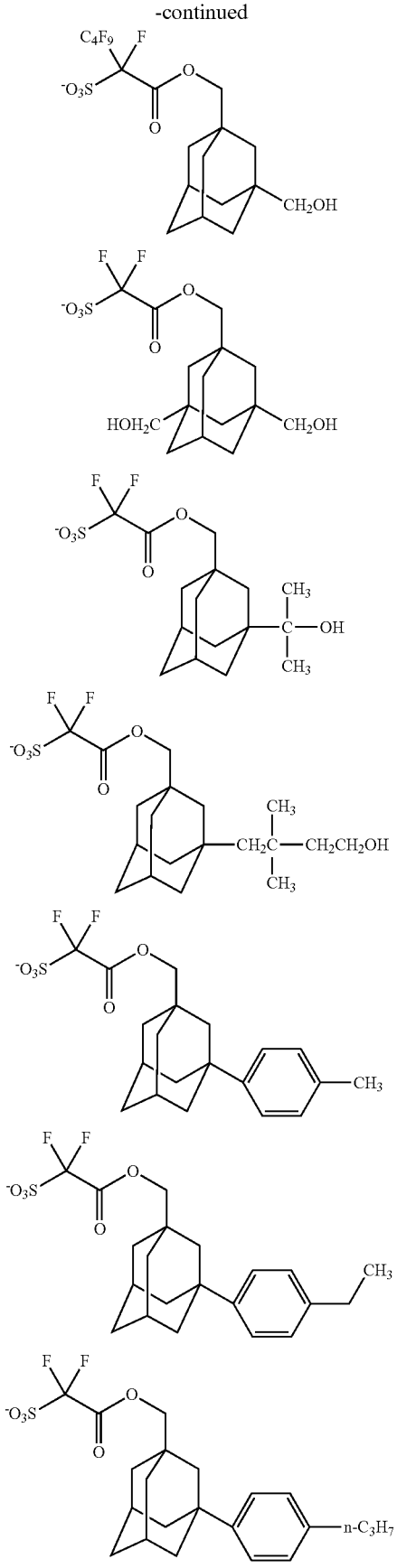
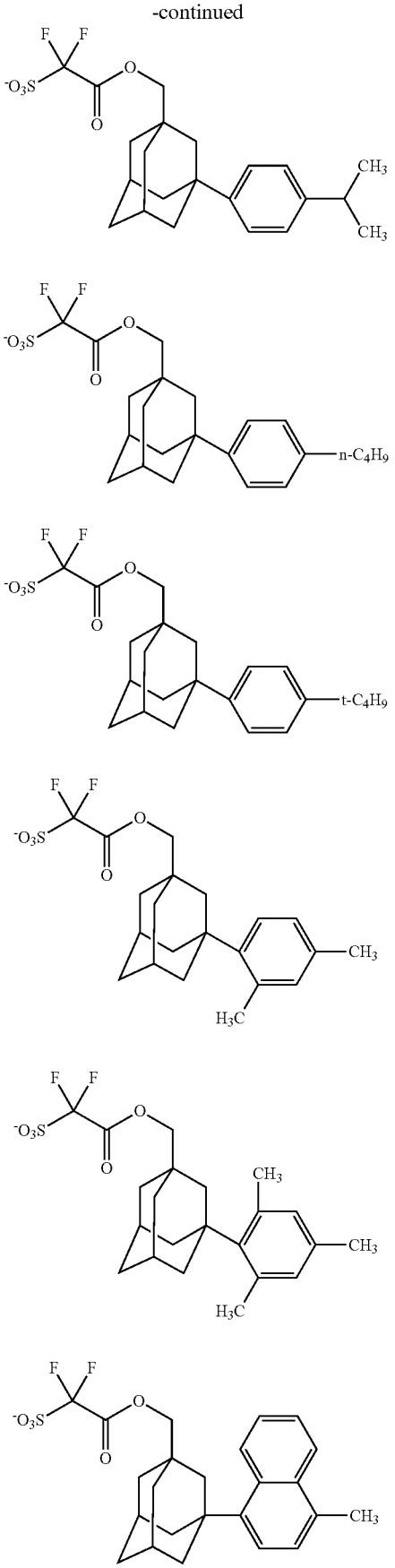

-continued
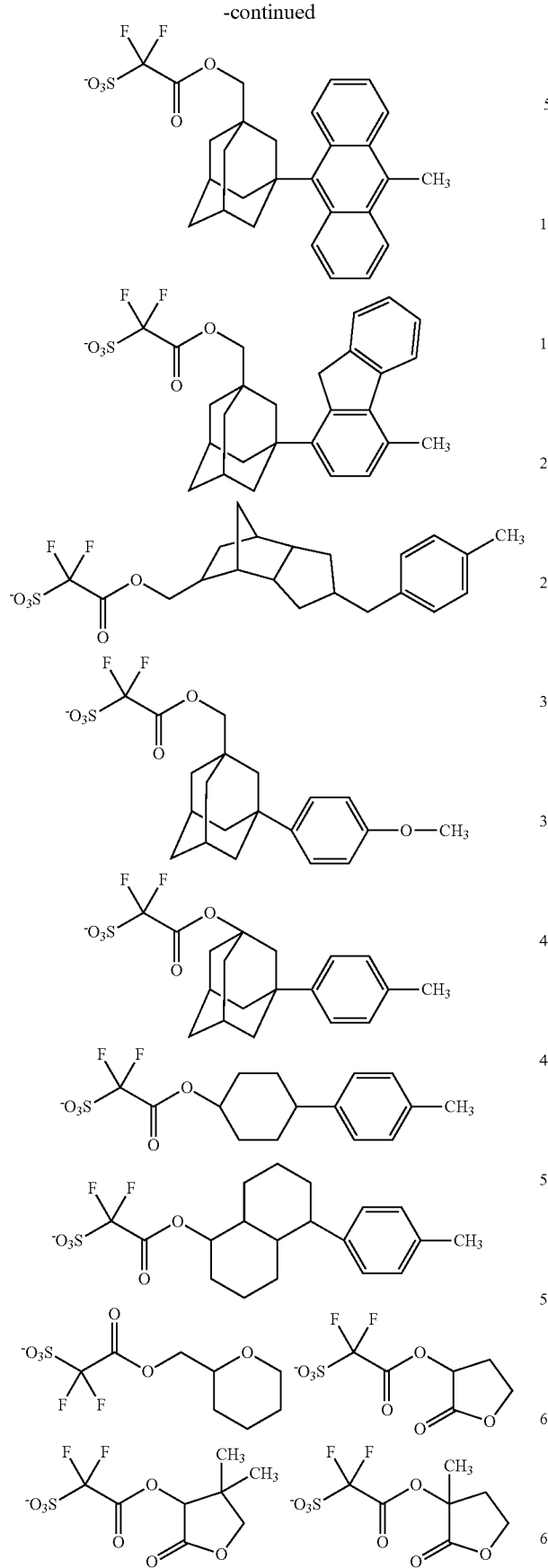
-continued
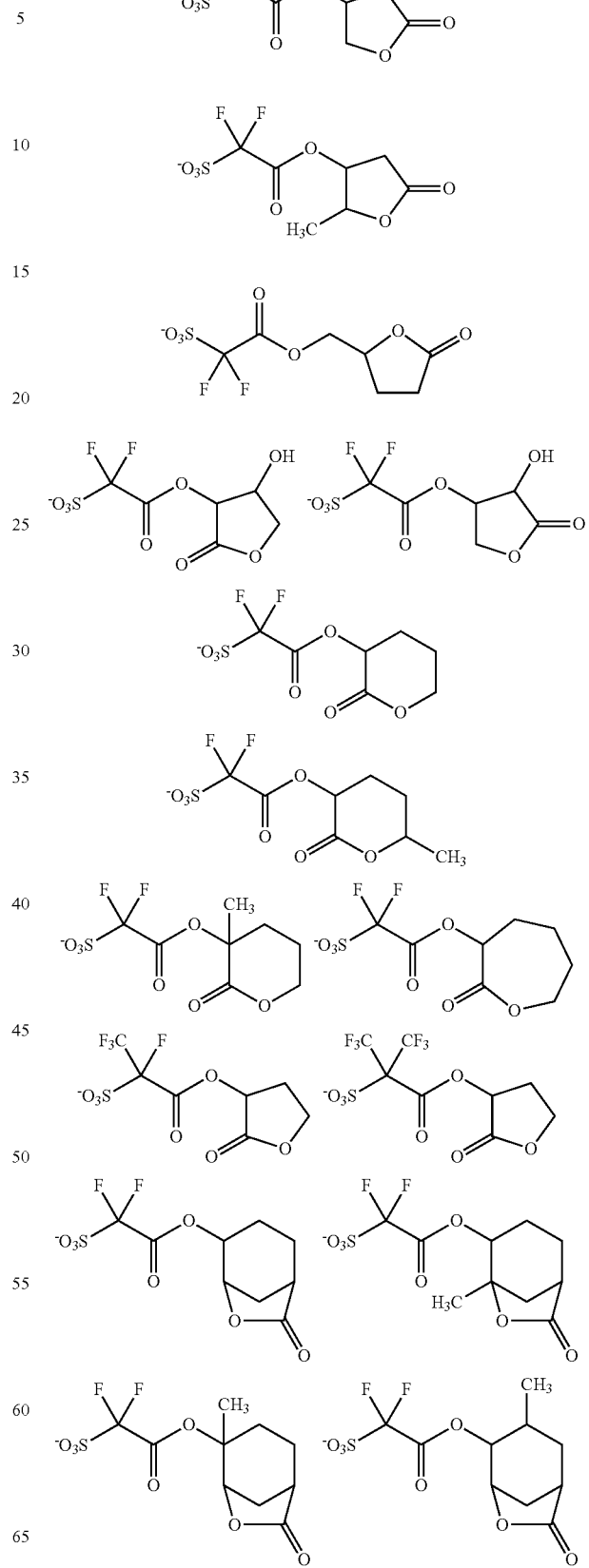

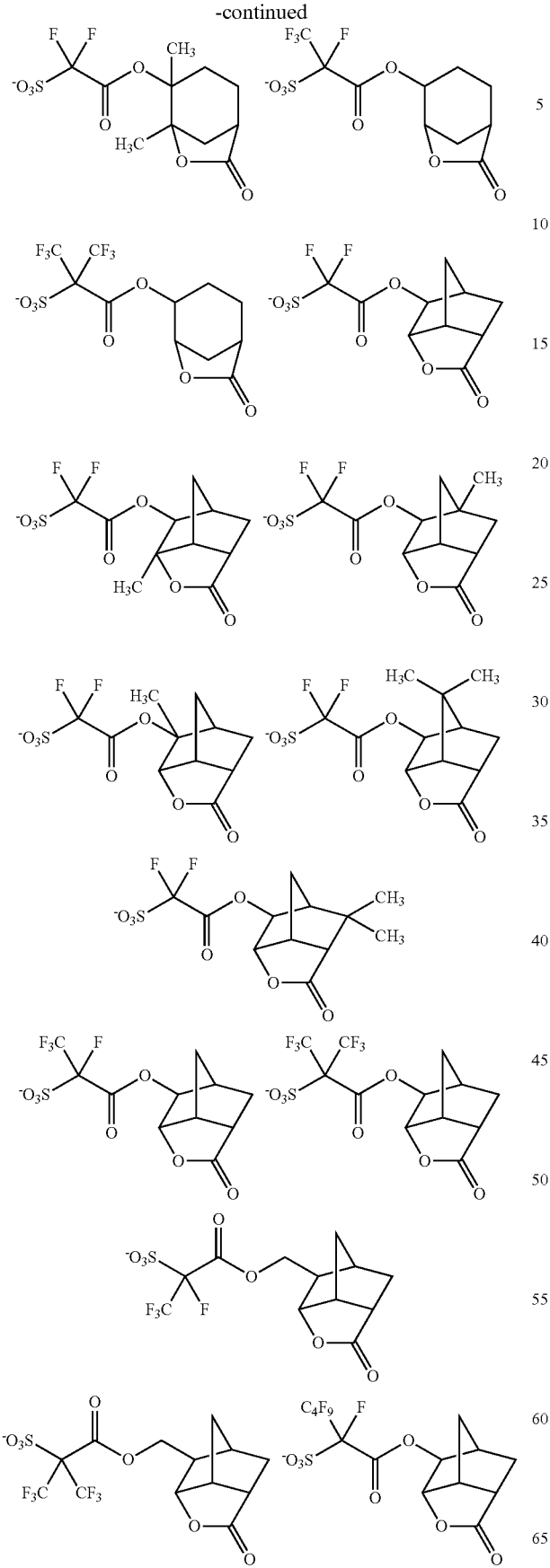
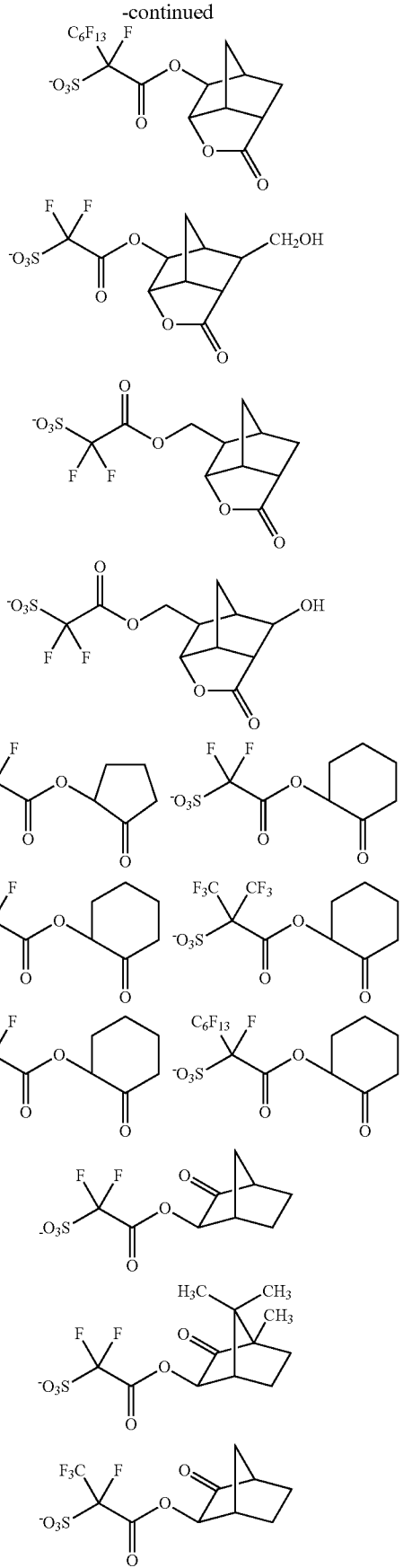

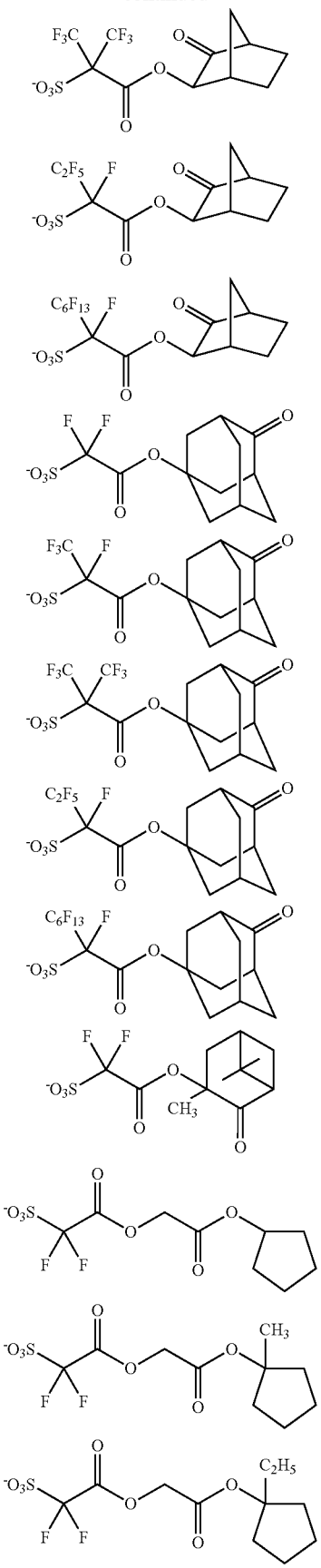
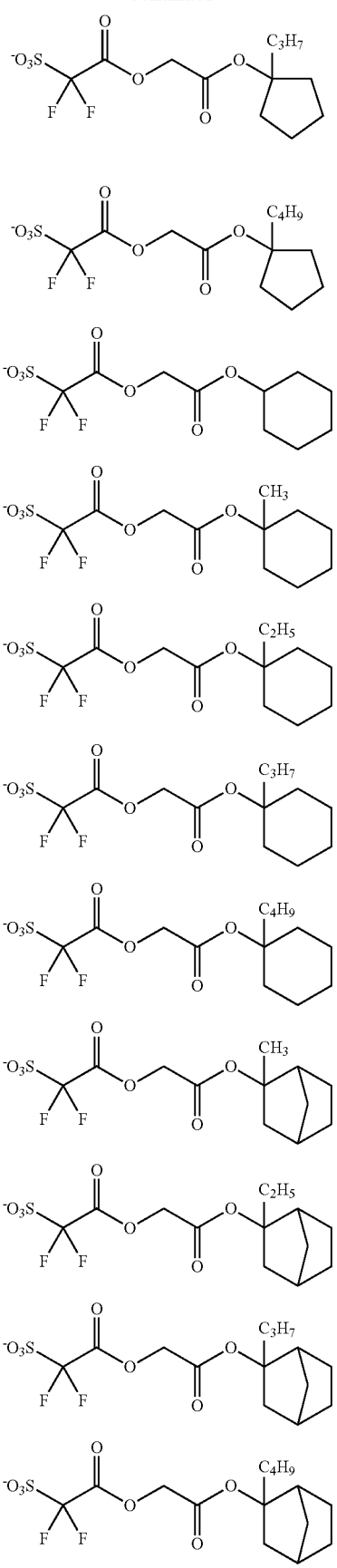

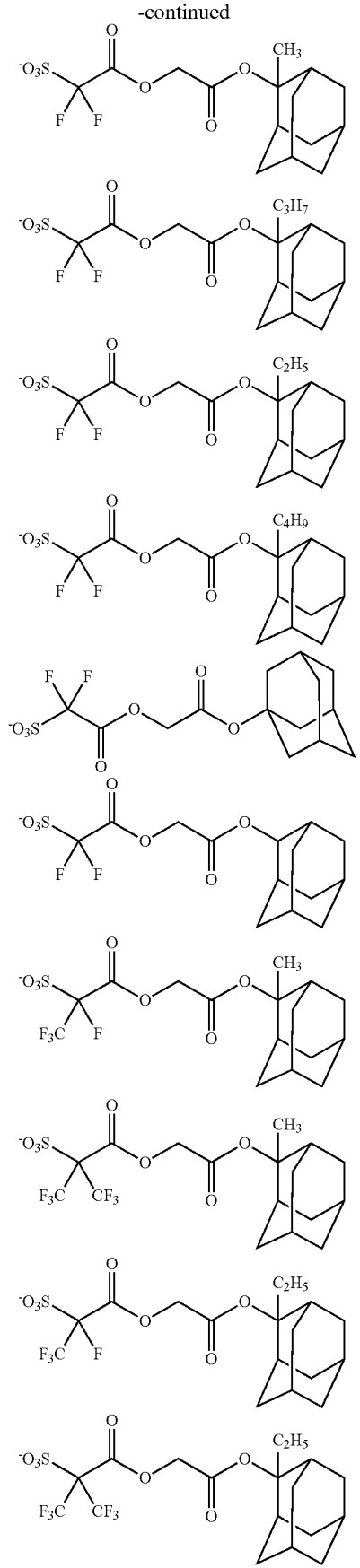

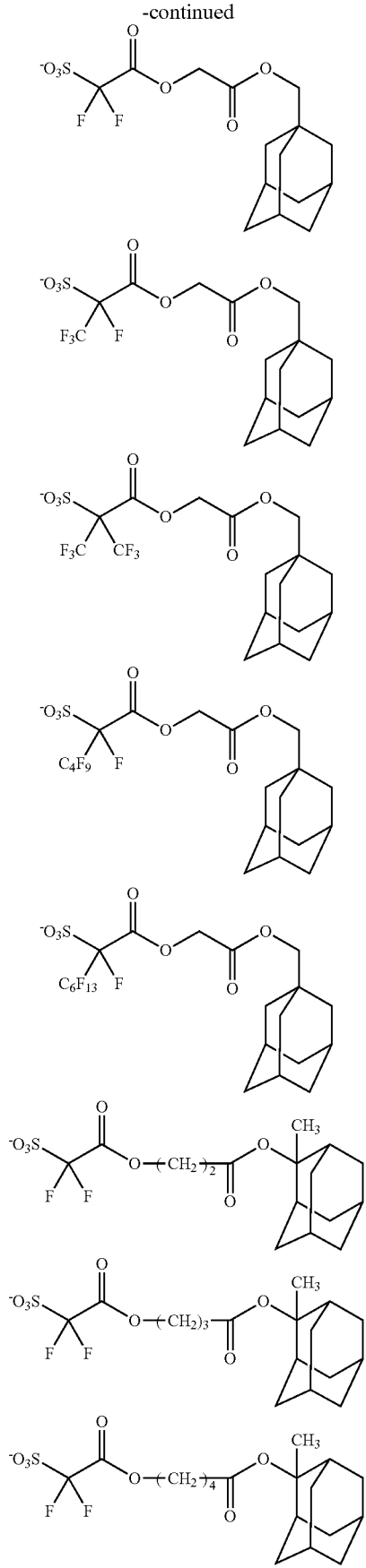
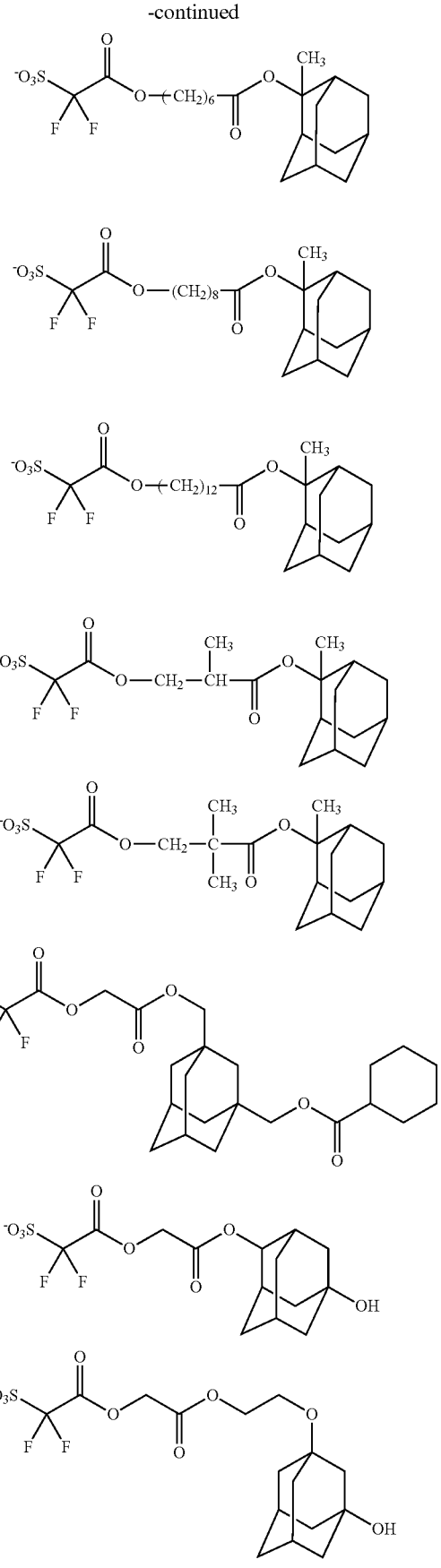

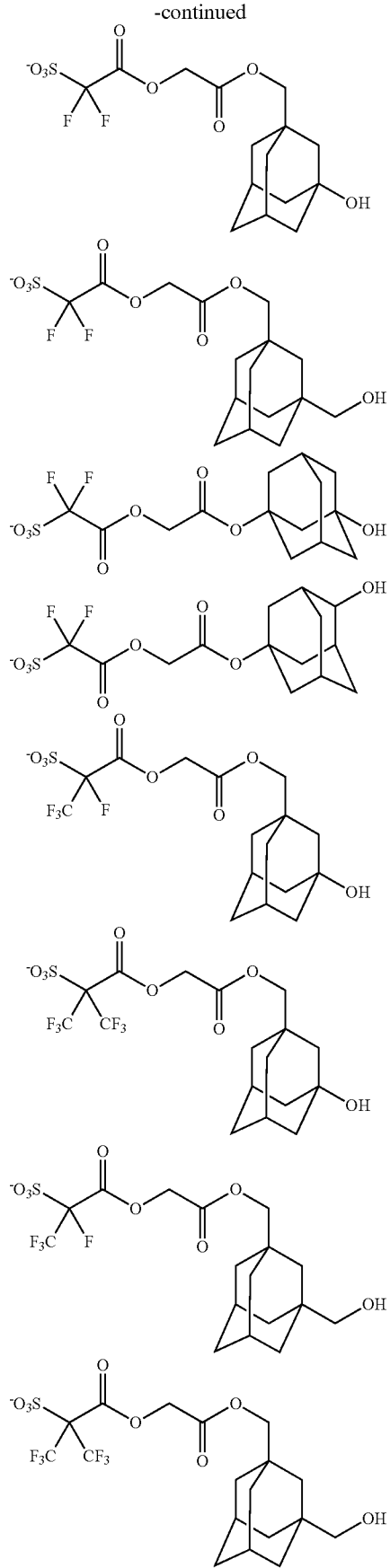
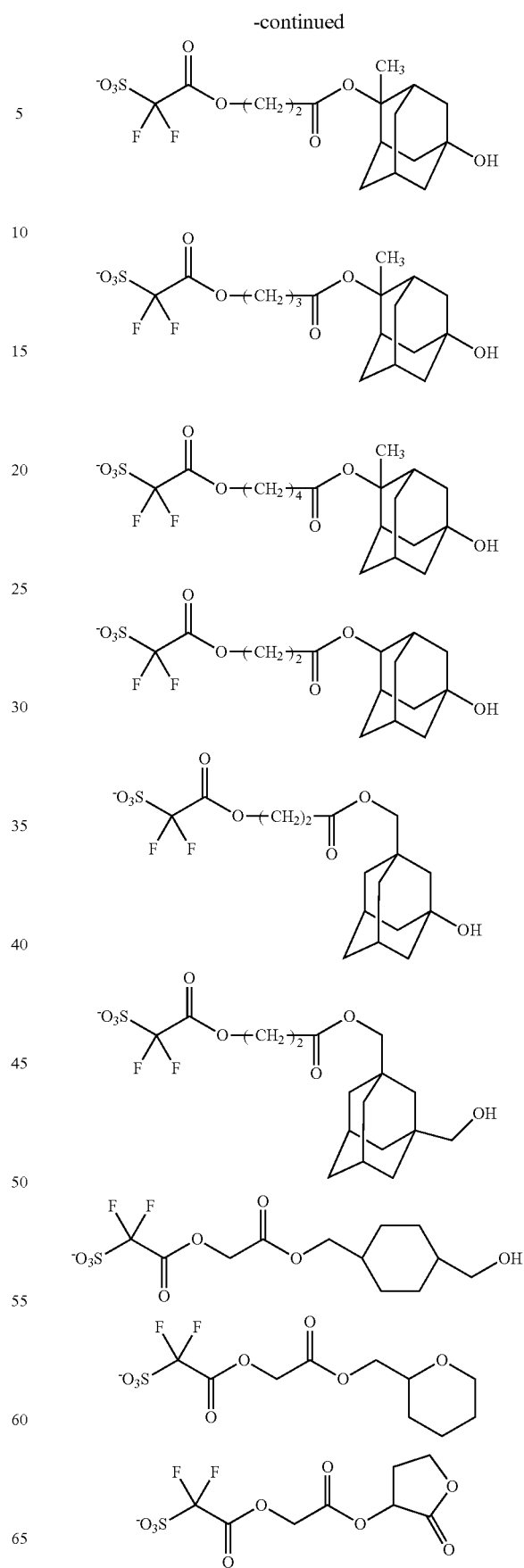

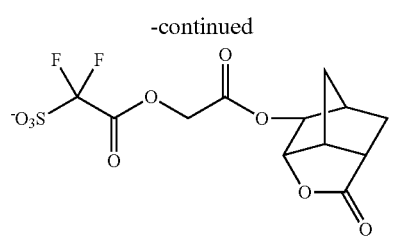
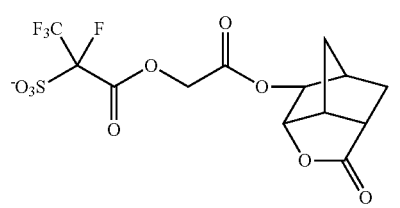
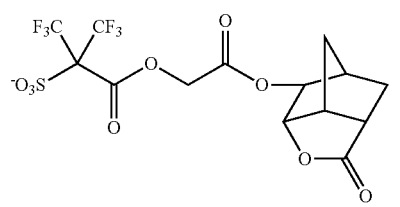
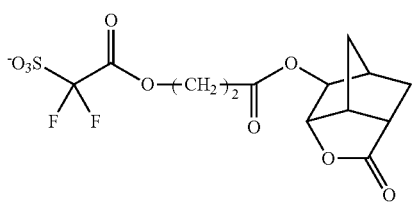
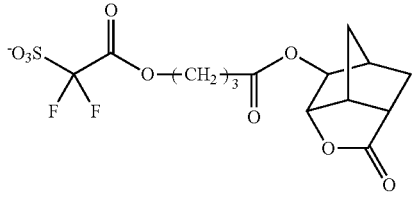
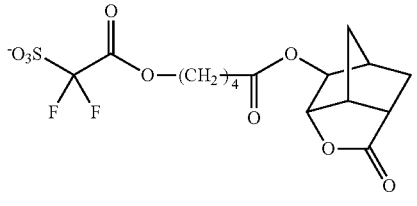
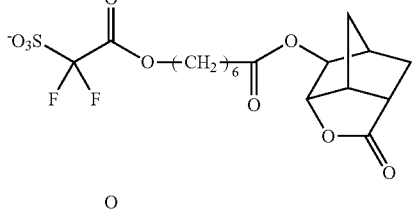
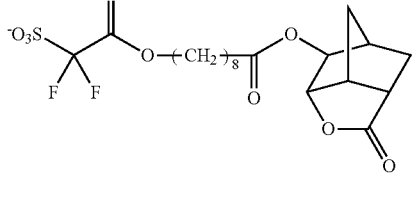
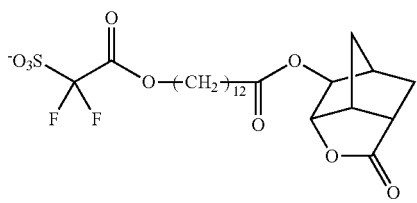
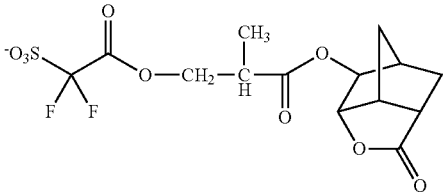
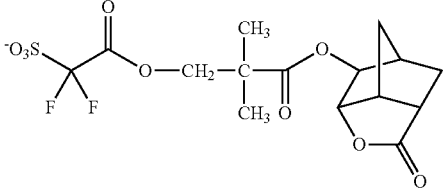
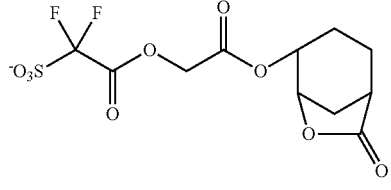
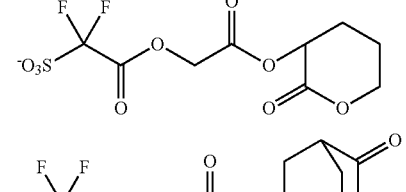
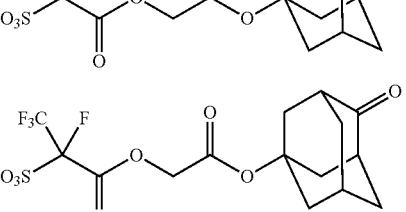
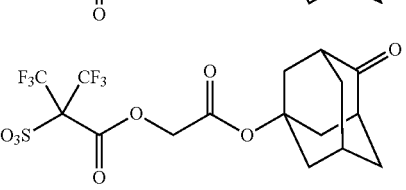
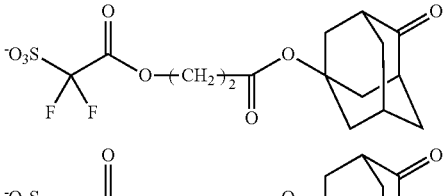
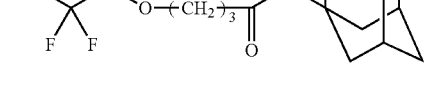

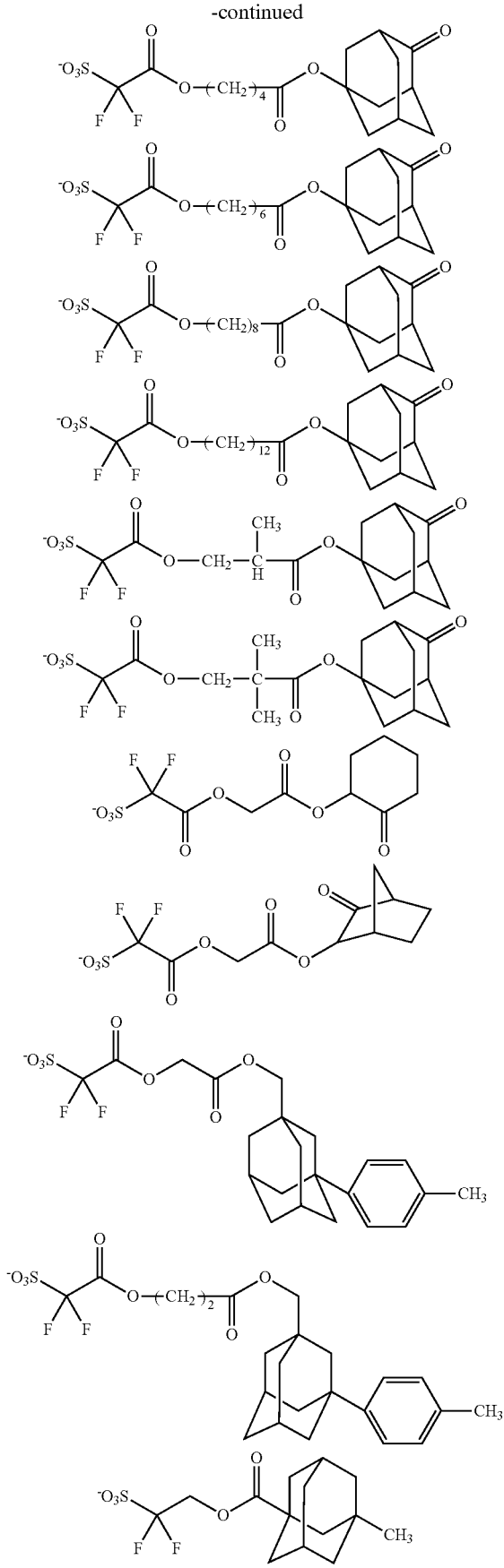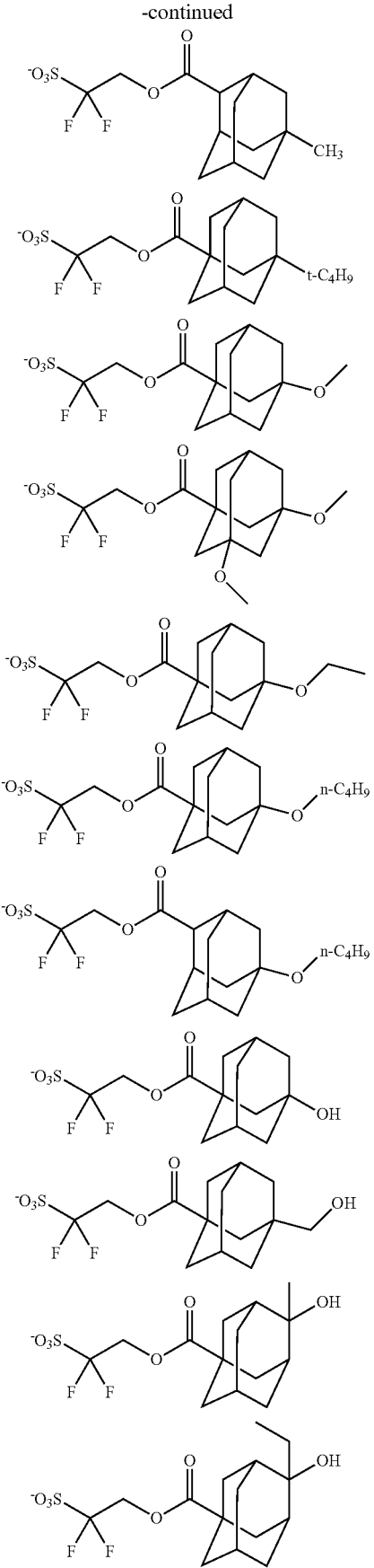

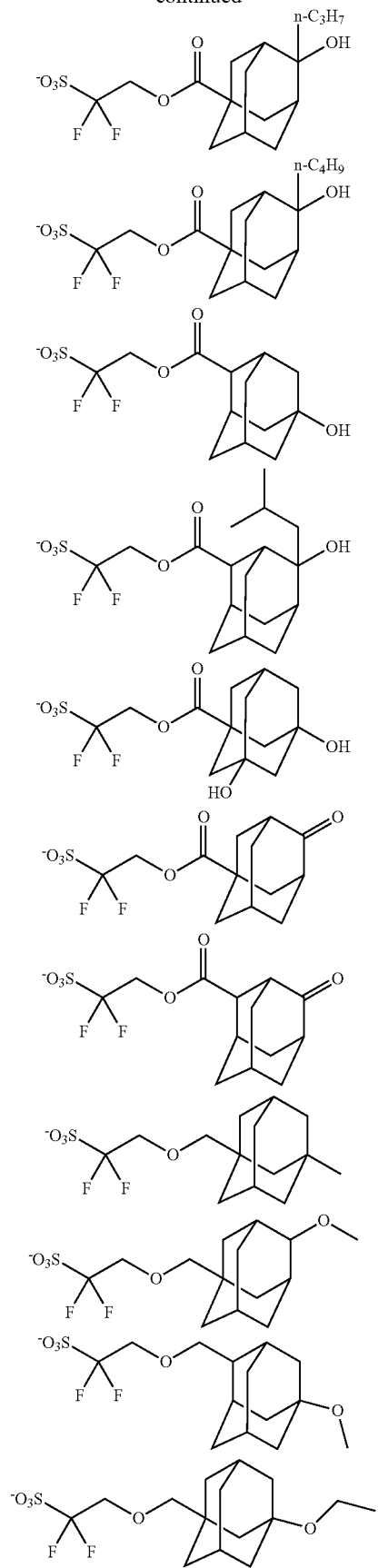
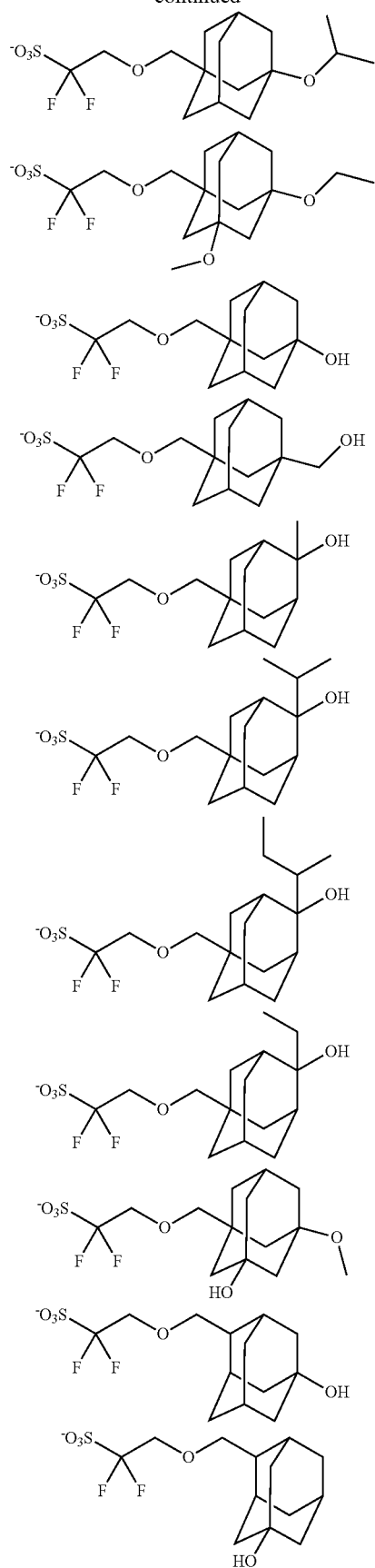

-continued

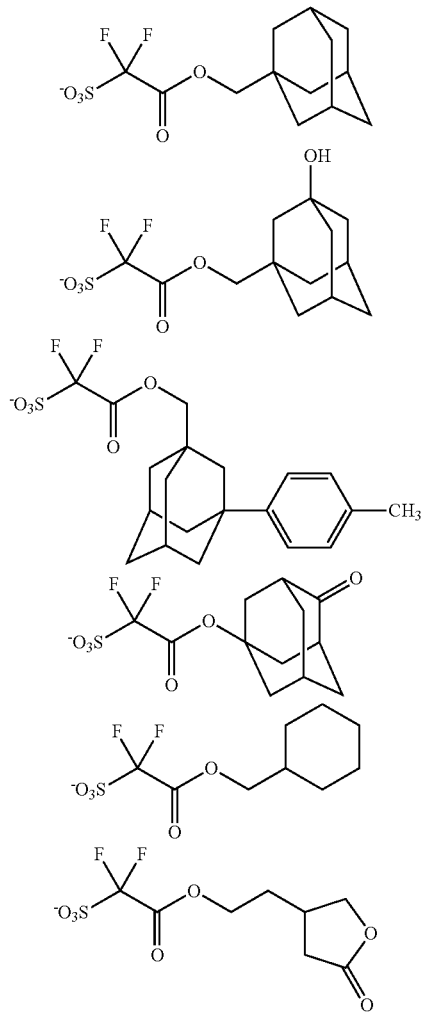

Among them, preferred are the following sulfonic anions.

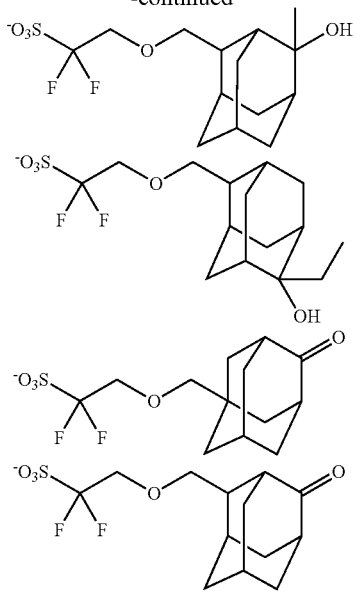

-continued

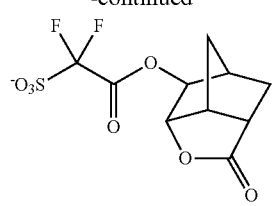

Examples of the cation part represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation part represented by $Z^+$ include the cations represented by the formulae (b2-1) to (b2-4):

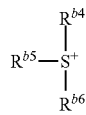

(b2-1)

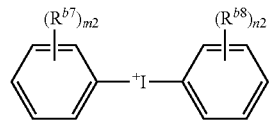

(b2-2)

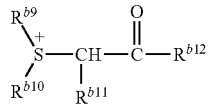

(b2-3)

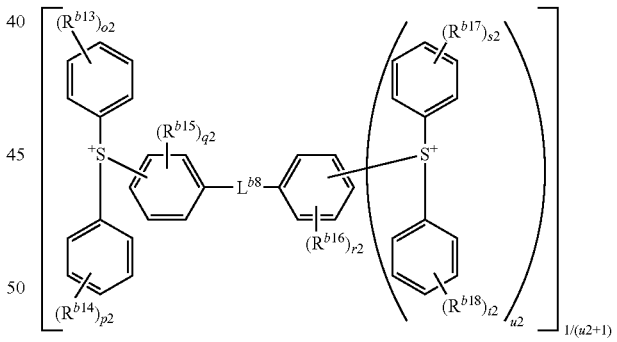

(b2-4)

wherein $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 aliphatic hydrocarbon group, a C3-C36 saturated cyclic hydrocarbon group or a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ each independently represent a C1-C36 aliphatic hydrocarbon group or a C3-C36 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C36 aliphatic hydrocarbon group, a C3-C36 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 36 carbon atoms and more preferably 4 to 12 carbon atoms.

Examples of the aliphatic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. A C4-C12 cyclic aliphatic hydrocarbon group is preferable. Preferable examples of the cyclic aliphatic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

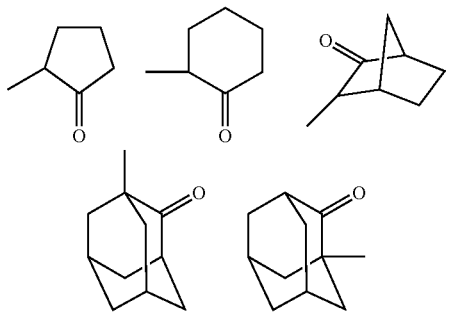

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

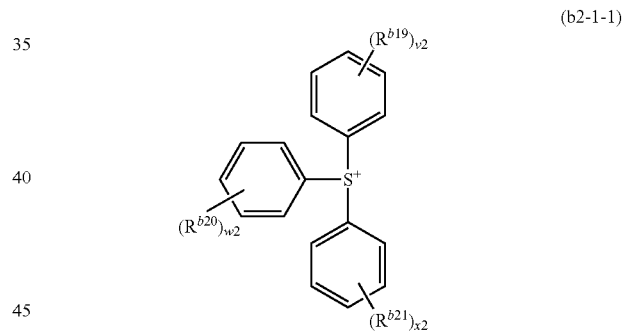

(b2-1-1)

wherein $R^{b19}$, $R^{b20}$ and $R^{b21}$ are independently in each occurrence a halogen atom, a hydroxyl group, a C1-C36 aliphatic hydrocarbon group, a C3-C36 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and the saturated cyclic hydrocarbon group has preferably 4 to 36 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group and v2, w2 and x2 independently each represent an integer of 0 to 5, and it is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each preferably represent 0 or 1.
Examples of the cation represented by the formula (b2-1) include the followings.
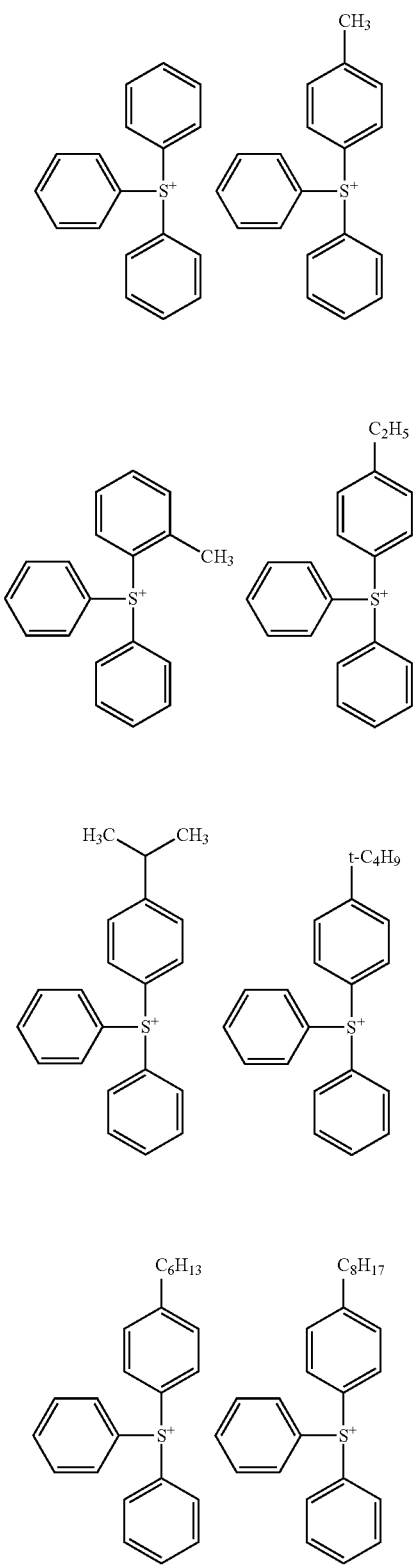
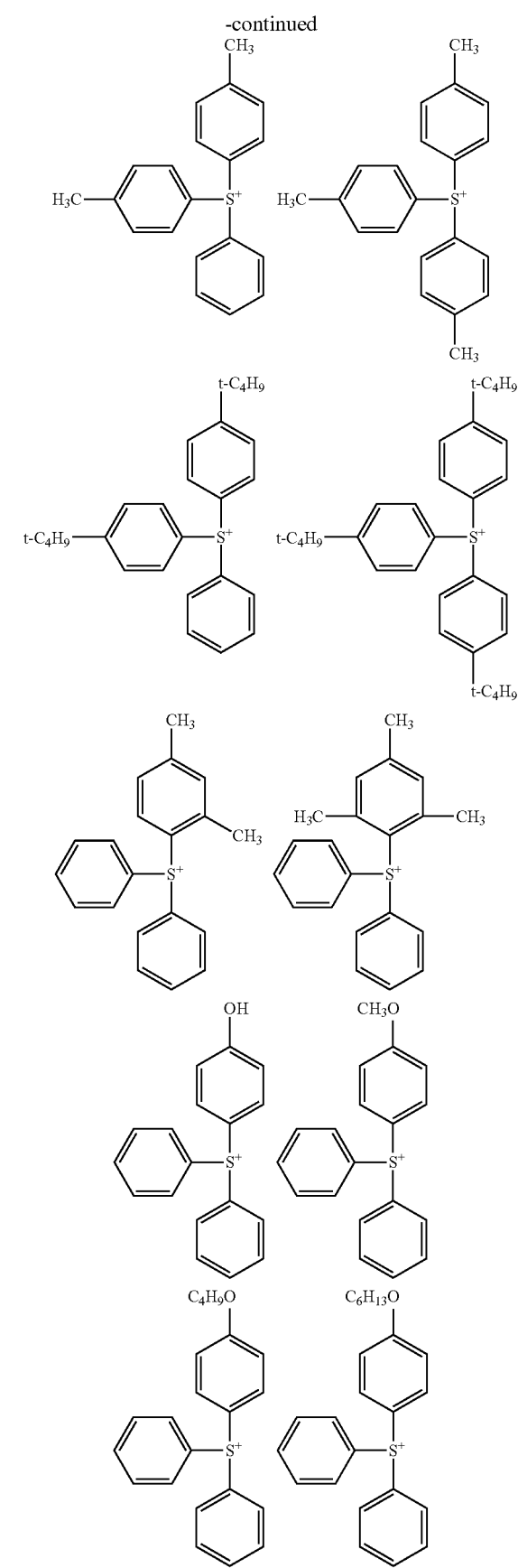

Examples of the cation represented by the formula (b2-2) include the followings.
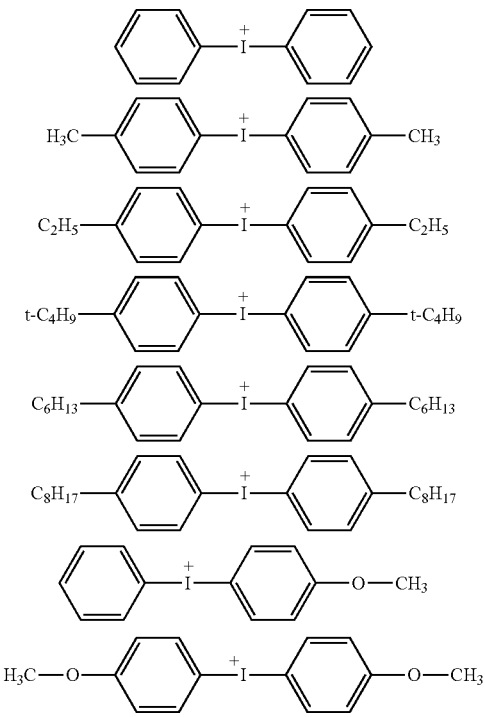
Examples of the cation represented by the formula (b2-3) include the followings.
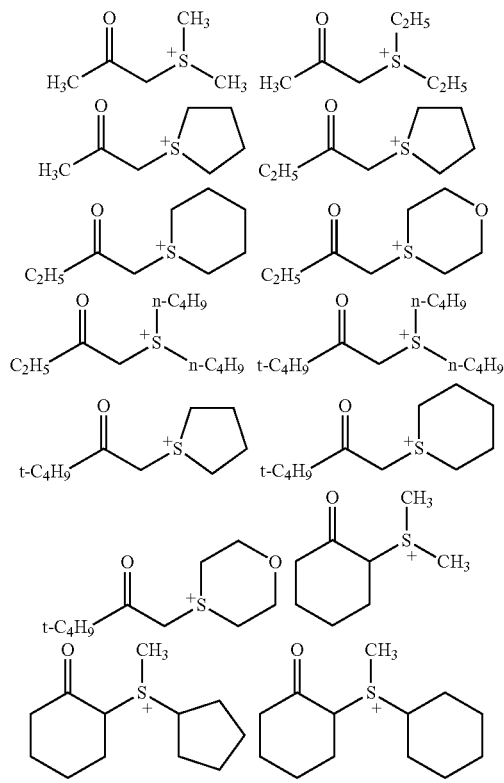
-continued
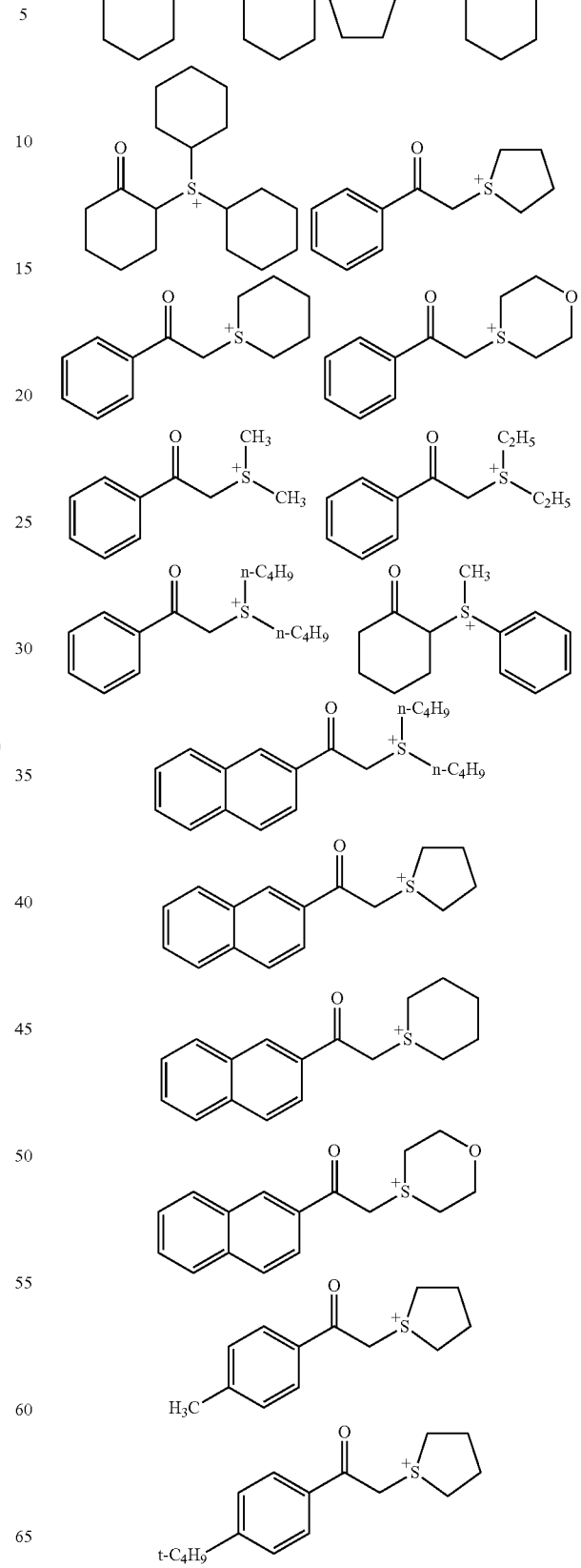

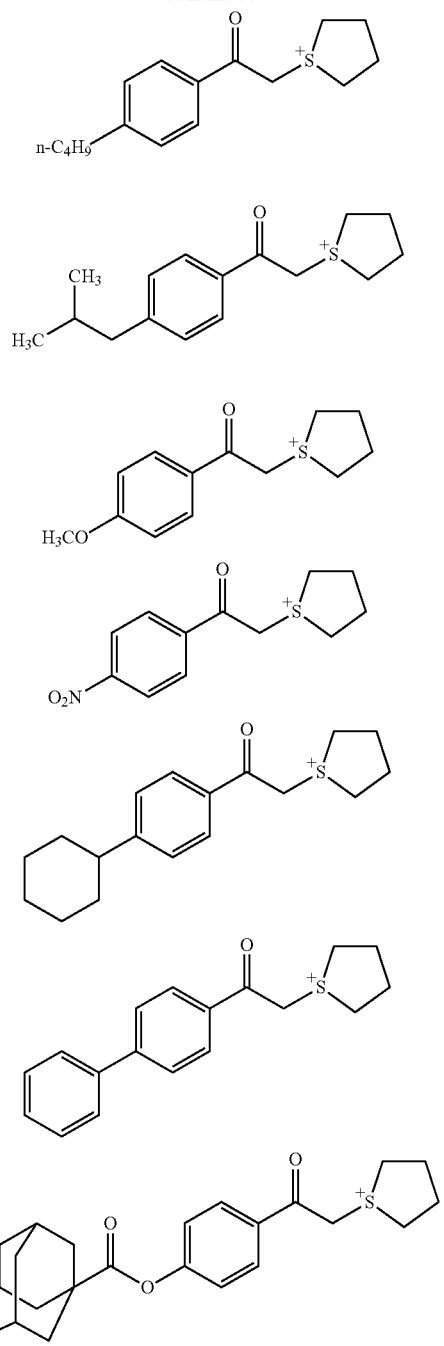
Examples of the cation represented by the formula (b2-4) include the followings.
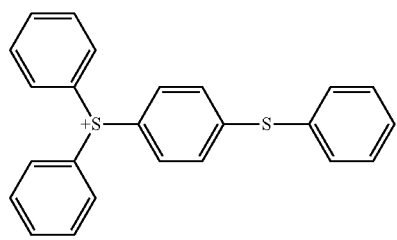
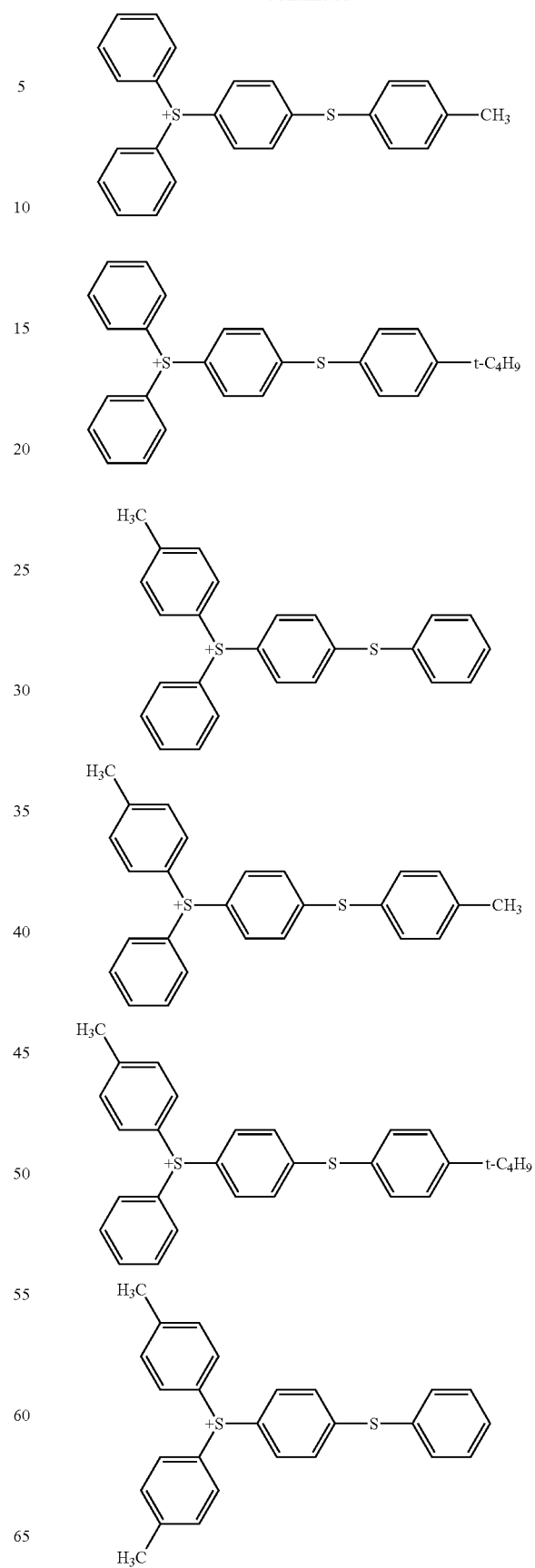

99
-continued
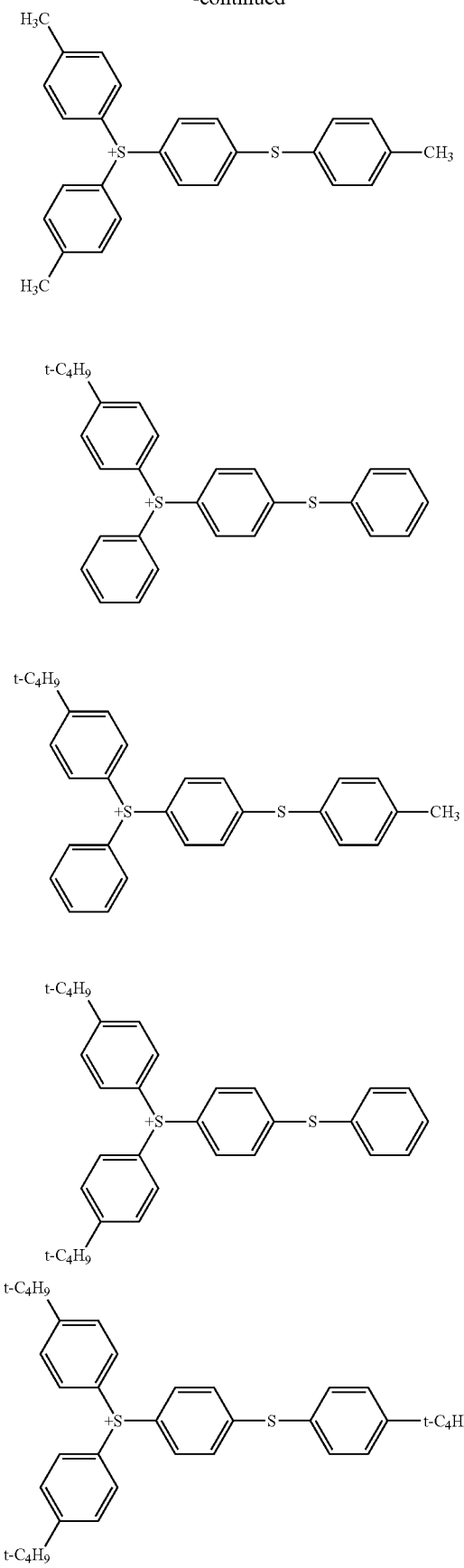
100
-continued
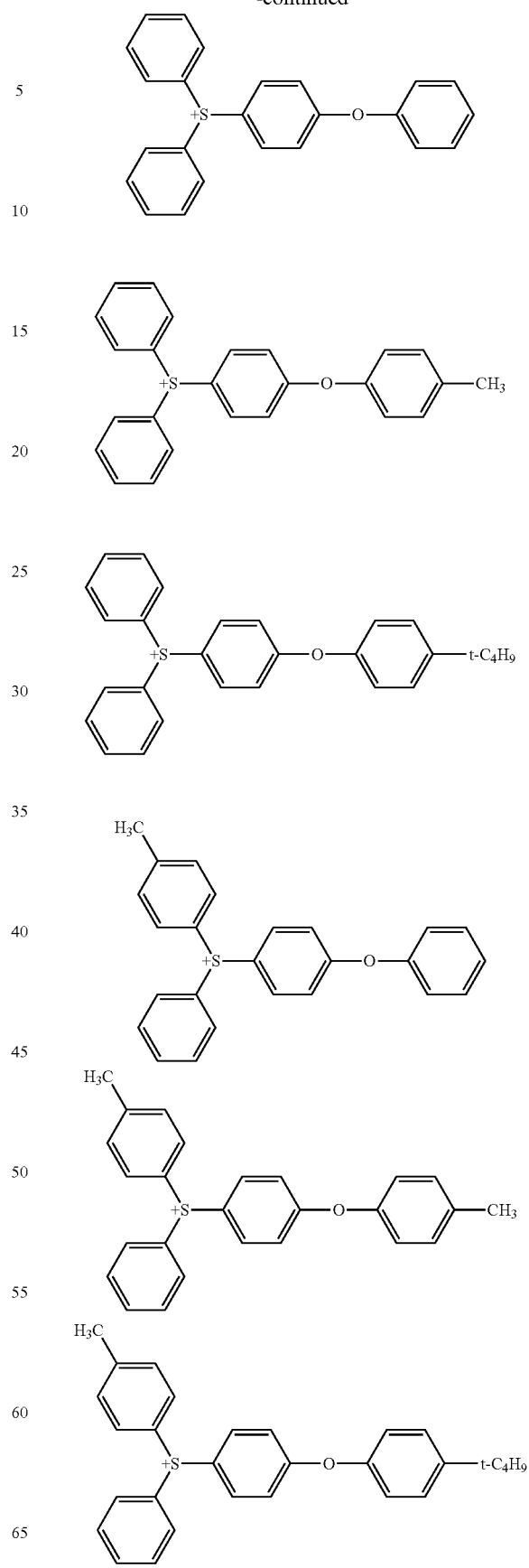

101
-continued
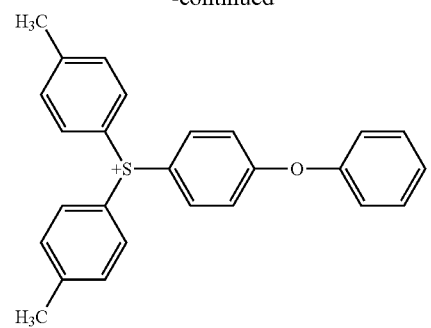
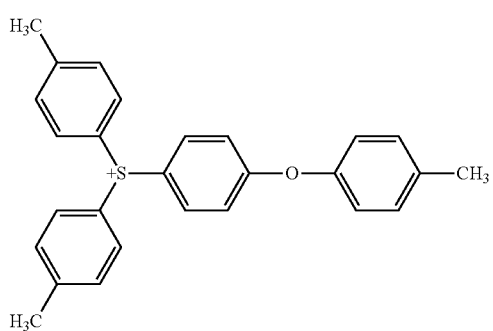
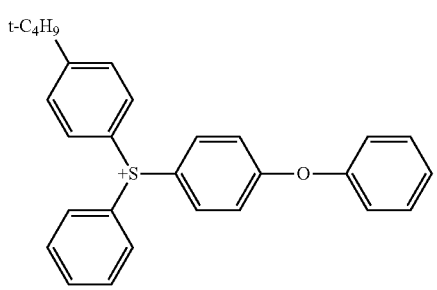
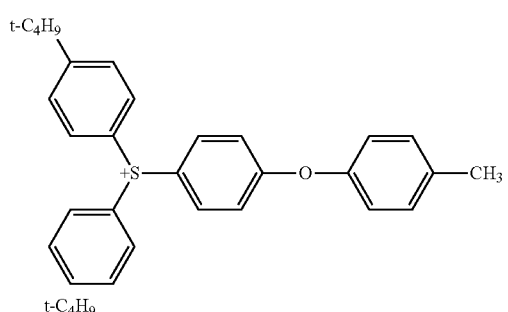
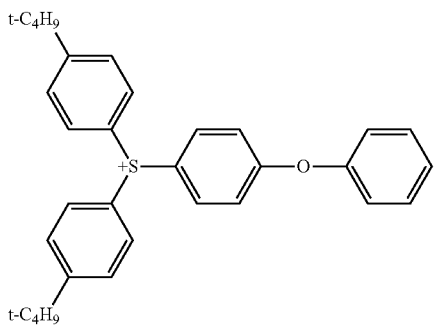
102
-continued
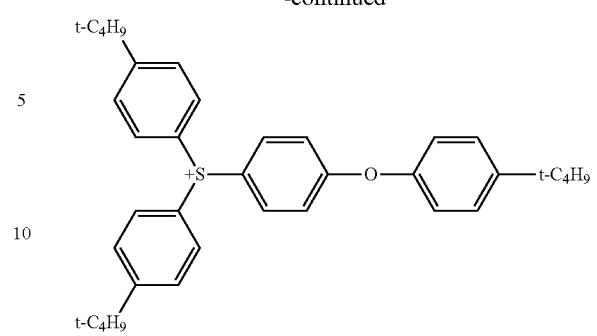
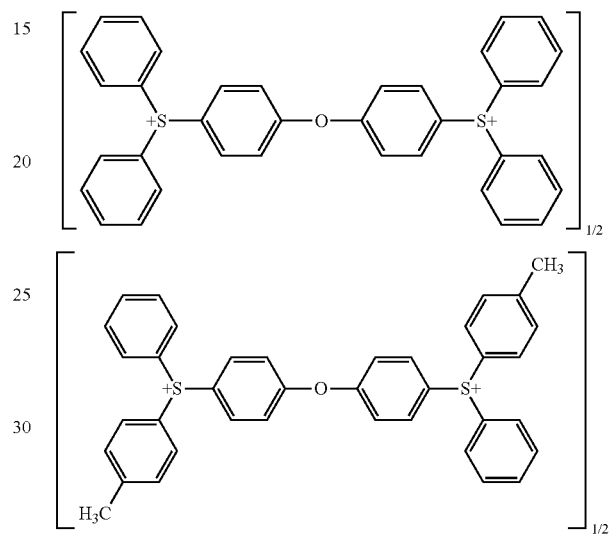
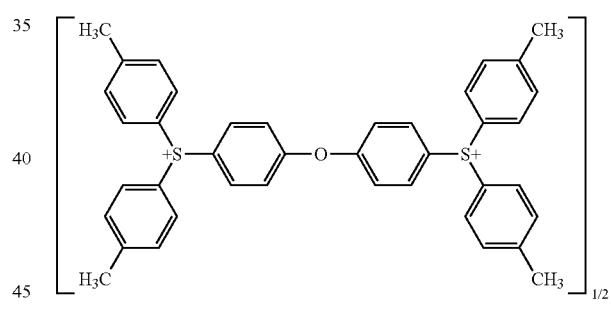
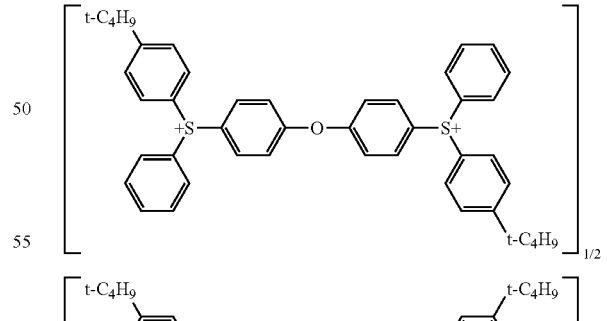
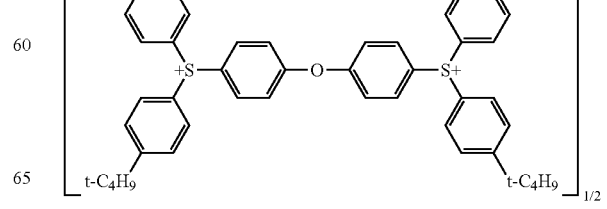

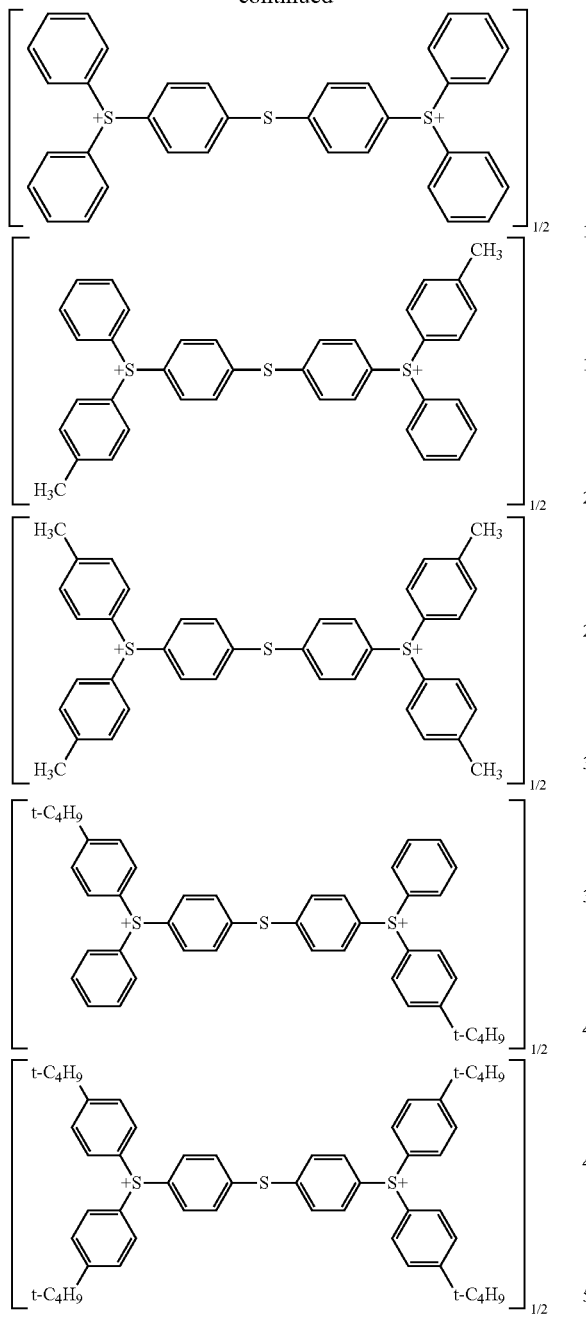

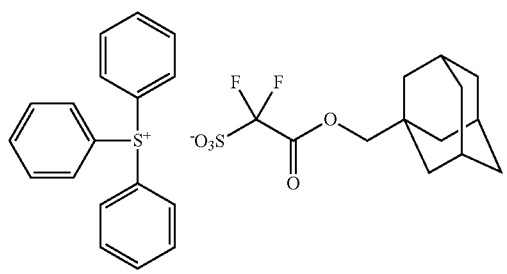
(B1-1)

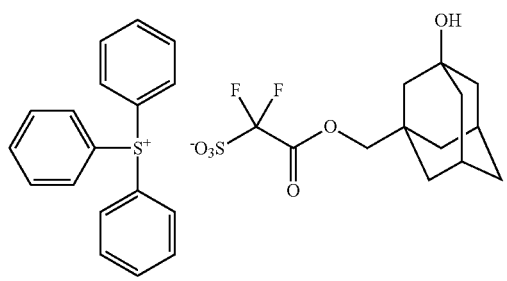
(B1-2)

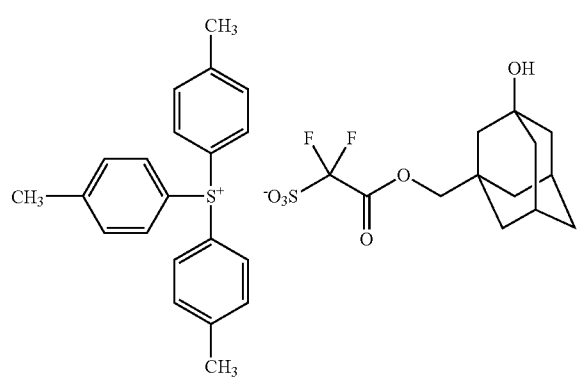
(B1-3)

Examples of the salt represented by the formula (B1) include a salt wherein the anion part is any one of the above-mentioned anion part and the cation part is any one of the above-mentioned cation part. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5)

and the cation represented by the formulae (b2-3).

The salt represented by the formulae (B1-1) to (B1-17) are preferable, and the salt represented by the formulae (B1-1), (B1-2), (B1-6), (B1-11), (B1-12), (B1-13) and (B1-14) are more preferable.

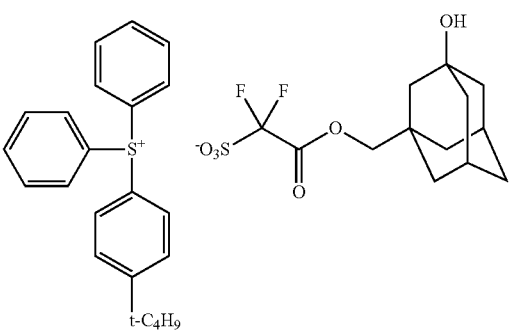
(B1-4)

(B1-5)
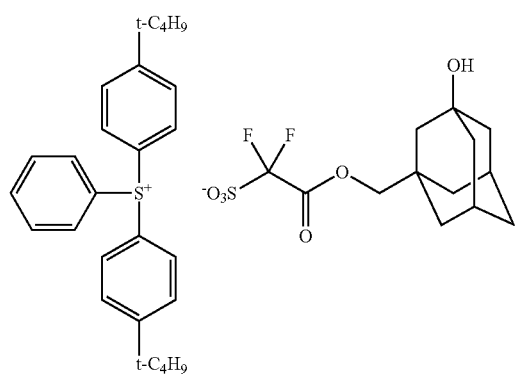
(B1-6)
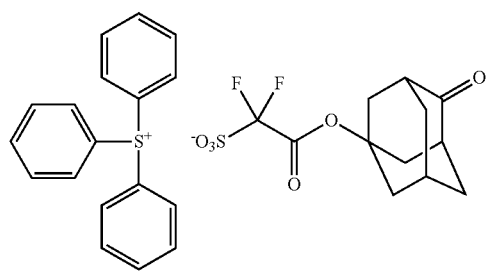
(B1-7)
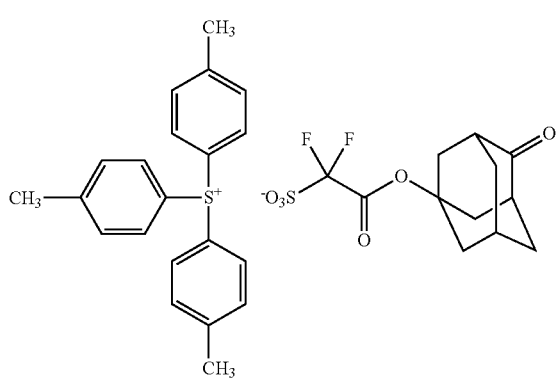
(B1-8)
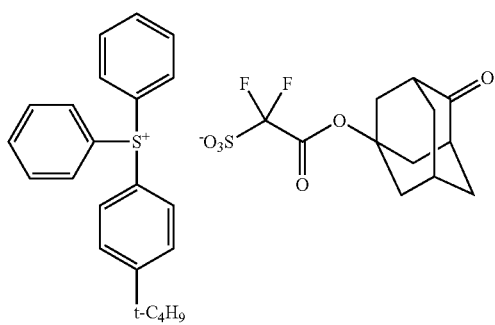
(B1-9)
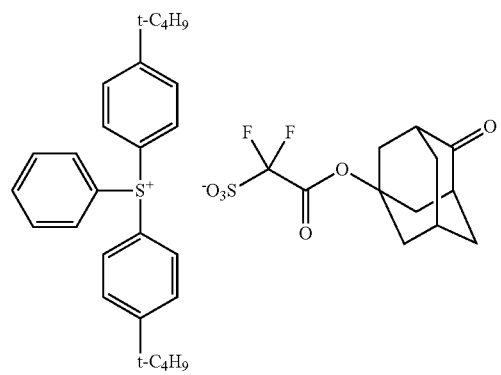
(B1-10)
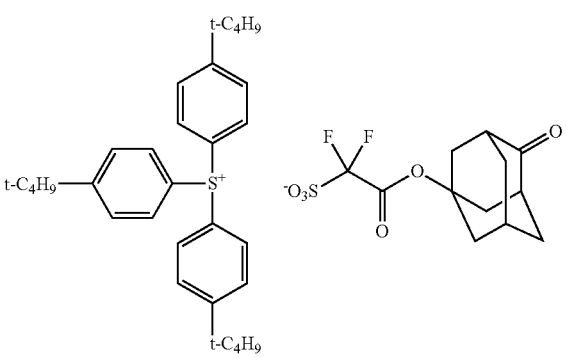
(B1-11)
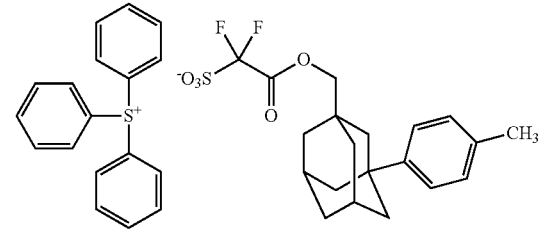
(B1-12)
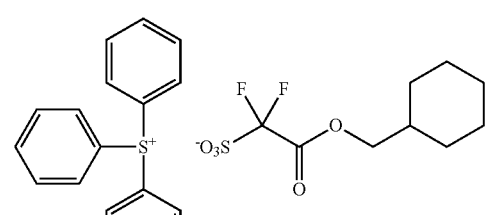
(B1-13)
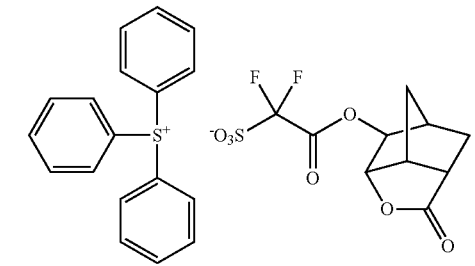

-continued (B1-14)

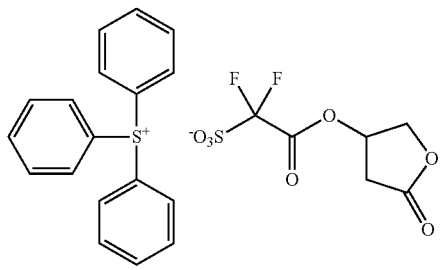

(B1-15)

(B1-16)

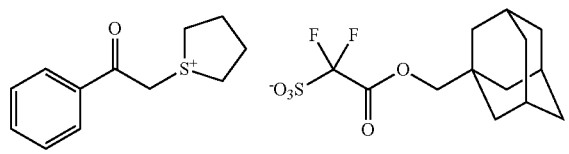

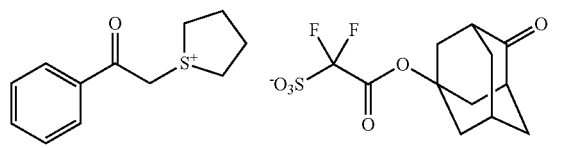

(B1-17)

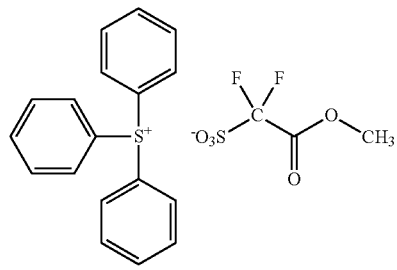

The salt represented by the formula (B1) can be produced, for example, by the method described in JP 2008-209917 A.

Two or more kinds of the acid generator can be used in combination.

The content of the acid generator is usually 1 part by weight or more and preferably 3 parts by weight or more per 100 parts by weight of the resin component, and 30 parts by weight or less and preferably 25 parts by weight or less per 100 parts by weight of the resin component.

Next, the compound represented by the formula (I'):

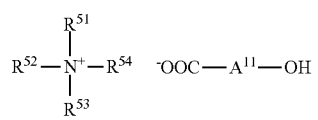
(I')

wherein $R^{51}$, $R^{52}$, $R^{53}$ and $R^{54}$ independently each represent a C1-C8 alkyl group, and $A^{11}$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents, will be illustrated below.

Examples of the C1-C8 alkyl group include a methyl group, an ethyl group, a propyl group, an isopropyl group, a butyl group, an isobutyl group, a sec-butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group, a 1-methylpentyl group, aheptyl group, and an octyl group, and a C1-C6 alkyl group is preferable.

Examples of the C3-C36 divalent saturated cyclic hydrocarbon group include a C3-C8 cycloalkanediyl group such as a cyclopropanediyl group, a cyclobutanediyl group, a cyclopentanediyl group, a cyclohexanediyl group, a methylcyclohexanediyl group, a cycloheptanediyl group and a cyclooctanediyl group, a C5-C12 cycloalkylalkane-diyl group such as a cyclobutylmethane-diyl group, a cyclopentylmethane-diyl group, a cyclohexylmethane-diyl group, a cycloheptylmethane-diyl group and a cyclooctylmethane-diyl group, and an adamantanediyl group and a 1-adamantylmethane-diyl group.

Examples of the C6-C20 divalent aromatic hydrocarbon group include a phenylene group which can have one or more alkyl groups such as a phenylene group, a methylphenylene group, an ethylphenylene group, a tert-butylphenylene group and a dimethylphenylene group, and a naphthylene group which can have one or more alkyl groups such as a naphthylene group and a methylnaphthylene group.

Examples of the C3-C36 divalent saturated cyclic hydrocarbon group containing one or more heteroatoms include a pyrrolidinediyl group, a pyrazolidinediyl group, an imidazolidinediyl group, an isooxazolidinediyl group, an isothiazolidinediyl group, a piperidinediyl group, a piperazinediyl group, a morpholinediyl group, a thiomorpholinediyl group, a diazolediyl group, a triazolediyl group and a tetrazolediyl group. Examples of the C6-C20 divalent aromatic hydrocarbon group containing one or more heteroatoms include a pyridinediyl group and a bipyridinediyl group.

Examples of the substituents include a halogen atom, a hydroxyl group, an amino group, a mercapto group (—SH), a hydrocarbon group having 30 or less carbon atoms, a heterocyclic group and an oxo group (=O).

As the compound represented by the formula (I'), a compound represented by the formula (I):

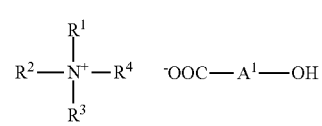
(I)

wherein $R^1$, $R^2$, $R^3$ and $R^4$ independently each represent a C1-C6 alkyl group, and $A^1$ is the same as defined above, is preferable.

Examples of the cation part of the compound represented by the formula (I') include the cations represented by the formulae (IA-1) to (IA-7):

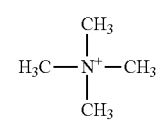
(IA-1)

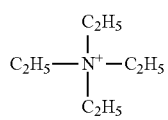
(IA-2)

-continued

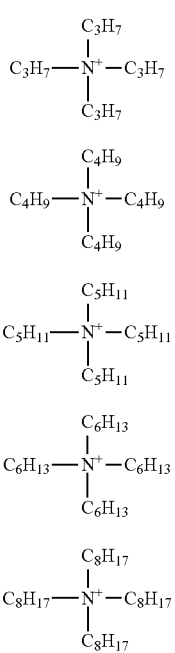

(IA-3)
(IA-4)
(IA-5)
(IA-6)
(IA-7)

Examples of the anion part of the compound represented by the formula (I') include the anions represented by the formulae (IB-1) to (IB-10):

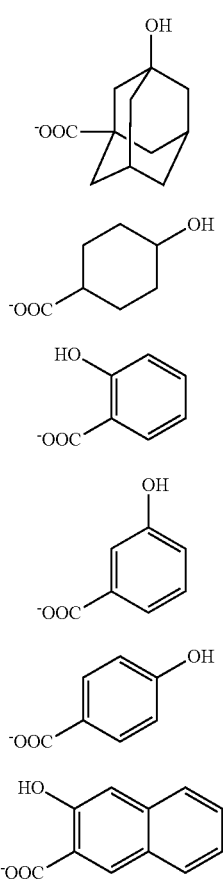

(IB-1)
(IB-2)
(IB-3)
(IB-4)
(IB-5)
(IB-6)

-continued

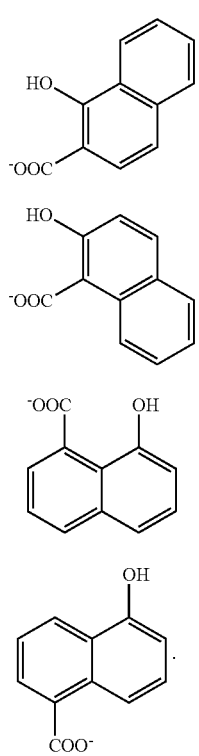

(IB-7)
(IB-8)
(IB-9)
(IB-10)

Examples of the compound represented by the formula (I') include compounds Nos. (I-1) to (I-31) as shown in Table 1, and compounds Nos. (I-1) to (I-5) and (I-12) to (I-31) are preferable, and compound Nos. (I-12) to (I-21) are more preferable.

TABLE 1

| Compound No. | Cation | Anion |
|---|---|---|
| (I-1) | (IA-1) | (IB-1) |
| (I-2) | (IA-1) | (IB-2) |
| (I-3) | (IA-1) | (IB-3) |
| (I-4) | (IA-1) | (IB-4) |
| (I-5) | (IA-1) | (IB-5) |
| (I-6) | (IA-2) | (IB-1) |
| (I-7) | (IA-2) | (IB-2) |
| (I-8) | (IA-2) | (IB-3) |
| (I-9) | (IA-3) | (IB-1) |
| (I-10) | (IA-3) | (IB-3) |
| (I-11) | (IA-3) | (IB-5) |
| (I-12) | (IA-4) | (IB-1) |
| (I-13) | (IA-4) | (IB-2) |
| (I-14) | (IA-4) | (IB-3) |
| (I-15) | (IA-4) | (IB-4) |
| (I-16) | (IA-4) | (IB-5) |
| (I-17) | (IA-4) | (IB-6) |
| (I-18) | (IA-4) | (IB-7) |
| (I-19) | (IA-4) | (IB-8) |
| (I-20) | (IA-4) | (IB-9) |
| (I-21) | (IA-4) | (IB-10) |
| (I-22) | (IA-5) | (IB-1) |
| (I-23) | (IA-5) | (IB-3) |
| (I-25) | (IA-5) | (IB-8) |
| (I-26) | (IA-6) | (IB-1) |
| (I-27) | (IA-6) | (IB-3) |
| (I-28) | (IA-6) | (IB-8) |
| (I-29) | (IA-7) | (IB-1) |
| (I-30) | (IA-7) | (IB-3) |
| (I-31) | (IA-7) | (IB-8) |

The compound represented by the formula (I') can be produced, for example, by reacting tetraalkylammonium hydroxide such as tetramethylammonium hydroxide with hydroxyalkanecarboxylic acid such as hydroxyadamantanecarboxylic acid.

Two or more kinds of the compound represented by the formula (I') can be used in combination.

The content of the compound represented by the formula (I') is usually 0.01 to 10% by weight, preferably 0.05 to 8% by weight and more preferably 0.01 to 5% by weight based on solid component.

The first photoresist composition of the present invention can contain one or more basic compounds other than the compound represented by the formula (I'), and the content of the basic compound is usually 0.01 to 1% by weight based on solid component.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

Preferable examples thereof include an aromatic amine represented by the formula (C2):

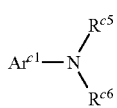

(C2)

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

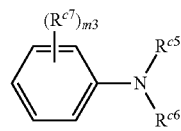

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

An ammonium salt represented by the formula (C2-2):

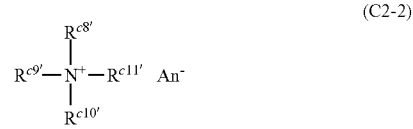

(C2-2)

wherein $R^{c8'}$, $R^{c9'}$, $R^{c10'}$, and $R^{c11'}$ each independently represent an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and $An^-$ represents $OH^-$, is also preferable. The aliphatic hydrocarbon group is preferably an alkyl group and the saturated cyclic hydrocarbon group is preferably a cycloalkyl group. The aliphatic hydrocarbon group preferably has 1 to 8 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline. Examples of the ammonium salt represented by the formula (C2-2) include tetramethylammonium hydroxide and tetrabutylammonium hydroxide.

Other examples of the basic compound include amines represented by the formulae (C3) to (C11):

(C3)

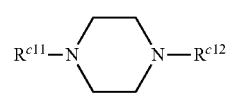

(C4)

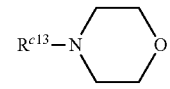

(C5)

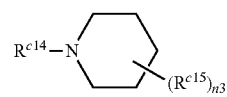

(C6)

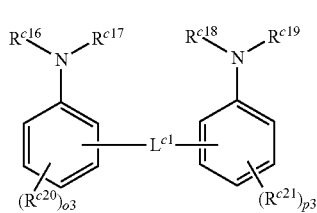
(C7)

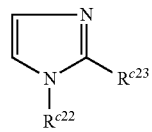
(C8)

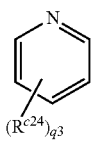
(C9)

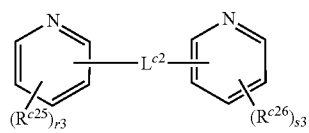
(C10)

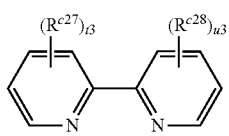
(C11)

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=NR^{c3})—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

The first photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less based on total amount of the photoresist composition of the present invention. The photoresist composition containing a solvent can be preferably used for producing a thin layer photoresist pattern.

The first photoresist composition of the present invention can contain, if necessary, a small amount of various additives such as a sensitizer, a dissolution inhibitor, other polymers, a surfactant, a stabilizer and a dye as long as the effect of the present invention is not prevented.

Next, the second photoresist composition of the present invention will be illustrated.

The second photoresist composition of the present invention comprises a resin comprising a structural unit derived from a compound having an acid-labile group and a structural unit derived from a compound represented by the formula (a2-10):

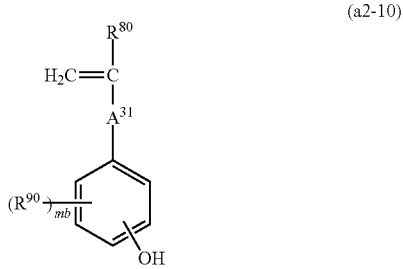

(a2-10)

wherein $R^{80}$ represents a hydrogen atom, a halogen atom, a C1-C6 alkyl group or a C1-C6 halogenated alkyl group, $R^{90}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, mb represents an integer of 0 to 4, and $A^{31}$ represents a divalent connecting group, and being insoluble or poorly soluble in an alkali aqueous solution but becoming soluble in an alkali aqueous solution by the action of an acid, an acid generator and a compound represented by the formula (I″):

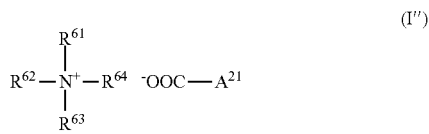

(I″)

wherein $R^{61}$, $R^{62}$, $R^{62}$ and $R^{64}$ independently each represent a C1-C20 alkyl group which can have one or more substituents, a C3-C30 saturated cyclic hydrocarbon group which can have one or more substituents, or a C2-C20 alkenyl group which can have one or more substituents, and $A^{21}$ represents a C1-C36 hydrocarbon group which can contain one or more heteroatoms and which have one or more substituents.

Examples of the structural unit derived from a compound having an acid-labile group include the same as described above, and as the compound having an acid-labile group, the compound represented by the formula (a1-1) or (a1-2) is preferable, and the compound represented by the formula (a1-1) is more preferable.

Preferable examples of the compound represented by the formulae (a1-1) and (a1-2) include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 1-ethyl-1-cyclohexyl acrylate and 1-ethyl-1-cyclohexyl methacrylate, and 2-methyl-2-adamantyl methacrylate, 2-ethyl-2-adamantyl methacrylate, 2-isopropyl-2-adamantyl methacrylate, and 1-ethyl-1-cyclohexyl methacrylate are more preferable.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

In the formula (a2-10), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-10), mb is preferably 0, 1 or 2, and is more preferably 0 or 1, and especially preferably 0.

The resin containing the structural unit derived from the monomer represented by the formula (a2-10) can be produced, for example, by polymerizing a monomer obtained by protecting a hydroxyl group of the monomer represented by the formula (a2-10) with an acetyl group followed by conducting deacetylation of the obtained polymer with a base.

Examples of the divalent connecting group include *—CO-$T^{10}$-, and *—$(CH_2)_{n'}$-$T^{11}$- in which * represents a binding position to $CH_2$=C($R^{80}$)-, $T^{10}$ represents —O— or —NH—, $T^{11}$ represents a single bond, —O—, —CO—O— or —NH—CO—O— and n' represents an integer of 0 to 4. $T^{10}$ is preferably —O—, and n' is preferably 0, 1 or 2.

Specific examples of $A^{31}$ include *—CO—O—, *—CO—NH—, *—CO—O—$CH_2$—CO—O—, *—CO—O—$(CH_2)_2$—O—, and *—CO—O—$(CH_2)_2$—NH—CO—O—.

Examples of the monomer represented by the formula (a2-10) include the followings.

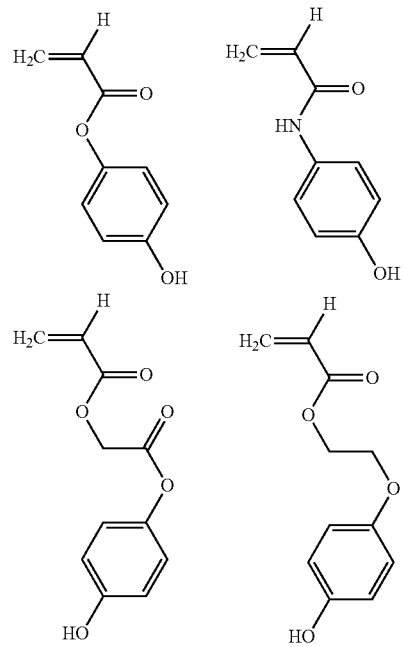

-continued

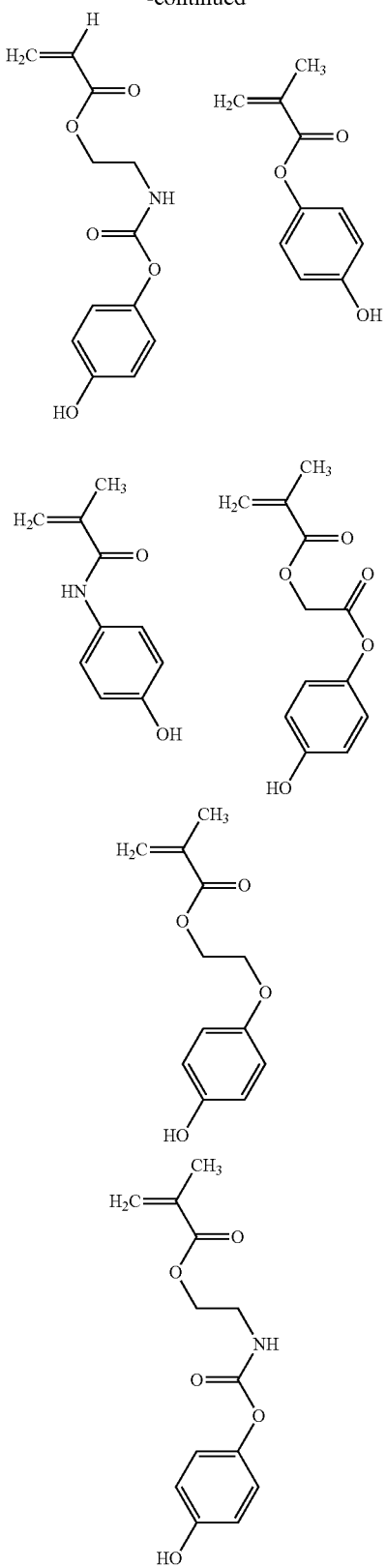

Among them, preferred is p-hydroxyphenyl methacrylate.

The content of the structural unit derived from the monomer represented by the formula (a2-10) is usually 5 to 90% by mole and preferably 10 to 85% by mole and more preferably 15 to 80% by mole based on total molar of all the structural units of the resin.

The resin can have one or more structural units derived from the compound having no acid-labile group. Examples of the compound having no acid-labile group include the same as described above, and the monomer having one or more hydroxyl groups and the monomer having a lactone ring are preferable, and the monomers represented by the formulae (a2-1), (a3-1), (a3-2) and (a3-3) are more preferable.

As the monomer represented by the formula (a2-1), 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

When the resin contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of the resin.

As the monomers represented by the formulae (a3-1), (a3-2) and (a3-3), 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate are preferable and 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate are more preferable.

When the resin contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of the resin.

Preferable resin is a resin containing the structural unit derived from a compound represented by the formula (a2-10), the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,000 or more of the weight-average molecular weight, preferably 2,500 or more of the weight-average molecular weight, and more preferably 3,000 or more of the weight-average molecular weight. The resin usually has 30,000 or less of the weight-average molecular weight, preferably has 15,000 or less of the weight-average molecular weight, more preferably 9,000 or less of the weight-average molecular weight and especially preferably 6,000 or less of the weight-average molecular weight. The weight-average molecular weight can be measured with gel permeation chromatography.

The second photoresist composition of the present invention usually includes 80% by weight or more of the resin based on sum of solid component.

Examples of the acid generator include the same as described above. Preferable acid generator is the salt represented by the formula (B1), and more preferable acid generator is one of the salt represented by the formula (B1-1) to (B1-17), and the salt represented by the formulae (B1-1), (B1-2), (B1-6), (B1-11), (B1-12), (B1-13) and (B1-14) are especially preferable.

Two or more kinds of the acid generator can be used in combination.

The content of the acid generator is usually 1 part by weight or more and preferably 3 parts by weight or more per 100 parts by weight of the resin component, and 30 parts by weight or less and preferably 25 parts by weight or less per 100 parts by weight of the resin component.

The second photoresist composition contains a compound represented by the formula (I″):

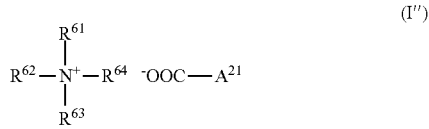

wherein $R^{61}$, $R^{62}$, $R^{62}$ and $R^{64}$ independently each represent a C1-C20 alkyl group which can have one or more substituents, a C3-C30 saturated cyclic hydrocarbon group which can have one or more substituents, or a C2-C20 alkenyl group which can have one or more substituents, and $A^{21}$ represents a C1-C36 hydrocarbon group which can contain one or more heteroatoms and which have one or more substituents.

Examples of the C1-C20 alkyl group include a methyl group, an ethyl group, a propyl group, an isopropyl group, a butyl group, an isobutyl group, a sec-butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and isocyl group, and a C1-C15 alkyl group is preferable, and C1-C10 alkyl group is more preferable.

Examples of the C3-C30 saturated cyclic hydrocarbon group include an adamantyl group, a norbornyl group, an isobornyl group, a tricyclodecyl group and a tetracyclodecyl group. The saturated cyclic hydrocarbon group preferably has 5 to 30 carbon atoms, more preferably 5 to 20 carbon atoms, much more preferably 6 to 15 carbon atoms and especially preferably 6 to 12 carbon atoms.

The alkenyl group preferably has 2 to 5 carbon atoms, and alkenyl group formed by combining the above-mentioned alkyl group with a vinyl group is more preferable.

Examples of the substituents include a halogen atom, a halogenated alkyl group such as a C1-C20 halogenated alkyl group, an alkyl group such as a C1-C20 alkyl group, an alkoxy group, a hydroxyalkoxy group, an alkoxyalkoxy group, an alkoxycarbonyloxy group, an alkoxycarbonylalkoxy group, an alkoxycarbonyl group, an aryl group, a heteroaryl group and an aralkyl group. Examples of the halogen atom include a fluorine atom, a chlorine atom, a bromine atom and an iodine atom, and a fluorine atom is preferable. As the halogenated alkyl group, a fluorinated alkyl group is preferable. Examples of the alkyl group include the same as described in $R^{61}$, $R^{62}$, $R^{63}$ and $R^{64}$. Examples of aryl group include a phenyl group, a biphenyl group, a fluorenyl group, a naphthyl group, an anthryl group and a phenanthryl group. Examples of the heteroaryl group include the above-mentioned aryl groups in which one or more carbon atoms composed of the aromatic ring are replaced by a heteroatom such as an oxygen atom, a sulfur atom and a nitrogen atom. Examples of the aralkyl group include a benzyl group, a phenethyl group, a 1-naphthylmethyl group, a 2-naphthylmethyl group, a 1-naphthylethyl group and a 2-naphthylethyl group. As the aralkyl group, an aryl-substituted C1-C4 alkyl group is preferable, and an aryl-substituted C1-C2 alkyl group is more preferable, and an aryl-substituted methyl group is especially preferable. The aryl group, the heteroaryl group and the aralkyl group can have one or more substituents such as a C1-C10 alkyl group, a halogenated alkyl group (e.g. a C1-C8 halogenated alkyl group), an alkoxy group, a hydroxyl group and a halogen atom.

It is preferred that $R^{61}$, $R^{62}$, $R^{63}$ and $R^{64}$ independently each represent a linear alkyl group, a linear alkenyl group, or a saturated cyclic hydrocarbon group, and it is more preferred that $R^{61}$, $R^{62}$, $R^{63}$ and $R^{64}$ independently each represent a linear alkyl group. It is preferred that one of $R^{61}$, $R^{62}$, $R^{63}$ and $R^{64}$ represents an alkyl group having 4 or more carbon atoms, and it is more preferred that one of $R^{61}$, $R^{62}$, $R^{63}$ and $R^{64}$ represents a C5-C10 alkyl group, and it is especially preferred that one of $R^{61}$, $R^{62}$, $R^{63}$ and $R^{64}$ represents an alkyl group having 1 to 3 carbon atoms, preferably 1 or 2 carbon atoms, and three of $R^{61}$, $R^{62}$, $R^{63}$ and $R^{64}$ represents an alkyl group having 4 or more carbon atoms.

Examples of the C1-C36 hydrocarbon group represented by $A^{21}$ include a saturated hydrocarbon group, an unsaturated hydrocarbon group, an aromatic hydrocarbon group and an aralkyl group. Examples of the saturated hydrocarbon group include a C1-C20 alkyl group and a C3-C20 saturated cyclic hydrocarbon group which are described in $R^{61}$, $R^{62}$, $R^{63}$ and $R^{64}$. The unsaturated hydrocarbon group preferably has 2 to 5 carbon atoms, more preferably 2 to 4 carbon atoms, and especially has 3 carbon atoms. Examples of the unsaturated hydrocarbon group include a vinyl group, a propenyl group, a butynyl group, a 1-methylpropenyl group, and a 2-methylpropenyl group, and a propenyl group is preferable. The aromatic hydrocarbon group preferably has 6 to 36 carbon atoms, more preferably 6 to 30 carbon atoms, much more preferably 6 to 20 carbon atoms, and especially preferably 6 to 15 carbon atoms. Examples of the aromatic hydrocarbon group include an aryl group such as a phenyl group, a biphenyl group, a fluorenyl group, a naphthyl group, an anthryl group and a phenanthryl group. Examples of the aralkyl group include a benzyl group, a phenethyl group, a 1-naphthylmethyl group, a 2-naphthylmethyl group, a 1-naphthylethyl group and a 2-naphthylethyl group. As the aralkyl group, an aryl-substituted C1-C4 alkyl group is preferable, and an aryl-substituted C1-C2 alkyl group is more preferable, and an aryl-substituted methyl group is especially preferable.

The C1-C36 hydrocarbon group can have one or more substituents, and examples of the substituents include an alkyl group, an aryl group, an alkoxy group, a halogen atom, a halogenated alkyl group, a hydroxyl group and an oxo group (=O), and a halogen atom and a hydroxyl group are preferable, and a hydroxyl group is more preferable. The C1-C36 hydrocarbon group can contain one or more heteroatoms such as an oxygen atom, a sulfur atom and a nitrogen atom. Examples of the alkyl group include a C1-C5 alkyl group such as a methyl group, an ethyl group, a propyl group, a butyl group and a tert-butyl group, and examples of the aryl group include the same as described above. Examples of the alkoxy group include a C1-C5 alkoxy group such as a methoxy group, an ethoxy group, a propoxy group, a butoxy group and a tert-butoxy group, and methoxy and ethoxy groups are preferable. Examples of the halogen atom include a fluorine atom, a chlorine atom, a bromine atom and an iodine atom, and a fluorine atom is preferable.

As the compound represented by the formula (I''), the compound represented by the above-mentioned formula (I) is preferable.

Examples of the cation part of the compound represented by the formula (I'') include the cations represented by the formulae (IA-1) to (IA-8):

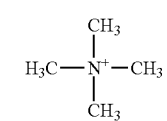
(IA-1)

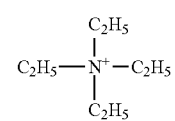
(IA-2)

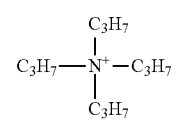
(IA-3)

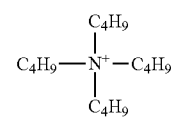
(IA-4)

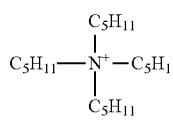
(IA-5)

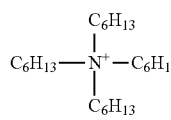
(IA-6)

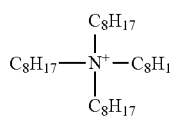
(IA-7)

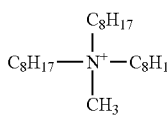
(IA-8)

Examples of the anion part of the compound represented by the formula (I'') include the anions represented by the formulae (IB-1) to (IB-11):

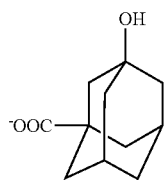
(IB-1)

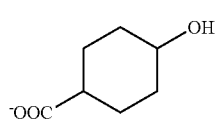
(IB-2)

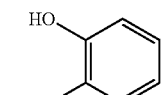
(IB-3)

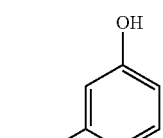
(IB-4)

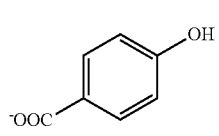
(IB-5)

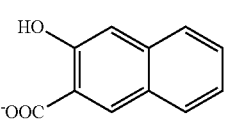
(IB-6)

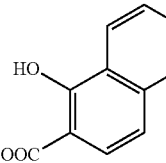
(IB-7)

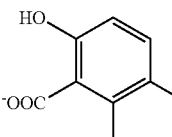
(IB-8)

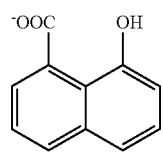
(IB-9)

-continued

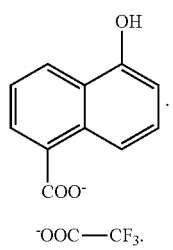
(IB-10)

⁻OOC—CF₃.
(IB-11)

Examples of the compound represented by the formula (I″) include compounds Nos. (I-1) to (I-31) as shown in the above-mentioned Table 1, and a compound represented by the formula (I″) in which the cation is represented by the formula (IA-8) and the anion is represented by the formula (IB-11), and compounds Nos. (I-1) to (I-5) and (I-12) to (I-31) are preferable, and compound Nos. (I-12) to (I-21) are more preferable.

The compound represented by the formula (I″) can be produced, for example, by reacting tetraalkylammonium hydroxide such as tetramethylammonium hydroxide with hydroxyalkanecarboxylic acid such as hydroxyadamantanecarboxylic acid.

Two or more kinds of the compound represented by the formula (I″) can be used in combination.

The content of the compound represented by the formula (I″) is usually 0.01 to 10% by weight, preferably 0.05 to 8% by weight and more preferably 0.01 to 5% by weight based on solid component.

The second photoresist composition of the present invention can also contain one or more basic compounds other than the compound represented by the formula (I″), and the content of the basic compound is usually 0.01 to 1% by weight based on solid component.

The basic compound is preferably a basic nitrogen-containing organic compound, and examples thereof include the same as described above.

The second photoresist composition of the present invention usually contains one or more solvents, too. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less based on total amount of the photoresist composition of the present invention. The photoresist composition containing a solvent can be preferably used for producing a thin layer photoresist pattern.

The second photoresist composition of the present invention can contain, if necessary, a small amount of various additives such as a sensitizer, a dissolution inhibitor, other polymers, a surfactant, a stabilizer and a dye as long as the effect of the present invention is not prevented.

The first and second photoresist compositions of the present invention are useful for a chemically amplified photoresist composition.

A photoresist pattern can be produced by the following steps (1) to (5):

(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern in a good resulution, and therefore, the photoresist composition of the present invention is suitable for ArF excimer laser lithography, KrF excimer laser lithography, EUV (extreme ultraviolet) lithography, EUV immersion lithography and EB (electron beam) lithography, and the photoresist composition of the present invention is especially suitable for EUV (extreme ultraviolet) lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Two Columns with guard column): TSKgel G4000H$_{XL}$+TSKgel G2000H$_{XL}$, manufactured by TOSOH CORPORATION, Solvent: Tetrahydrofuran, Flow rate: 1.0 mL/min., Detector: RI detector, Column temperature: 40° C., Injection volume: 100 µL] using standard polystyrene, manufactured by TOSOH CORPORATION, as a standard reference material. Structures of compounds were determined by NMR (ECA-500 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Resin Synthesis Example 1

A solution prepared by dissolving 11.18 parts of 2-ethyl-2-adamantyl methacrylate, 15.09 parts of p-acetoxystyrene and 3.55 parts of 3-hydroxy-1-adamantyl methacrylate in 28.82 parts of 1,4-dioxane was heated up to 82° C. To a solution, 0.86 part of azobisisobutyronitrile was added, and the resultant mixture was stirred for 6 hours at 82° C. The obtained reaction mixture was cooled, and then, was poured into a mixture of 291.41 parts of methanol and 124.89 parts of ion-exchanged water. The precipitate was collected by filtration. The obtained precipitate and 2.93 parts of 4-dimethylaminopyridine were mixed with methanol of which amount was the same as that of the obtained precipitate, and the resultant mixture was refluxed for 15 hours. The obtained mixture was cooled and then, was neutralized with 2.16 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 22.42 parts of a resin having a weight-average molecular weight of about 8.5×10$^3$. This resin had the structural units represented by the followings. This is called as resin A1.

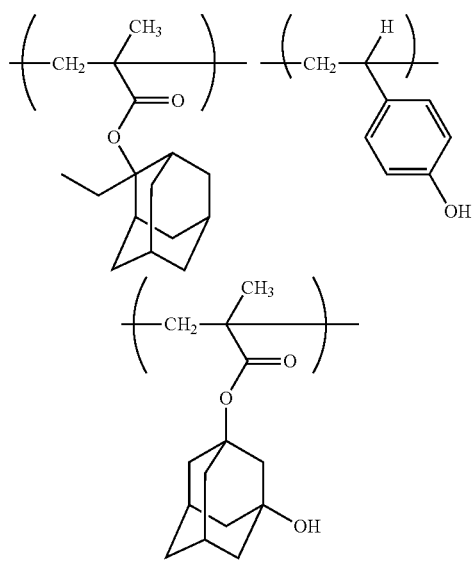

Resin Synthesis Example 2

A solution prepared by dissolving 11.18 parts of 2-ethyl-2-adamantyl methacrylate, 14.60 parts of p-acetoxystyrene and 3.55 parts of 3-hydroxy-1-adamantyl methacrylate in 28.82 parts of 1,4-dioxane was heated up to 87° C. To a solution, 2.96 parts of azobisisobutyronitrile was added, and the resultant mixture was stirred for 6 hours at 87° C. The obtained reaction mixture was cooled, and then, was poured into a mixture of 291.41 parts of methanol and 124.89 parts of ion-exchanged water. The precipitate was collected by filtration. The obtained precipitate and 2.93 parts of 4-dimethylaminopyridine were mixed with methanol of which amount was the same as that of the obtained precipitate, and the resultant mixture was refluxed for 15 hours. The obtained mixture was cooled and then, was neutralized with 2.16 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 27.71 parts of a resin having a weight-average molecular weight of about 3.4×10$^3$. This resin had the structural units represented by the followings. This is called as resin A2.

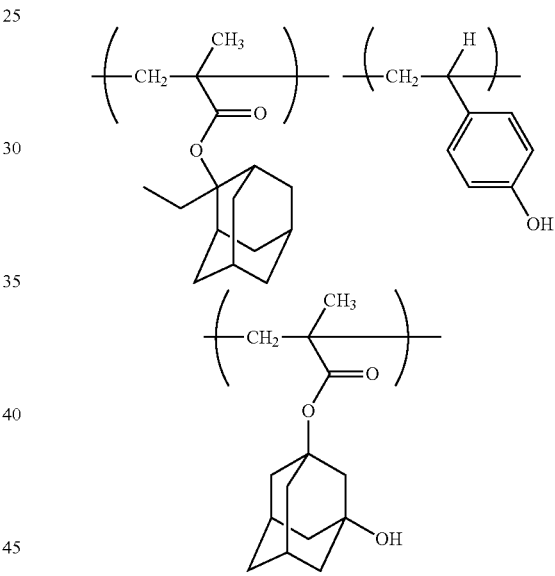

Resin Synthesis Example 3

To 19.59 parts of 1,4-dioxane, a solution prepared by dissolving 11.18 parts of 1-adamantyl-1-methylethyl methacrylate, 14.60 parts of p-acetoxystyrene, 3.54 parts of 3-hydroxy-1-adamantyl methacrylate and 2.96 parts of azobisisobutyronitrile in 29 . 39 parts of 1,4-dioxane was added dropwise at 87° C. over 1 hour. The resultant mixture was stirred for 6 hours at 87° C. The obtained reaction mixture was cooled, and then, was poured into a mixture of 297.16 parts of methanol and 127.35 parts of ion-exchanged water. The precipitate was collected by filtration. The obtained precipitate and 2.93 parts of 4-dimethylaminopyridine were mixed with methanol of which amount was the same as that of the obtained precipitate, and the resultant mixture was refluxed for 15 hours. The obtained mixture was cooled and then, was neutralized with 2.16 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 28.01 parts of a resin having a weight-average molecular weight of about $4.3 \times 10^3$. This resin had the structural units represented by the followings. This is called as resin A3.

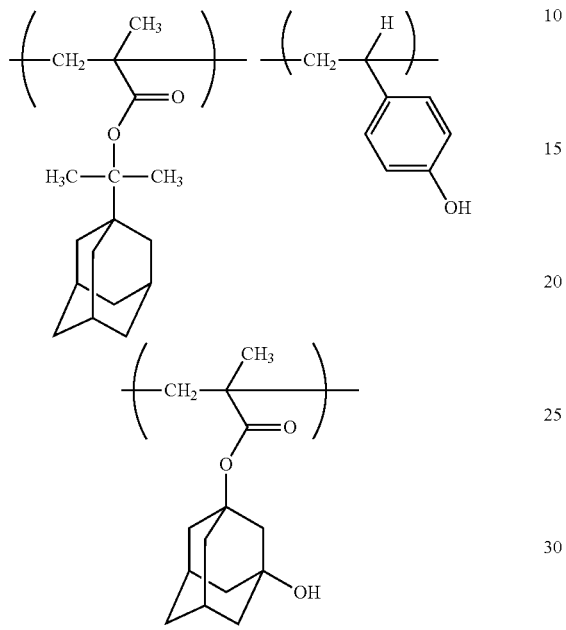

Resin Synthesis Example 4

A solution prepared by dissolving 10.54 parts of 2-methyl-2-adamantyl methacrylate, 14.60 parts of p-acetoxystyrene and 3.55 parts of 3-hydroxy-1-adamantyl methacrylate in 47.09 parts of 1,4-dioxane was heated up to 87° C. To a solution, 2.96 parts of azobisisobutyronitrile was added, and the resultant mixture was stirred for 6 hours at 87° C. The obtained reaction mixture was cooled, and then, was poured into a mixture of 285.67 parts of methanol and 122.43 parts of ion-exchanged water. The precipitate was collected by filtration. The obtained precipitate and 2.93 parts of 4-dimethylaminopyridine were mixed with methanol of which amount was the same as that of the obtained precipitate, and the resultant mixture was refluxed for 15 hours. The obtained mixture was cooled and then, was neutralized with 2.16 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 28.15 parts of a resin having a weight-average molecular weight of about $3.7 \times 10^3$. This resin had the structural units represented by the followings. This is called as resin A4.

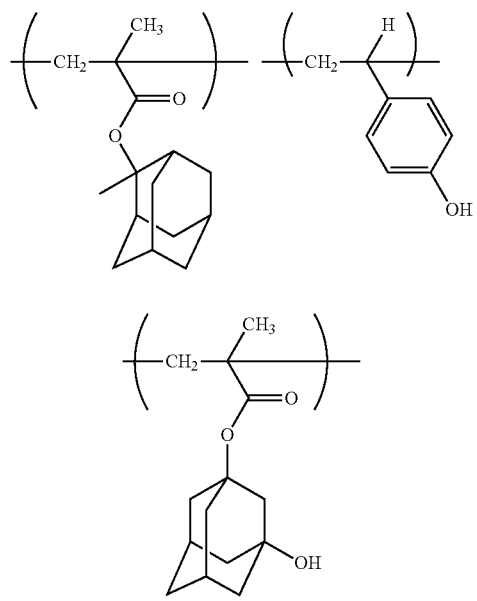

Resin Synthesis Example 5

A solution prepared by dissolving 8.94 parts of 2-ethyl-2-adamantyl methacrylate, 9.73 parts of p-acetoxystyrene and 2.04 parts of methacryloyloxy-γ-butyrolactone in 38.03 parts of 1,4-dioxane was heated up to 87° C. To a solution, 0.69 part of azobisisobutyronitrile was added, and the resultant mixture was stirred for 6 hours at 87° C. The obtained reaction mixture was cooled, and then, was poured into a mixture of 285.67 parts of methanol and 122.43 parts of ion-exchanged water. The precipitate was collected by filtration. The obtained precipitate and 2.07 parts of 4-dimethylaminopyridine were mixed with methanol of which amount was the same as that of the obtained precipitate, and the resultant mixture was refluxed for 15 hours. The obtained mixture was cooled and then, was neutralized with 1.02 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 18.08 parts of a resin having a weight-average molecular weight of about $8.9 \times 10^3$. This resin had the structural units represented by the followings. This is called as resin A5.

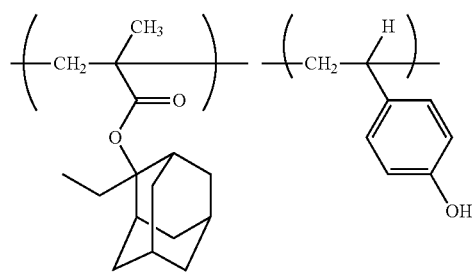

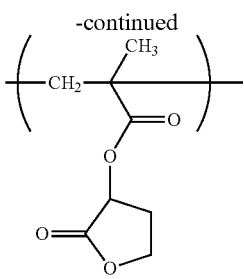

Resin Synthesis Example 6

To 40.80 parts of 1,4-dioxane, a solution prepared by dissolving 17.54 parts of (2-methyladamantan-2-yl)oxy-2-oxoethyl methacrylate, 19.46 parts of p-acetoxystyrene, 4.73 parts of 3-hydroxy-1-adamantyl methacrylate and 4.60 parts of azobisisobutyronitrile in 47.61 parts of 1,4-dioxane was added dropwise at 80° C. over 1 hour. The resultant mixture was stirred for 6 hours at 80° C. The obtained reaction mixture was cooled, and then, was poured into a mixture of 353.64 parts of methanol and 253.76 parts of ion-exchanged water. The precipitate was collected by filtration. The obtained precipitate and 4.17 parts of 4-dimethylaminopyridine were mixed with methanol of which amount was the same as that of the obtained precipitate, and the resultant mixture was refluxed for 15 hours. The obtained mixture was cooled and then, was neutralized with 2.05 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 39.40 parts of a resin having a weight-average molecular weight of about $4.9 \times 10^3$. This resin had the structural units represented by the followings. This is called as resin A6.

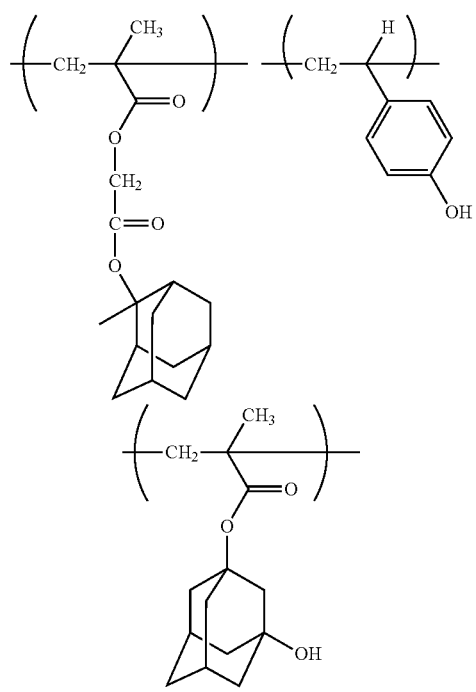

Resin Synthesis Example 7

A solution prepared by dissolving 10.54 parts of 2-methyl-2-adamantyl methacrylate, 14.60 parts of p-acetoxystyrene and 1.56 parts of styrene in 44.12 parts of 1,4-dioxane was heated up to 87° C. To a solution, 0.69 part of azobisisobutyronitrile was added, and the resultant mixture was stirred for 6 hours at 87° C. The obtained reaction mixture was cooled, and then, was poured into a mixture of 267.63 parts of methanol and 114.70 parts of ion-exchanged water. The precipitate was collected by filtration. The obtained precipitate and 2.67 parts of 4-dimethylaminopyridine were mixed with methanol of which amount was the same as that of the obtained precipitate, and the resultant mixture was refluxed for 15 hours. The obtained mixture was cooled and then, was neutralized with 1.31 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 25.16 parts of a resin having a weight-average molecular weight of about $3.3 \times 10^3$. This resin had the structural units represented by the followings. This is called as resin A7.

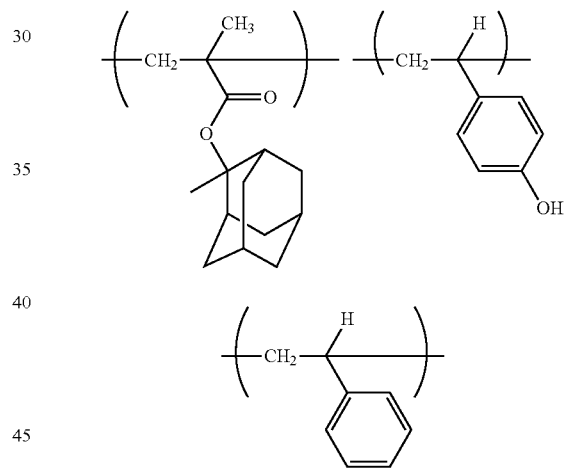

Resin Synthesis Example 8

To 27.81 parts of 1,4-dioxane, a solution prepared by dissolving 17.54 parts of 2-methyl-2-adamantyl methacrylate, 20.00 parts of p-hydroxyphenyl methacrylate, 5.30 parts of 3-hydroxy-1-adamantyl methacrylate and 3.32 parts of azobisisobutyronitrile in 41.71 parts of 1,4-dioxane was added dropwise at 87° C. over 1 hour. The resultant mixture was stirred for 6 hours at 87° C. The obtained reaction mixture was cooled, and then, was poured into a mixture of 422 parts of methanol and 181 parts of ion-exchanged water. The precipitate was collected by filtration. The obtained precipitate was washed three times with 301 parts of methanol, and then, dried to obtain 19.38 parts of a resin having a weight-average molecular weight of about $7.1 \times 10^3$. This resin had the structural units represented by the followings. This is called as resin A8.

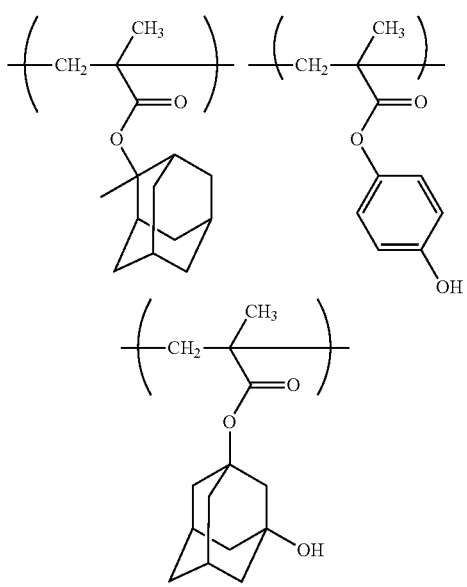

Synthesis Example 1

A mixture of 7.56 parts of 3-hydroxyadamantanecarboxylic acid and 302.52 parts of ethyl acetate was mixed with 25.0 parts of 40% aqueous tetrabutylammonium hydroxide solution, and the resultant mixture was stirred for 1 hour at room temperature. To the obtained mixture, 50 parts of methanol was added, and the resultant mixture was stirred for 16 hours at room temperature. The obtained solution was concentrated to obtain 16.87 parts of a compound represented by the following formula in the form of oil. This is called as compound I2.

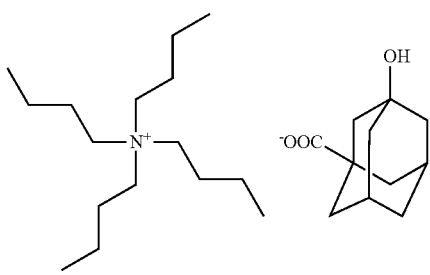

$^1$H-NMR (500.16 MHz, $d_6$-dimethylsulfoxide) δ ppm: 0.94 (t, J=7.65 Hz, 12H), 1.28-1.35 (m, 8H), 1.43 (br, 2H), 1.48 (br, 4H), 1.53-1.61 (m, 14H), 2.02 (br, 2H), 3.17-3.21 (m, 8H)
$^{13}$C-NMR (125.77 MHz, $d_6$-dimethylsulfoxide) δ ppm: 13.45, 19.18, 23.08, 30.46, 35.75, 39.20, 43.99, 45.00, 48.31, 57.52, 67.09, 178.82
MS (ESI(+) Spectrum): M$^+$ 195.1
MS (ESI(−) Spectrum): M$^-$ 242.3

Synthesis Example 2

A mixture of 5.85 parts of 2-hydroxynaphthoic acid and 233.99 parts of methanol was mixed with 21.80 parts of 37% tetrabutylammonium hydroxide methanol solution, and the resultant mixture was stirred for 16 hours at room temperature. The obtained mixture was concentrated and the obtained residue was mixed with 600 parts of ethyl acetate. The resultant solution was washed three times with 110 parts of ion-exchanged water. The obtained solution was concentrated to obtain 12.36 parts of a compound represented by the following formula. This is called as compound I3.

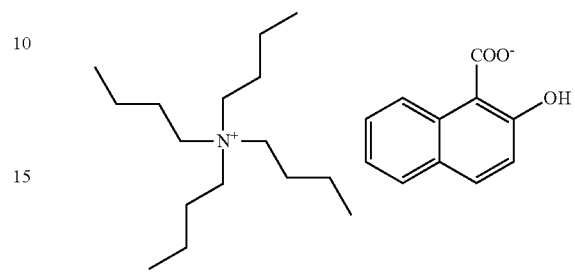

$^1$H-NMR (500.16 MHz, $d_6$-dimethylsulfoxide) δ ppm: 0.90 (t, J=7.95 Hz, 12H), 1.24-1.32 (m, 8H), 1.50-1.56 (m, 8H), 3.11-3.15 (m, 8H), 6.89 (d, J=8.95 Hz, 1H), 7.07-7.10 (m, 1H), 7.29-7.32 (m, 1H), 7.59-7.63 (m, 2H), 9.62 (d, J=8.95 Hz, 1H)
$^{13}$C-NMR (125.77 MHz, $d_6$-dimethylsulfoxide) δ ppm: 13.46, 19.17, 23.02, 57.49, 108.72, 120.39, 121.31, 125.52, 125.91, 126.56, 127.74, 131.86, 134.66, 166.71, 172.45
MS (ESI(+) Spectrum): M$^+$ 242.3
MS (ESI(−) Spectrum): M$^-$ 187.0

Synthesis Example 3

A mixture of 20.00 parts of tetraoctylammonium bromide and 275.32 parts of methanol was mixed with 6.88 parts of 2-hydroxynaphthoic acid, and the resultant mixture was stirred for 16 hours at room temperature. The obtained mixture was concentrated and the obtained residue was mixed with 300 parts of ethyl acetate. The resultant solution was washed with 100 parts of 5% aqueous sodium hydrogen carbonate solution and then washed twice with 100 parts of ion-exchanged water. The obtained solution was concentrated to obtain 23.62 parts of a compound represented by the following formula. This is called as compound I4.

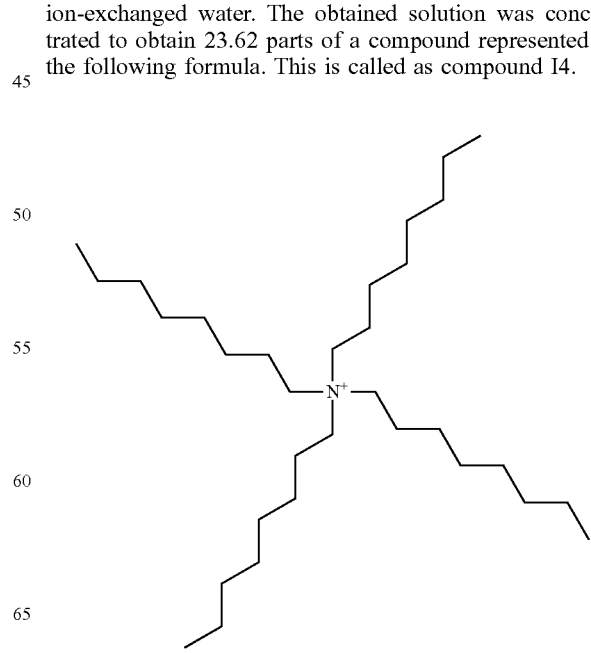

-continued

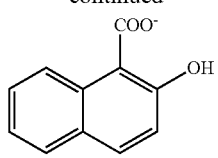

$^1$H-NMR (500.16 MHz, $d_6$-dimethylsulfoxide) δ ppm: 1.10 (t, J=6.95 Hz, 12H), 1.24-1.28 (m, 40H), 1.52 (br, 8H), 3.12 (br, 8H), 6.89 (d, J=8.95 Hz, 1H), 7.06-7.09 (m, 1H), 7.27-7.30 (m, 1H), 7.57-7.62 (m, 2H), 9.64 (d, J=8.90 Hz, 1H)

$^{13}$C-NMR (125.77 MHz, $d_6$-dimethylsulfoxide) δ ppm: 13.83, 20.90, 22.01, 25.64, 28.27, 28.37, 31.11, 57.55, 108.75, 120.24, 121.24, 125.54, 125.73, 126.54, 127.61, 131.70, 134.69, 166.66, 172.46

MS (ESI(+) Spectrum): M$^+$ 466.5
MS (ESI(−) Spectrum): M$^-$ 187.0

Examples 1 to 23 and Comparative Examples 1 and 2

<Acid Generator>

B1
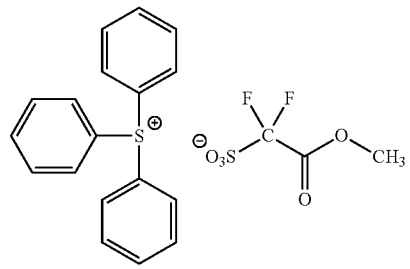

B2
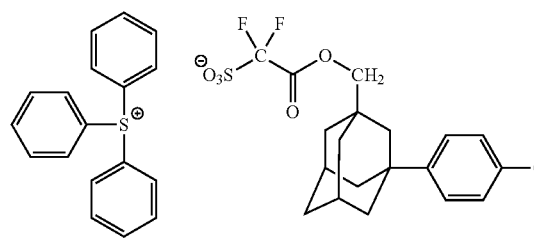

B3
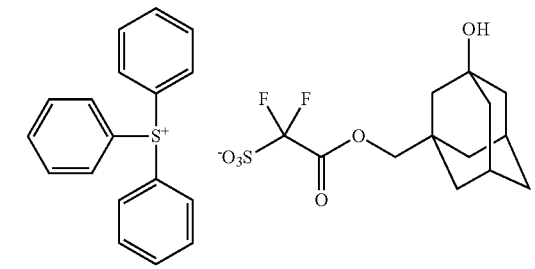

<Resin>
Resin A1, A2, A3, A4, A5, A6, A7, A8
<Compound represented by the formula (I')>

Compound I1
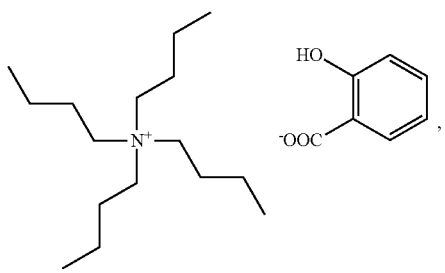

which was available from Tokyo Chemical Industry Co., Ltd. Compound I2, I3, I4
<Basic compound>
C1: tetrabutylammonium hydroxide
<Solvent>

| E1: | propylene glycol monomethyl ether acetate | 440 parts |
| | propylene glycol monomethyl ether | 40 parts |
| | γ-butyrolactone | 5 parts |
| E2: | propylene glycol monomethyl ether acetate | 400 parts |
| | propylene glycol monomethyl ether | 150 parts |
| | γ-butyrolactone | 5 parts |

The following components were mixed and dissolved, further, filtrated through a fluorine resin filter having pore diameter of 0.2 μm, to prepare photoresist compositions.

Resin (kind and amount are described in Table 2)
Acid generator (kind and amount are described in Table 2)
Compound represented by the formula (I') (kind and amount are described in Table 2)
Basic compound (kind and amount are described in Table 2)
Solvent (kind and amount are described in Table 3)

TABLE 2

| Ex. No. | Resin (kind/amount (part)) | Acid Generator (kind/amount (part)) | Basic compound (kind/amount (part)) | Compound represented by the formula (I') (kind/amount (part)) |
| --- | --- | --- | --- | --- |
| Ex. 1 | A1/10 | B2/1.73 | — | I1/0.15 |
| Ex. 2 | A1/10 | B2/1.73 | — | I2/0.173 |
| Ex. 3 | A1/10 | B1/1.16 | — | I1/0.15 |
| Ex. 4 | A1/10 | B1/1.16 | — | I2/0.173 |
| Ex. 5 | A2/10 | B2/2 | — | I1/0.15 |
| Ex. 6 | A3/10 | B2/2 | — | I1/0.15 |
| Ex. 7 | A4/10 | B2/2 | — | I1/0.15 |
| Ex. 8 | A5/10 | B2/2 | — | I1/0.15 |
| Ex. 9 | A6/10 | B2/4 | — | I1/0.3 |
| Ex. 10 | A7/10 | B2/4 | — | I1/0.3 |
| Ex. 11 | A4/10 | B2/2 B3/1.8 | — | I1/0.3 |
| Ex. 12 | A1/10 | B2/3 | — | I3/0.17 |
| Ex. 13 | A1/10 | B2/2.75 | — | I4/0.26 |
| Ex. 14 | A8/10 | B2/2.75 | — | I3/0.17 |
| Ex. 15 | A8/10 | B2/2.75 | — | I4/0.26 |
| Comp. Ex. 1 | A1/10 | B2/1.73 | C1/0.102 | — |

TABLE 3

| Ex. No. | Solvent (kind) | PB (° C.) | PEB (° C.) |
| --- | --- | --- | --- |
| Ex. 1 | E1 | 100 | 100 |
| Ex. 2 | E1 | 100 | 100 |
| Ex. 3 | E1 | 100 | 100 |
| Ex. 4 | E1 | 100 | 100 |
| Ex. 5 | E2 | 100 | 100 |
| Ex. 6 | E2 | 100 | 100 |
| Ex. 7 | E2 | 110 | 110 |
| Ex. 8 | E2 | 100 | 100 |
| Ex. 9 | E2 | 110 | 110 |
| Ex. 10 | E2 | 110 | 110 |
| Ex. 11 | E2 | 110 | 110 |
| Ex. 12 | E2 | 110 | 110 |
| Ex. 13 | E2 | 110 | 110 |
| Ex. 14 | E2 | 110 | 110 |
| Ex. 15 | E2 | 110 | 110 |
| Comp. Ex. 1 | E1 | 100 | 100 |

Silicon wafers were each contacted with hexamethyldisilazane at 90° C. for 60 seconds on a direct hotplate and each of the photoresist compositions prepared as above was spin-coated over the silicon wafer to give a film thickness after drying of 0.04 μm. After application of each of the photoresist compositions, the silicon wafers thus coated with the respective resist compositions were each prebaked on a direct hotplate at a temperature shown in column "PB" in Table 3 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at a temperature shown in column "PEB" in Table 3 for 60 seconds and then to paddle development with an aqueous solution of 2.38% by weight tetramethylammonium hydroxide for 60 seconds.

Each of a photoresist pattern developed on the silicon substrate after the development was observed with a scanning electron microscope, and the results of which are shown in Table 4.

Resolution: The amount of exposure that each photoresist pattern became 1:1 line and space pattern was as effective sensitivity. When line and space pattern having 50 nm or less of the line width was developed at effective sensitivity, resolution is good and its evaluation is marked by "○", when line and space pattern having more than 50 nm and 55 nm or less of the line width was developed at effective sensitivity, resolution is normal and its evaluation is marked by "Δ", and when line and space pattern having more than 55 nm of the line width was developed at effective sensitivity, resolution is bad and its evaluation is marked by "X".

TABLE 4

| Ex. No. | Resolution |
| --- | --- |
| Ex. 1 | ○ |
| Ex. 2 | ○ |
| Ex. 3 | ○ |
| Ex. 4 | ○ |
| Ex. 5 | ○ |
| Ex. 6 | ○ |
| Ex. 7 | ○ |
| Ex. 8 | ○ |
| Ex. 9 | ○ |
| Ex. 10 | ○ |
| Ex. 11 | ○ |
| Ex. 12 | ○ |
| Ex. 13 | ○ |
| Ex. 14 | ○ |
| Ex. 15 | ○ |
| Comp. Ex. 1 | X |

The following components were mixed and dissolved, further, filtrated through a fluorine resin filter having pore diameter of 0.2 μm, to prepare photoresist compositions.

Resin (kind and amount are described in Table 5)
Acid generator (kind and amount are described in Table 5)
Compound represented by the formula (I') (kind and amount are described in Table 5)
Basic compound (kind and amount are described in Table 5)
Solvent (kind and amount are described in Table 6)

TABLE 5

| Ex. No. | Resin (kind/amount (part)) | Acid Generator (kind/amount (part)) | Basic compound (kind/amount (part)) | Compound represented by the formula (I') (kind/amount (part)) |
| --- | --- | --- | --- | --- |
| Ex. 16 | A1/10 | B2/1.73 | — | I1/0.15 |
| Ex. 17 | A1/10 | B2/1.73 | — | I2/0.173 |
| Ex. 18 | A1/10 | B1/1.16 | — | I1/0.15 |
| Ex. 19 | A1/10 | B1/1.16 | — | I2/0.173 |
| Ex. 20 | A2/10 | B2/2 | — | I1/0.15 |
| Ex. 21 | A3/10 | B2/2 | — | I1/0.15 |
| Ex. 22 | A4/10 | B2/2 | — | I1/0.15 |
| Ex. 23 | A5/10 | B2/2 | — | I1/0.15 |
| Comp. Ex. 2 | A1/10 | B2/1.73 | C1/0.102 | — |

TABLE 6

| Ex. No. | Solvent (kind) | PB (° C.) | PEB (° C.) |
| --- | --- | --- | --- |
| Ex. 16 | E1 | 100 | 100 |
| Ex. 17 | E1 | 100 | 100 |
| Ex. 18 | E1 | 100 | 100 |
| Ex. 19 | E1 | 100 | 100 |
| Ex. 20 | E2 | 100 | 100 |
| Ex. 21 | E2 | 100 | 100 |
| Ex. 22 | E2 | 110 | 110 |
| Ex. 23 | E2 | 100 | 100 |
| Comp. Ex. 2 | E1 | 100 | 100 |

Silicon wafers were each contacted with hexamethyldisilazane at 90° C. for 60 seconds on a direct hot plate and each of the resist compositions prepared as above was spin-coated over the silicon wafer to give a film thickness after drying of 0.04 μm. After application of each of the resist compositions, the silicon wafers thus coated with the respective resist compositions were each prebaked on a direct hotplate at a temperature shown in column "PB" in Table 6 for 60 seconds. Using an EUV (extreme ultraviolet) exposure system, each wafer on which the respective resist film had been thus formed was exposed to a line and space pattern, while changing stepwise the exposure quantity.

After the exposure, each wafer was subjected to post-exposure baking on a hotplate at a temperature shown in column "PEB" in Table 6 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 7.

Resolution: The amount of exposure that each photoresist pattern became 1:1 line and space pattern was as effective sensitivity. When line and space pattern having 24 nm or less of the line width was developed at effective sensitivity, resolution is good and its evaluation is marked by "◯", when line and space pattern having more than 24 nm and 28 nm or less of the line width was developed at effective sensitivity, resolution is normal and its evaluation is marked by "Δ", and when line and space pattern having 28 nm of the line width was not developed at effective sensitivity, resolution is bad and its evaluation is marked by "X".

TABLE 7

| Ex. No. | Resolution |
| --- | --- |
| Ex. 16 | ◯ |
| Ex. 17 | ◯ |
| Ex. 18 | ◯ |
| Ex. 19 | ◯ |
| Ex. 20 | ◯ |
| Ex. 21 | ◯ |
| Ex. 22 | ◯ |
| Ex. 23 | ◯ |
| Comp. Ex. 1 | X |

The photoresist composition of the present invention provides a good resist pattern having good resolution, and is especially suitable for KrF excimer laser lithography, EUV lithography and EB lithography.

What is claimed is:

1. A photoresist composition comprising a resin which comprises a structural unit derived from a compound represented by the formula (a1-1):

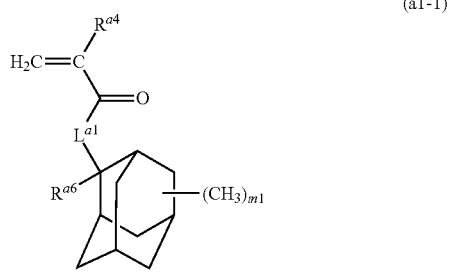

(a1-1)

wherein $R^{a4}$ represents a hydrogen atom or a methyl group, $R^{a6}$ represents a C1-C8 aliphatic hydrocarbon group or a C3-C10 saturated cyclic hydrocarbon group, $L^{a1}$ represents *—O— or *—O—(CH$_2$)$_{k1}$—CO—O— in which * represents a binding position to —CO—, and k1 represents an integer of 1 to 7, and m1 represents an integer of 0 to 14;

a structural unit derived from a compound represented by the formula (a2-0):

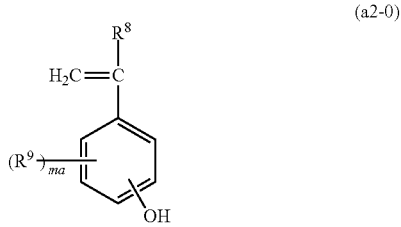

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a structural unit derived from a compound selected from the group consisting of styrene, a compound having no acid-labile group but having a lactone ring and a compound represented by formula (a2-1):

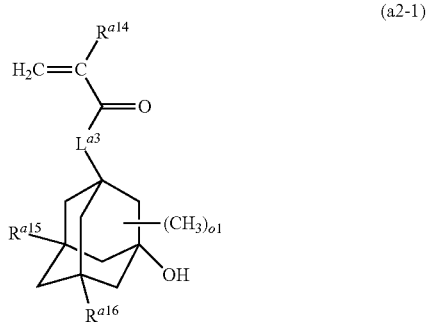

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—(CH$_2$)$_{k2}$—CO—O— in which * represents a binding position to —CO—, and k2 represents an integer of 1 to 7, and o1 represents an integer of 0 to 10, which resin is insoluble or poorly soluble in an alkali aqueous solution but becomes soluble in an alkali aqueous solution by the action of an acid;

no other acid generator than an acid generator represented by formula (B1)

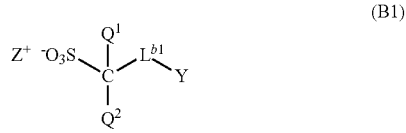

(B1)

in which $Q^1$ and $Q^2$ each independently represent a fluorine atom or a C1-C6 perfluoroalkyl group;

wherein $L^{b1}$ represents *—CO—O-$L^{b2}$-, *—CO—O-$L^{b4}$-CO—O-$L^{b3}$, *-$L^{B7}$-O-$L^{b6}$-, *—CO—O-$L^{b8}$-O—, or *—CO—O-$L^{b10}$-O-$L^{b9}$-CO—O— in which $L^{b2}$ represents a single bond or a C1-C15 alkanediyl group, $L^{b3}$ represents a single bond or a C1-C12 alkanediyl group, $L^{b4}$ represents a single bond or a C1-C13 alkanediyl group, with proviso that total carbon number of $L^{b3}$ and $L^{b4}$ is 1 to 13, $L^{b6}$ represents a C1-C15 alkanediyl group, $L^{b7}$ represents a C1-C15 alkanediyl group, with proviso that total carbon number of $L^{b6}$ and $L^{b7}$ is 1 to 16, $L^{b8}$ represents a C1-C14 alkanediyl group, $L^{b9}$ represents a C1-C11 alkanediyl group, $L^{b10}$ represents a C1-C11 alkanediyl group, with proviso that total carbon number of $L^{b9}$ and $L^{b10}$ is 1 to 12, and * represents a binding position to —C($Q^1$)($Q^2$)-, wherein Y represents a C3-C18 saturated cyclic hydrocarbon group which can have one or more substituents, and one or more methylene groups in the saturated cyclic hydrocarbon group can be replaced by —O—, —CO—, or —SO$_2$— and wherein $Z^+$ represents an organic cation represented by formula (b2-1):

(b2-1)

where $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 aliphatic hydrocarbon group, a C3-C36 saturated cyclic hydrocarbon group or a C1-C12 alkoxy group; and a compound represented by the formula (I'):

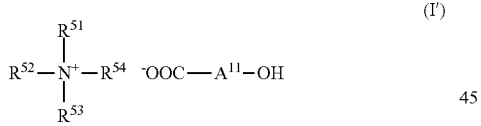
(I')

wherein the cation part represents a cation by any one of the following formulae:

(IA-1)

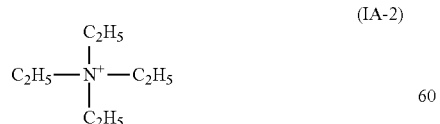
(IA-2)

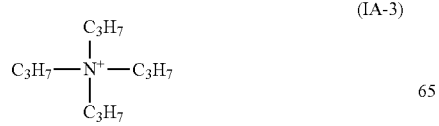
(IA-3)

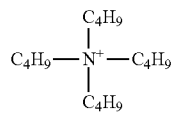
(IA-4)

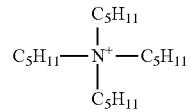
(IA-5)

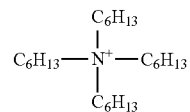
(IA-6)

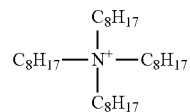
(IA-7)

and the anion part represents an anion represented by any one of the following formulae

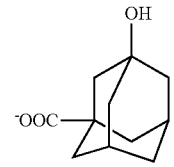
(IB-1)

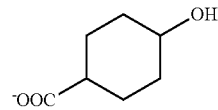
(IB-2)

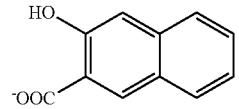
(IB-6)

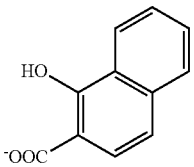
(IB-7)

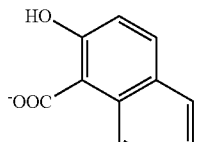
(IB-8)

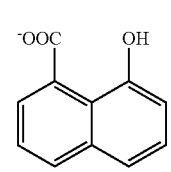
(IB-9)

-continued

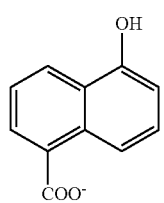
(IB-10)

2. A process for producing a photoresist pattern comprising the following steps (1) to (5):
   (1) a step of applying the photoresist composition according to claim 1 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

3. The process according to claim 2 wherein the photoresist film is exposed using an electron beam lithography system or an extreme ultraviolet lithography system in step (3).

4. The photoresist composition according to claim 1 wherein the resin consists of a structural unit derived from the compound represented by formula (a1-1), a structural unit derived from a compound represented by formula (a2-0), and a structural unit derived from a compound selected from the group consisting of styrene, a compound having no acid-labile group but having a lactone ring and a compound represented by formula (a2-1).

* * * * *